(12) United States Patent
Cho et al.

(10) Patent No.: US 7,750,122 B2
(45) Date of Patent: Jul. 6, 2010

(54) ANTI-TRKB MONOCLONAL ANTIBODIES AND USES THEREOF

(75) Inventors: Seongeun Cho, Hillsborough, NJ (US); Davinder Singh Gill, Andover, MA (US); Xiang Yang Tan, Reading, MA (US); Ming Diana Qian, Sugar land, TX (US)

(73) Assignee: Wyeth LLC, Madison, NJ (US)

( * ) Notice: Subject to any disclaimer, the term of this patent is extended or adjusted under 35 U.S.C. 154(b) by 537 days.

(21) Appl. No.: 11/446,875

(22) Filed: Jun. 5, 2006

(65) Prior Publication Data
US 2007/0059304 A1    Mar. 15, 2007

Related U.S. Application Data

(60) Provisional application No. 60/687,705, filed on Jun. 6, 2005.

(51) Int. Cl.
C07K 16/00 (2006.01)
A61K 39/395 (2006.01)
C12N 5/12 (2006.01)
C07K 1/14 (2006.01)
C07K 16/40 (2006.01)

(52) U.S. Cl. ............... 530/387.1; 424/130.1; 435/326; 530/355; 530/388.25

(58) Field of Classification Search ............. None
See application file for complete search history.

(56) References Cited

U.S. PATENT DOCUMENTS

| | | | |
|---|---|---|---|
| 5,231,001 A | 7/1993 | Kaplan et al. | 435/7.21 |
| 5,601,820 A | 2/1997 | Brodeur et al. | 424/138.1 |
| 5,622,862 A | 4/1997 | Squinto et al. | 435/353 |
| 5,625,121 A | 4/1997 | Klein et al. | 800/9 |
| 5,688,911 A | 11/1997 | Schneider et al. | 530/324 |
| 5,753,225 A | 5/1998 | Clary et al. | 424/130.1 |
| 5,811,396 A | 9/1998 | Kaplan et al. | 514/12 |
| 5,817,471 A | 10/1998 | Kaplan et al. | 435/7.21 |
| 5,844,092 A | 12/1998 | Presta et al. | 530/387.3 |
| 5,877,016 A | 3/1999 | Presta et al. | 435/325 |
| 5,880,153 A | 3/1999 | Neuman et al. | 514/557 |
| 5,910,574 A | 6/1999 | Presta et al. | 530/388.22 |
| 6,025,166 A | 2/2000 | Presta et al. | 435/70.1 |
| 6,027,927 A | 2/2000 | Presta et al. | 435/194 |
| 6,153,189 A | 11/2000 | Presta et al. | 424/134.1 |
| 6,656,465 B2 | 12/2003 | Clary et al. | 424/130.1 |
| 7,060,429 B2 | 6/2006 | Krueger et al. | 435/4 |
| 2002/0146416 A1 | 10/2002 | Presta et al. | 424/143.1 |
| 2002/0169154 A1 | 11/2002 | Ruggeri et al. | 514/211.08 |
| 2003/0157099 A1 | 8/2003 | Presta et al. | 424/143.1 |
| 2004/0058416 A1 | 3/2004 | Presta et al. | 435/69.1 |
| 2004/0110711 A1 | 6/2004 | Krueger et al. | 514/44 |
| 2004/0137513 A1 | 7/2004 | Devaux et al. | 435/7.1 |
| 2004/0186044 A1 | 9/2004 | Cosgaya et al. | 514/2 |
| 2006/0148749 A1 | 7/2006 | Krueger et al. | 514/44 |

FOREIGN PATENT DOCUMENTS

| | | |
|---|---|---|
| WO | WO 95/15180 | 6/1995 |
| WO | WO95/15180 | 6/1995 |
| WO | WO 96/01837 | 1/1996 |
| WO | WO96/01837 | 1/1996 |

OTHER PUBLICATIONS

International Preliminary Report on Patentability for PCT/US2006/021878, mailed Dec. 21, 2007.
Geetha, et al., "Association of the Atypical Protein Kinase C-interacting Protein p62/ZIP with Nerve Growth Factor Receptor TrkA Regulates Receptor Trafficking and Erk5 Signaling", Journal of Biological Chemistry (2003), v. 278, No. 7, pp. 4730-4739.
Qian, et al., "Novel Agonist Monoclonal Antibodies Activate TrkB Receptors and Demonstrate Potent Neurotrophic Activities", Journal of Neuroscience (2006), v. 26, No. 37, pp. 9394-9403.
International Search Report (PCT/US2006/021878).
"Monoclonal Mouse Anti-Trk (B-3) Purified"; Santa Cruz Biotechnology, Inc.; printed Aug. 3. 2006, 3 pp; website: http://www.alzforum.org/res/com/ant/NGFRredo/santaSC7268.asp?CompanyID=219.
"Anti-human TrkB Antibody"; R & D Systems, Inc.; printed Aug. 3, 2006, 1 pg; catalog No. AF397.
"Anti-mouse TrkB Antibody"; R & D Systems, Inc.; printed Aug. 3, 2006, 1 pg; catalog No. AF1494.
"Antibodies to Nerve Growth Factor Receptor Proteins"; printed Aug. 3, 2006, 9 pp; website: http://www.alzforum.org/res/com/ant/default.asp?antigenID=48.
"Product Sheet: Anti-human trK A/trK B Receptors (monoclonal)"; Austral Biologicals Catalog; catalog No. MR-701A-5; printed Aug. 3, 2006, 1 pg; website: http://www.australbiologicals.com/index.php?what=catalog&id=241.
"Biotinylated Anti-human TrkB Antibody", R & D Systems, Inc.; printed Aug. 3, 2006, 1 pg; catalog No. BAF397.
"Biotinylated Anti-mouse TrkB Antibody", R & D Systems, Inc.; printed Aug. 3, 2006, 1 pg; catalog No. BAF1494.
"Monoclonal Anti-human TrkB Antibody", R & D Systems, Inc.; printed Aug. 3, 2006, 1 pg; catalog No. MAB397.
"Monoclonal Anti-mouse TrkB Antibody", R & D Systems, Inc.; printed Aug. 3, 2006, 1 pg; catalog No. MAB1494.
"Monoclonal Anti-human TrkB Antibody", R & D Systems, Inc.; printed Aug. 3, 2006, 1 pg; catalog No. MAB3971.

(Continued)

Primary Examiner—Jeffrey Stucker
Assistant Examiner—Aditi Dutt
(74) Attorney, Agent, or Firm—Maria Restrepo-Hartwig

(57) ABSTRACT

The present invention provides monoclonal antibodies for human TrkB. In certain embodiments the inventive antibodies bind and activate human TrkB. In certain embodiments the inventive antibodies are selective for human TrkB in that they do not bind (or activate) human TrkA or human TrkC. In some embodiments the inventive monoclonal antibodies cross-react with murine TrkB. Humanized or veneered versions of the inventive antibodies are also encompassed. Pharmaceutical compositions that comprise inventive antibodies are provided as are methods for preparing the inventive antibodies and methods of using these for treatment, detection or purification purposes.

27 Claims, 41 Drawing Sheets
(31 of 41 Drawing Sheet(s) Filed in Color)

OTHER PUBLICATIONS

Product Search Results, R & D Systems, Inc.; printed Aug. 3, 2006, 1 pg; website- http://www.rndsystems.com/product_results.aspx?m=2210&c=6.

LeSauteur, et al., "Potent Human p140-TrkA Agonists Derived from an Anti-Receptor Monoclonal Antibody", The Journal of Neoroscience (1996), v. 16, No. 4, pp. 1308-1316.

Clary, et al., "TrkA Cross-linking Mimics Neuronal Responses to Nerve Growth Factor", Molecular Biology of the Cell (1994), v. 5, pp. 549-563.

Abcam Search Results; printed Aug. 4, 2006; 1 pg; website- http://abcam.com/index.html?pageconfig=searchresults&t0=5938678-16916328.

Abcam Catalog Search Results; printed Aug. 4, 2006; 1 pg; website-http://abcam.com/index.html?pageconfig=searchresults.

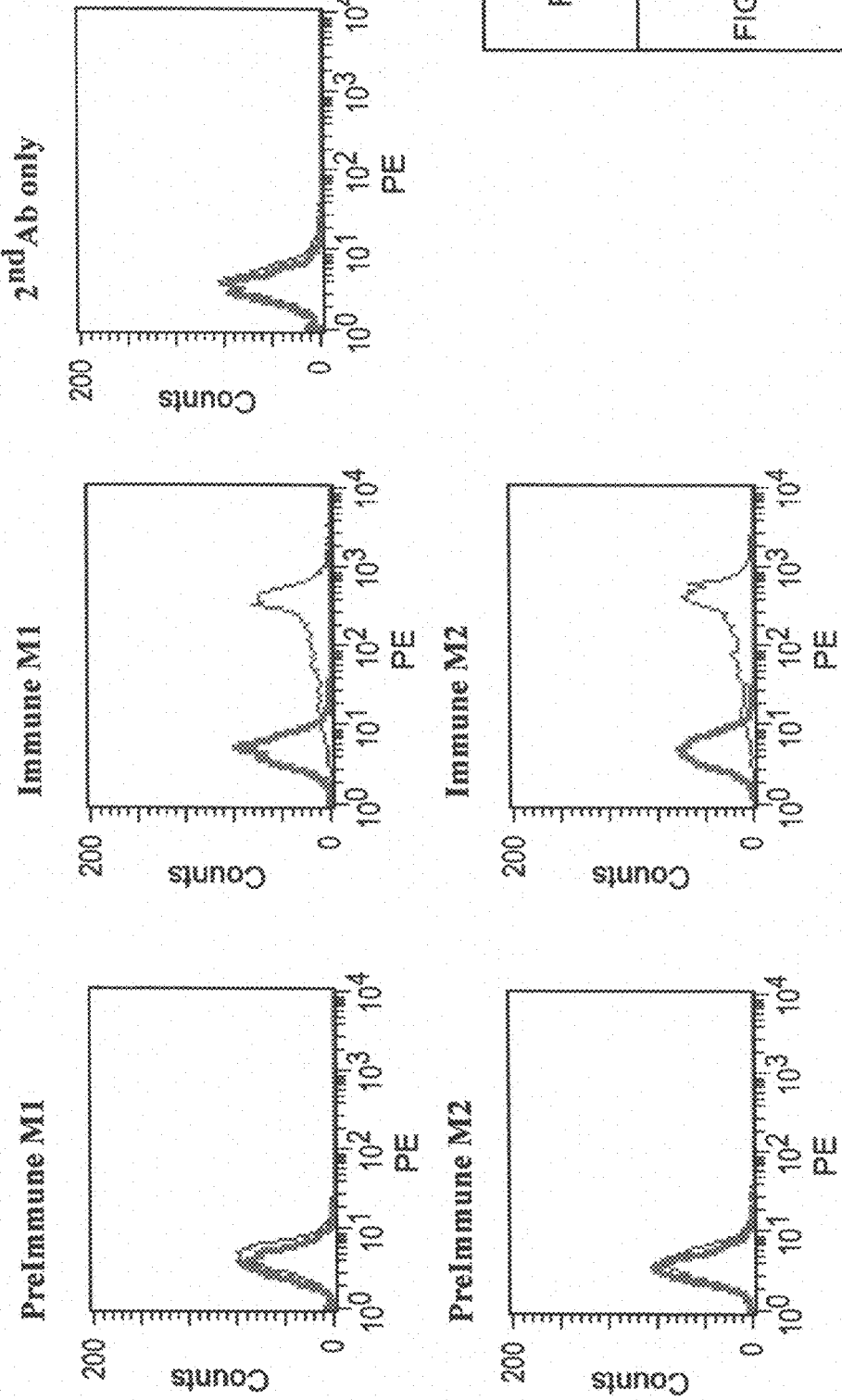

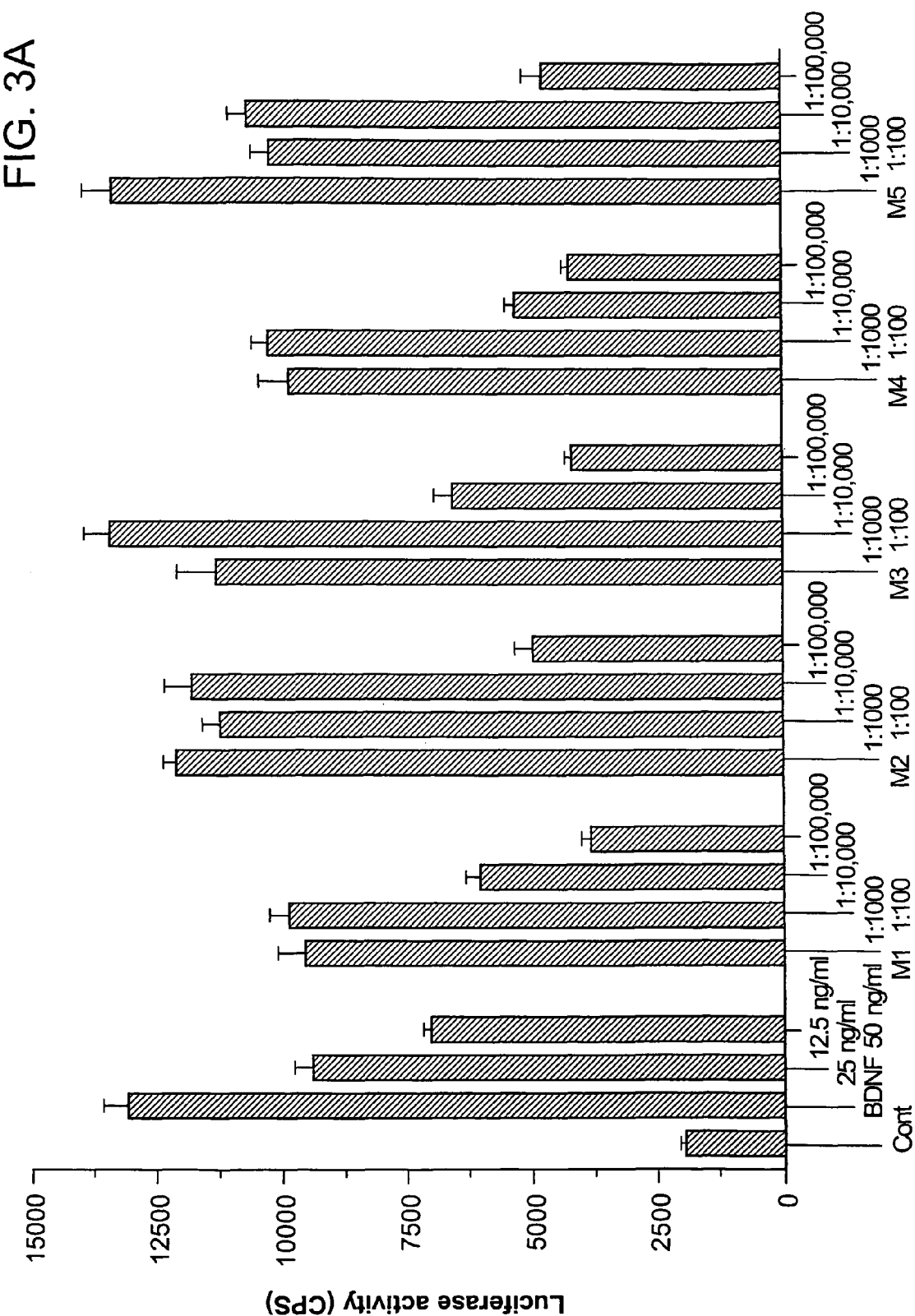

| mAb | Luciferase activity | |
|---|---|---|
| | Fold inc | EC50 (nM) |
| 2 E8 | 7.7 | 0.28 |
| 4 C7 | 6.9 | 0.29 |
| 5 D8 | 7.8 | 1.07 |
| 5 E11 | 6.9 | 0.97 |
| 6 D5 | 6.6 | 0.36 |
| 6 E2 | 7.5 | 0.46 |
| 6 E6 | 7.1 | 0.30 |
| 7 E1 | 6.0 | 0.05 |
| 7 F5 | 6.6 | 0.33 |
| 11 E1 | 6.6 | 0.21 |
| 16 E11 | 6.8 | 0.31 |
| 17 D11 | 6.6 | 0.23 |
| 18 C3 | 6.7 | 0.29 |
| 19 E12 | 7.7 | 0.14 |
| 29 D7 | 7.0 | 0.10 |

FIG. 4B

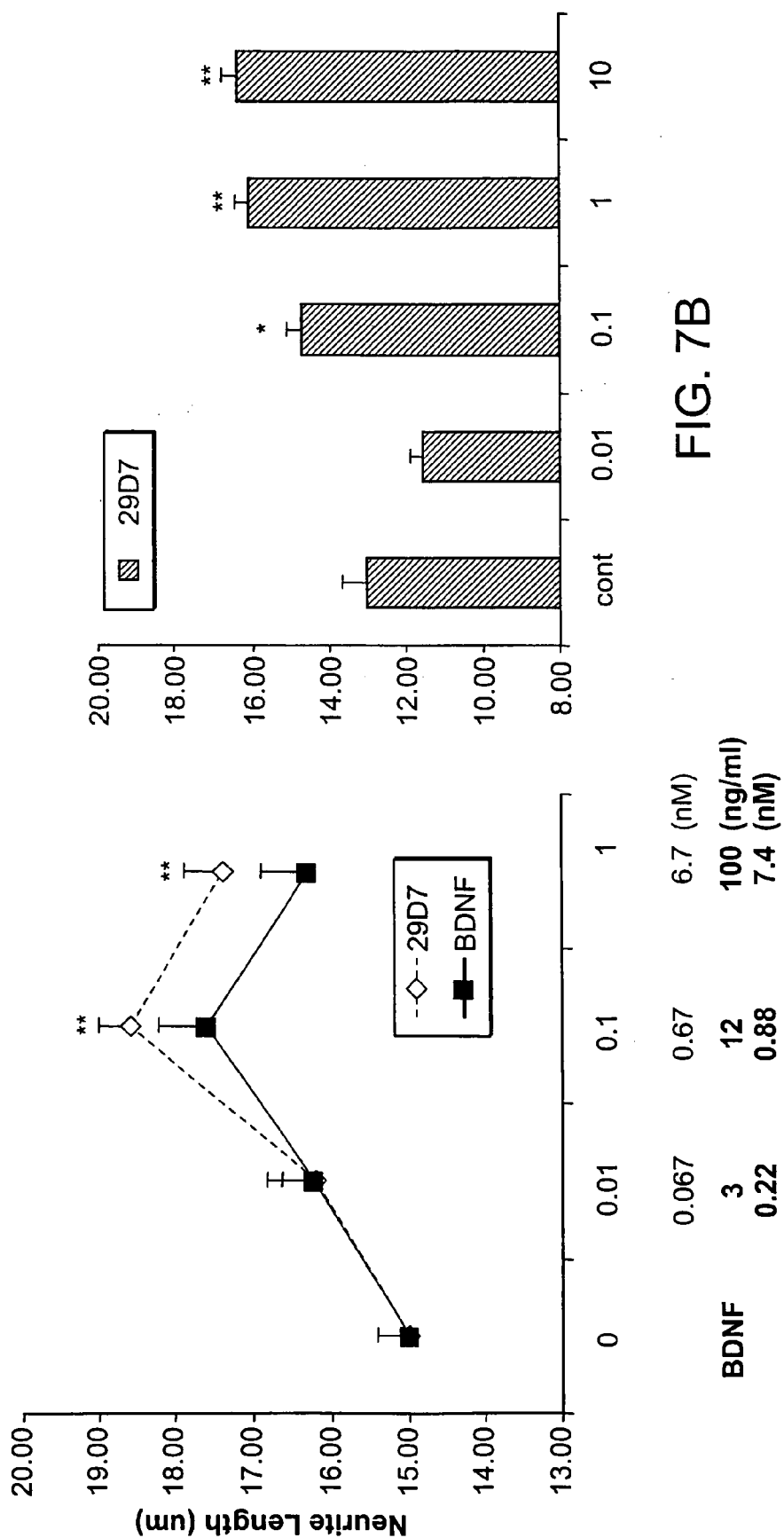

| FIG. 13A |
| FIG. 13B |
| FIG. 13C |
| FIG 13D |

FIG. 13

| CS_2_A6 | CS_2_B6 | CS_2_C1 |
| CS_2_C2 | CS_2_C3 | CS_2_C5 |

FIG. 13A

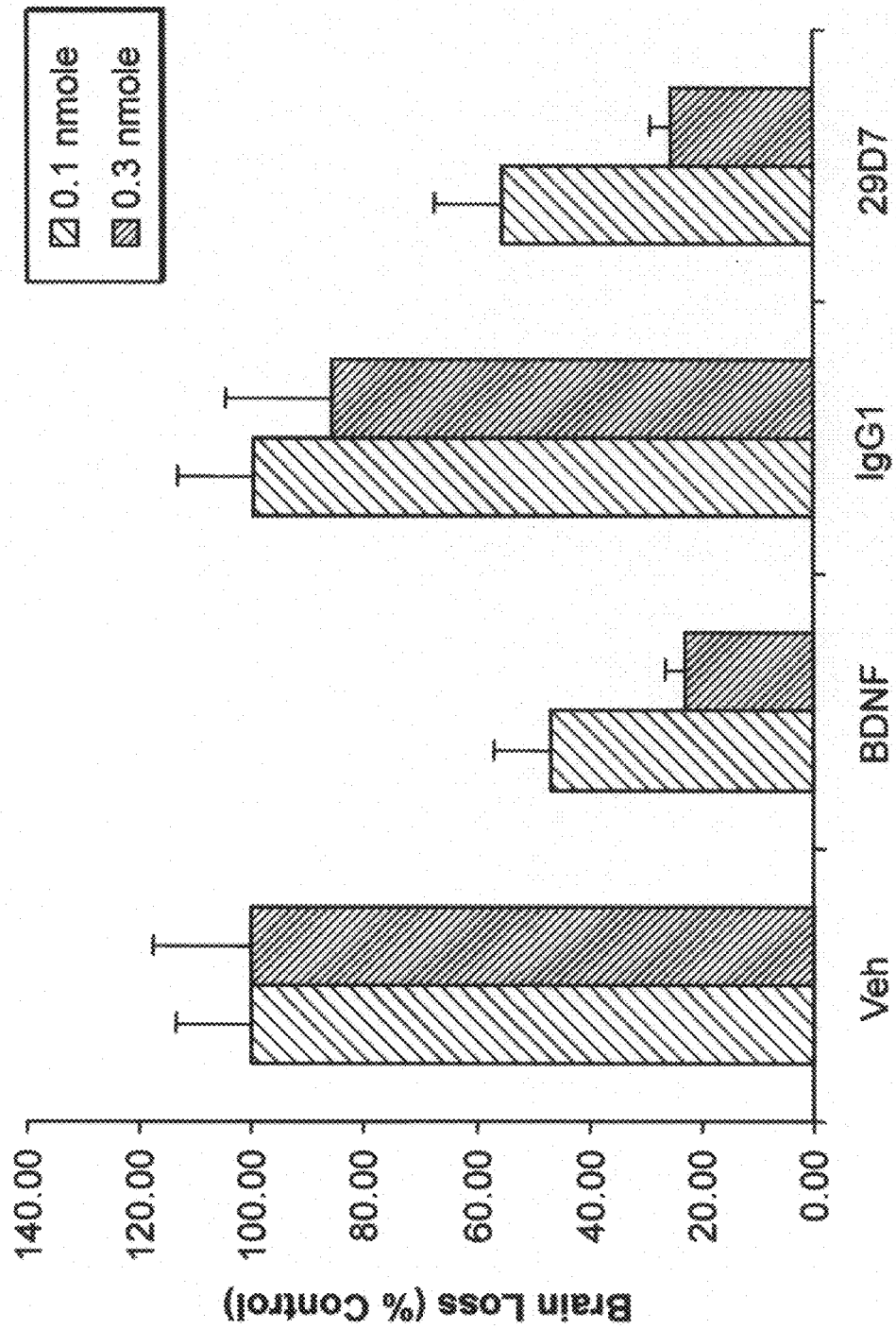

ANTI-TRKB MONOCLONAL ANTIBODIES AND USES THEREOF

PRIORITY INFORMATION

The present application claims the benefit of U.S. Ser. No. 60/687,705, filed Jun. 6, 2005, the entire contents of which are hereby incorporated by reference.

BACKGROUND OF THE INVENTION

Trk tyrosine kinase receptors are multi-domain single-transmembrane receptors that play an important role in a wide spectrum of neuronal responses including survival, differentiation, growth and regeneration. They are high affinity receptors for neurotrophins, a family of protein growth factors, which includes nerve growth factor (NGF), brain-derived neurotrophic factor (BDNF), neurotrophin-3 (NT-3) and neurotrophin-4/5 (NT-4/5). The neurotrophins share highly conserved structural features, yet their unique amino acid sequences allow each member to elicit high affinity interactions with the extracellular domain of specific Trk receptors, namely TrkA, B or C. Thus, NGF is a preferred ligand for TrkA; BDNF and NT-4/5 are preferred ligands for TrkB; and NT-3 has been shown to bind TrkC, although it also appears to bind TrkA and TrkB with lower affinities.

Among the Trk receptors, the role of TrkB has been well characterized in the central nervous system (CNS). TrkB are widely distributed in the brain, including in the neocortex, hippocampus, striatum, olfactory formation and brainstem. Using BDNF as a cognate ligand, the indispensable roles of TrkB in neuronal survival, differentiation and neuroregeneration have been shown in a number of neurodegenerative models, including stroke, spinal cord injury, axotomy and ALS.

Through various signaling analyses and receptor knockout systems, the responses of BDNF have been shown to depend on the binding and activation of TrkB. As noted, Trk receptors are multi-domain single-transmembrane proteins. They consist of an extracellular ligand binding domain, a transmembrane region, and an intracellular tyrosine kinase domain. The extracellular domain is composed of a leucine-rich motif flanked by two cysteine clusters and two immunoglobulin (Ig)-like domains. Trk receptors have been shown to interact with their ligands mainly through the second Ig-like domain, although contribution of other regions such as a leucine-rich motif and the first Ig domain in ligand-docking has been proposed. The crystal structures of the ligand binding domains of Trk receptors as well as ligand-receptor complexes have been resolved. The ligand-receptor interface appears to consist of two patches: one for a conserved binding motif shared among all neurotrophins and the other specific for each neurotrophin.

Upon the binding of neurotrophins to Trk receptors, receptor dimerization and subsequent conformational changes occur, which are believed to lead to activation of the intracellular tyrosine kinase domain. There are several conserved tyrosines in the intracellular domain of Trk receptors. Phosphorylation of the autoregulatory loop of the kinase domain activates the kinase activity, and phosphorylation of other residues promotes signaling by creating docking sites for adaptor proteins that couple these receptors to intracellular signaling cascades, including Ras/extracellular signal regulated kinase (ERK) protein kinase pathway, the PI3K/Akt kinase pathway and phospholipase C-gamma. Although somewhat overlapping, these individual pathways are involved in discrete biological activities: Ras/MAPK regulates neuronal differentiation and proliferation, PI3K/Akt pathways control actin dynamics and survival and PLC gamma is involved in calcium mobilization.

To date, there exist no successful examples of reagents that act as potent and selective in vivo agonists of TrkB. While BDNF, as a recombinant protein, has been shown to increase neuronal survival and neuroregeneration in a number of CNS degenerative models in vitro and in vivo, the outcomes of BDNF protein therapy in clinics have been negative, most likely because BDNF has a short in vivo half-life. There is therefore a need in the art for pharmaceutical reagents that act as potent and selective in vivo agonists of TrkB.

SUMMARY OF THE INVENTION

The present invention provides monoclonal antibodies for human TrkB. In certain embodiments the inventive antibodies bind and activate human TrkB. In certain embodiments the inventive antibodies are selective for human TrkB in that they bind preferentially to TrkB over human TrkA or human TrkC. In some embodiments the inventive monoclonal antibodies cross-react with murine TrkB.

The invention also provides pharmaceutical compositions that comprise one or more of these antibodies. The invention further provides methods for preparing the inventive monoclonal antibodies. Humanized or veneered versions of the inventive antibodies are also encompassed as are the hybridomas that produce the inventive antibodies.

The invention further provides methods of using these monoclonal antibodies as agonists of TrkB. In certain embodiments the monoclonal antibodies are used as agonists of human TrkB. According to such embodiments, the antibodies may be used to treat conditions which require TrkB activation, including neurological conditions.

The invention yet further provides methods for detecting TrkB in a sample and methods for purifying TrkB from a sample using the inventive antibodies.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 depicts some of the results that were obtained when three anti-TrkB antibodies, 18C3, 29D7 and 17D11, which were shown to bind to recombinant murine TrkB (rmTrkB), were tested in rat cerebellar granule neuron (CGN) cultures for activity against the endogenous rat TrkB receptor. Results are shown for a neurite outgrowth assay (FIGS. 7A and 7B) and a neuroprotection assay (29D7 only) (FIG. 7B).

FIGS. 13A-13D show the binding specificity of TrkB selected scFv antibodies tested using the FACS assay. The data shows that TrkB selected scFv antibodies react with membrane associated TrkB in a specific manner (filled histograms) with no cross-reactivity to control cells (open histograms).

DESCRIPTION OF CERTAIN EMBODIMENTS

Figure 1A:
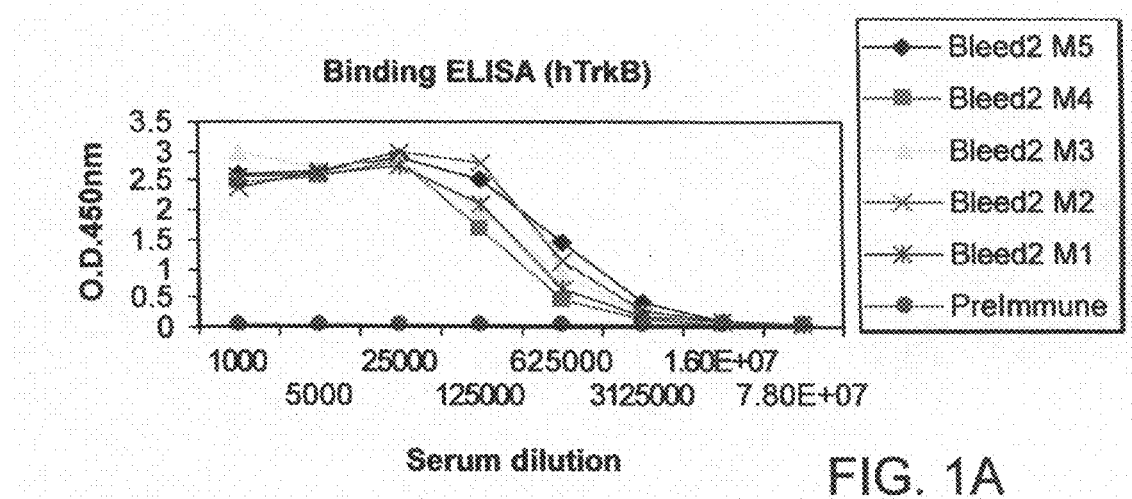
FIG. 1 depicts TrkB-specific antibody activities in immune sera from five immunized mice (M1-M5). Immune sera binding results from an ELISA assay with a recombinant protein that includes the extracellular domain of human TrkB fused to the Fc region of human IgG1 (rhTrkB-EDC-Fc) are shown in (FIG. 1A). Immune sera binding results from an ELISA assay with a recombinant protein that includes the extracellular domain of murine TrkB (rmTrkB-EDC) are shown in (FIG. 1B). The extent to which immune sera could block the interaction of rhTrkB-EDC-Fc and BDNF in a competition ELISA assay are shown in (FIG. 1C). Immune sera binding to surface rhTrkB on HEK-293 cells are shown in (FIG. 1D).

The present invention stemmed in part from the realization that monoclonal antibodies that specifically bind to the extracellular domains of the TrkB receptor might dimerize TrkB and be sufficient to induce the activation of the receptor and biological responses similar to those mediated by BDNF.

Monoclonal antibodies in general represent a unique class of proteins that have diverse utilities in research, medical diagnosis, and the clinical treatment of disease. Advantageously, monoclonal antibodies are thought to have greater pharmacokinetic stability than recombinant proteins such as BDNF thereby allowing for sustainable pharmacological effects that have a significant benefit for clinical applications. For example, the current clinically approved uses of monoclonal antibody medications include prevention of organ transplant rejection, treatment of cancers (e.g., breast, colon, non-Hodgkin's lymphoma, leukemia), rheumatoid arthritis, prophylaxis against respiratory syncytial virus disease, Crohn's disease, percutaneous coronary intervention, and asthma. Other medical applications for treating a variety of human diseases with monoclonal antibodies are also currently in clinical trials. The biological effects of these monoclonal antibodies are generally conveyed by blocking or neutralizing molecular events exerted by endogenous ligands, thus primarily acting as specific high-affinity antagonists. In the present invention, monoclonal antibodies are used as agonists that mimic the biological effects of receptor-ligand interactions.

1. Monoclonal Antibodies and Hybridomas

In one aspect, the present invention provides monoclonal antibodies that bind human TrkB (SEQ ID NO:1). In certain embodiments, these antibodies bind human TrkB (SEQ ID NO:1) with an $ED_{50}$ in the range of about 10 pM to about 500 nM, for example in the range of about 10 pM to about 1 nM, about 10 pM to about 100 pM, or about 10 pm to about 50 pM. As used herein the term "about" is defined to encompass variations of ±15%.

In one embodiment the inventive antibodies are also agonists of human TrkB. In certain embodiments, these antibodies activate human TrkB (SEQ ID NO:1) with an $EC_{50}$ in the range of about 10 pM to about 500 nM, for example in the range of about 10 pM to about 1 nM, about 10 pM to about 100 pM, or about 10 pM to about 50 pM.

In one embodiment, inventive antibodies are selective for human TrkB (SEQ ID NO:1) in that they bond preferentially to TrkB (SEQ ID NO:1) over human TrkA (SEQ ID NO:5) or human TrkC (SEQ ID NO:6). In some embodiments, inventive antibodies do not bind to human TrkA or human TrkC. As defined herein, an inventive antibody "does not bind" human TrkA (SEQ ID NO:5) or human TrkC (SEQ ID NO:6) if it exhibits no detectable binding with these receptors at concentrations above about 1 nM, for example above about 10 nM, above about 100 nM or above about 1 μM.

In one embodiment, inventive antibodies are selective for human TrkB in that they do not activate human TrkA (SEQ ID NO:5) or human TrkC (SEQ ID NO:6). As defined herein, an inventive antibody "does not activate" human TrkA (SEQ ID NO:5) or human TrkC (SEQ ID NO:6) if it causes no detectable activation with these receptors at concentrations above about 1 nM, for example above about 10 nM, above about 100 nM or above about 1 μM.

In one embodiment, inventive antibodies block the binding between BDNF and human TrkB (SEQ ID NO:1) with an $IC_{50}$ in the range of about 100 pM to about 500 nM, for example in the range of about 100 pM to about 1 nM, or about 100 pM to about 500 pM. In other embodiments these antibodies do not block the binding between BDNF and human TrkB (SEQ ID NO:1). As defined herein, an inventive antibody "does not block" the binding between BDNF and human TrkB (SEQ ID NO:1) if it exhibits no detectable blocking activity at concentrations above about 1 nM, for example above about 10 nM, above about 100 nM or above about 1 μM.

In certain embodiments the antibodies of the invention belong to an IgG isotype, e.g., the IgG1, IgG2a or IgG2b isotype.

In another aspect, the present invention provides monoclonal antibodies with any of the properties from above that further bind and/or activate mouse TrkB (SEQ ID NO:2). In certain embodiments, these antibodies bind and/or activate mouse TrkB (SEQ ID NO:2) with an $ED_{50}$ in the range of about 10 pM to about 500 nM, for example in the range of about 10 pM to about 1 nM, including in the range of about 10 pM to about 500 pM and the range of about 10 pM to about 100 pM.

In another aspect, the present invention provides monoclonal antibodies with any of the properties from above that further bind one or more specific epitopes of human TrkB (SEQ ID NO:1) and optionally one or more specific epitopes of mouse TrkB (SEQ ID NO:2). In certain embodiments, these antibodies bind one or both epitopes of human TrkB with the sequences KNEYGKD (SEQ ID NO:7, amino acids 364 to 370 of SEQ ID NO:1) and KGNPKP (SEQ ID NO:8, amino acids 308 to 313 of SEQ ID NO:1). In one embodiment, these antibodies also bind one or both epitopes of mouse TrkB with the sequences KNEYGKD (SEQ ID NO:7, amino acids 364 to 370 of SEQ ID NO:2) and RGNPKP (SEQ ID NO:9, amino acids 308 to 313 of SEQ ID NO:2). In other embodiments, the present invention provides antibodies that bind an epitope of human TrkB with the sequence ENLVGED (SEQ ID NO:10, amino acids 269 to 275 of SEQ ID NO:1) and optionally an epitope of human TrkB with the sequence AGDPVP (SEQ ID NO:11, amino acids 221 to 226 of SEQ ID NO:1). In one embodiment, these antibodies also bind an epitope of mouse TrkB with the sequence ENLVGED (SEQ ID NO:10, amino acids 269 to 275 of SEQ ID NO:2).

In yet another aspect, the present invention provides hybridomas that produce any of these monoclonal antibodies. For example, hybridomas that were deposited with the ATCC on Aug. 18, 2005 and have been given ATCC patent deposit designations PTA-6948 (17D11) and PTA-6949 (29D7) are provided.

In still another aspect, the present invention provides monoclonal antibodies that are produced by the hybridomas that were deposited with the ATCC on Aug. 18, 2005 and have been given ATCC patent deposit designations PTA-6948

(17D11) and PTA-6949 (29D7), respectively. The present invention also provides antibodies that block the binding of these antibodies and therefore share the same binding epitope on human TrkB (SEQ ID NO:1).

2. Preparation of Monoclonal Antibodies and Hybridomas

It is to be understood that the monoclonal antibodies of the invention can be prepared by any known method. For example, they can be prepared using synthetic, recombinant or hybridoma technology (e.g., as described in *Antibodies: A Laboratory Manual*, Ed. by E. Harlow and D. Lane, Cold Spring Harbor Laboratory Press, 1988 or *Monoclonal Antibodies: Principles and Practice* by J. W. Goding, Academic Press, 1996). In particular it will be appreciated that the inventive antibodies can be prepared by initially immunizing an animal with human TrkB or a derivative thereof (e.g., a recombinant protein that includes the extracellular domain of human TrkB) and then preparing monoclonals from suitably prepared hybridomas.

In one aspect, the monoclonal antibodies of the present invention are prepared by standard hybridoma technology using at least two protein immunogens that are derived from TrkB proteins of different species. For example, the immunogens may include a first immunogen that was derived from human TrkB and a second immunogen that was derived from a non-human TrkB. Preferably the immunogens each include the extracellular domain of TrkB. In certain embodiments the at least two immunogens are combined as a mixture for immunization purposes.

In one embodiment, the first of these immunogens is a recombinant protein that includes the extracellular domain (ECD) of human TrkB. The ECD of human TrkB is comprised of amino acid residues C32-H430 from the full length protein (which is set forth as SEQ ID NO:1, GenBank Accession No. NP_006171). Note that all protein and nucleic acid sequences that are present as of the filing date in the GenBank, SwissProt, EMBL databases or any other publicly available database are incorporated herein by reference (including without limitation the sequences of the neurotrophins, e.g., NGF, BDNF, NT-3, NT-4/5, etc.). The second immunogen is a recombinant protein that includes the extracellular domain (ECD) of murine TrkB. The ECD of murine TrkB is comprised of amino acid residues C32-H429 from the full length protein (which is set forth as SEQ ID NO:2, GenBank Accession No. P15209). Those skilled in the art will appreciate that suitable immunogens that include these domains can be prepared using standard recombinant technology (e.g., see *Protocols in Molecular Biology* Ed. by Ausubel et al., John Wiley & Sons, New York, N.Y., 1989 and *Molecular Cloning: A Laboratory Manual* Ed. by Sambrook et al., Cold Spring Harbor Press, Plainview, N.Y., 1989, the contents of which are incorporated herein by reference).

In certain embodiments, the first and second immunogens are administered in a ratio (by weight) that is greater than about 1. For example, the ratio may be about 2, 3, 4, 5, 6, 7, 8, 9, 10 or more. In one embodiment the ratio is greater than about 5. In one embodiment the ratio is about 10. In one embodiment the first and second immunogens are administered simultaneously as a mixture.

In one embodiment, one or both immunogens include versions of their respective extracellular domains that differ slightly from the naturally-occurring domains. For example, amino acids at the N- or C-terminus of the extracellular domain may be missing. Alternatively a few amino acids within the naturally-occurring sequence may be mutated. Preferably these mutations are conservative substitutions. It is to be understood that these non-naturally occurring versions should include an amino acid sequence that is at least 95%, preferably at least 96%, more preferably at least 97%, yet more preferably at least 98% and even more preferably at least 99% identical to the extracellular domains that are found in SEQ ID NO:1 or SEQ ID NO:2.

In certain embodiments, the first and/or second immunogens do not include any of the amino acids that are found outside of the extracellular domain of TrkB (e.g., they do not include the amino acids that are found in transmembrane and/or intracellular domains of TrkB). In certain embodiments, the immunogens may include one or more terminal amino acids that are absent from the naturally occurring TrkB proteins. In particular, terminal amino acids may be added to increase expression of the recombinant protein, as a consequence of the vector used for expression, etc. In addition, amino acid segments that are absent from the protein allergen may be added to the amino and/or carboxyl terminus of the recombinant protein, e.g., tags for purification, labels for detection, tags that increase the solubility of the recombinant allergen, tags that increase the stability of the immunogens, fusion with an unrelated protein or adjuvant carrier protein, etc. A proteolytic cleavage site may be introduced at the junction of the added amino acid segment and the recombinant protein terminus to enable removal of the added segment after the recombinant protein has been purified, absorbed, etc. Common terminal modifications used in recombinant technology are described in *Current Protocols in Molecular Biology* Ed. by Ausubel et al., John Wiley & Sons, New York, N.Y., 1989 and *Molecular Cloning: A Laboratory Manual* Ed. by Sambrook et al., Cold Spring Harbor Press, Plainview, N.Y., 1989.

In one embodiment, the first and second immunogens have the same composition as the two immunogens that are described in the Examples and that were obtained from R&D systems, Inc. (Cat. No. 397-TR/CF and 1494-TB/CF, respectively).

In certain embodiments, the first immunogen is as described above but the second immunogen includes the extracellular domain (ECD) from a non-human TrkB species other than murine (e.g., rat, chicken, rabbit, etc.). The ECD of rat TrkB is comprised of amino acid residues C32-H429 from the full length protein (which is set forth as SEQ ID NO:3, GenBank Accession No. NP_036863). The ECD of chicken TrkB is comprised of amino acid residues C32-T428 from the full length protein (which is set forth as SEQ ID NO:4, GenBank Accession No. CAA54468).

Once suitable immunogens have been prepared, the immunogens are injected into any of a wide variety of animals (e.g., mice, rats, rabbits, etc.). In one embodiment the immunogens are injected into mice as described in the Examples. For example, the immunogens are injected subcutaneously and intraperitoneally with complete Freund's adjuvant. In certain embodiments, each animal is injected subcutaneously at multiple different sites. In this step, the recombinant proteins may serve as immunogens without further modification. Alternatively, a superior immune response may be elicited if the recombinant proteins are joined to an adjuvant carrier protein, such as bovine serum albumin or keyhole limpet hemocyanin (KLH). The immunogens are injected into the animal host, preferably according to a predetermined schedule incorporating one or more booster immunizations and the animals are bled periodically. For example, in certain embodiments, one or more booster immunizations are administered intravenously. Binding between immune sera and the first (and optionally the second) immunogen is then optionally assessed to confirm that a suitable titer of antibodies has been raised.

Monoclonal antibodies that are specific for one or both of the immunogens may be prepared by any standard method. For example, the technique of Kohler and Milstein, *Eur. J. Immunol.* 6:511, 1976 and improvements thereto may be used. Briefly, these methods generally involve the preparation of immortal cell lines capable of producing antibodies having the desired specificity. Such cell lines may be produced, for example, from spleen cells obtained from one or more animals immunized as described above. The spleen cells are then immortalized by, for example, fusion with a myeloma cell fusion partner, preferably one that is syngeneic with the immunized animal. In certain embodiments animals with suitable sera are boosted one or more times with the first and/or second immunogen before the spleen cells are removed. A variety of fusion techniques may be employed. For example, the spleen cells and myeloma cells may be combined with a nonionic detergent for a few minutes and then plated at low density on a selective medium that supports the growth of hybrid cells, but not myeloma cells. A certain selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the first (and optionally the second) immunogen as described below.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a murine. Monoclonal antibodies may then be harvested from the ascites fluid or the blood. Contaminants may be removed from the antibodies by conventional techniques, such as chromatography, gel filtration, precipitation and extraction. The antibody isotypes can be determined using standard methods. As discussed in the Examples and shown in Table 1, we have prepared specific murine antibodies belonging to isotypes IgG1, IgG2a and IgG2b using these methods.

3. Characterization of Antibody Binding

In certain embodiments, inventive antibodies are characterized for their binding activities to human TrkB (e.g., using ELISA and/or FACS as described in the Examples). In certain embodiments binding to human TrkB proteins that are expressed on a cell surface may also be assessed (e.g., using HEK293 cells as described in the Examples). Preferably, inventive antibodies are also tested for their cross-species binding activity (e.g., with the second immunogen). This allows monoclonal antibodies that bind TrkB from both species to be identified. These antibodies are of interest since they can be tested in animal models with the knowledge that they can also be applied in human clinical trials.

In certain embodiments it may prove advantageous to further characterize the binding properties of any given monoclonal antibody. In particular, one may use a competition assay (e.g., an ELISA) to determine whether the antibodies block the interaction of TrkB and BDNF. One may also assess whether the antibodies bind non-human TrkB and/or human TrkA or TrkC.

Mapping of the relative antibody binding epitopes on TrkB (human or other) may also be conducted, e.g., by examining the activity of each individual antibody in blocking the binding of other antibodies to TrkB. For example, the observation that two antibodies block each other's binding suggests these antibodies may bind to the same epitope or overlapping epitopes on TrkB.

4. Characterization of Antibody Function

In certain embodiments, inventive antibodies are characterized for their functional ability to activate human TrkB. Any agonist assay may be used. The Examples describe an exemplary luciferase assay that has been shown to selectively represent the activation of TrkB. TrkB autophosphorylation (e.g., as measured by Western blot) can also be used as a measure of TrkB activation.

Alternatively or additionally, the human TrkB agonist activity of the inventive antibodies can be assessed in an assay that involves endogenous TrkB (e.g., in human neuroblastoma SY5Y cells). As described in the Examples, such assays test for the ability of each antibody to promote neurite growth or to increase survival of differentiated cells following injury (e.g., serum withdrawal injury). In certain embodiments the dose-dependent effects of the inventive antibodies on neurite growth and/or cell viability are measured.

In certain embodiments the purified monoclonal antibodies are also characterized for their functional ability to activate non-human TrkB (e.g., murine, rat, chicken, rabbit, etc.). The Examples describe an assay in which the antibodies were tested in rat cerebellar granule neuron (CGN) cultures for activity against the endogenous rat TrkB receptor. As with the human cells a neurite outgrowth assay and a neuroprotection assay can be performed. Other useful assays are known in the art and will be recognized by those skilled in the art.

In yet other embodiments and as described in the Examples, the purified monoclonal antibodies are further characterized for their functional ability to activate human TrkA and/or TrkC.

5. Humanized and Veneered Antibodies

When using an inventive antibody for therapeutic purposes it may prove advantageous to use a humanized or veneered version of the antibody of interest to reduce any potential immunogenic reaction. In general, humanized or veneered antibodies minimize unwanted immunological responses that limit the duration and effectiveness of therapeutic applications of non-human antibodies in human recipients.

A number of methods for preparing humanized antibodies comprising an antigen binding portion derived from a non-human antibody have been described in the art. In particular, antibodies with rodent variable regions and their associated complementarity-determining regions (CDRs) fused to human constant domains have been described (e.g., see Winter et al., *Nature* 349:293, 1991; Lobuglio et al., *Proc. Nat. Acad. Sci. USA* 86:4220, 1989; Shaw et al., *J. Immunol.* 138:4534, 1987; and Brown et al., *Cancer Res.* 47:3577, 1987). Rodent CDRs grafted into a human supporting framework region (FR) prior to fusion with an appropriate human antibody constant domain (e.g., see Riechmann et al., *Nature* 332:323, 1988; Verhoeyen et al., *Science* 239:1534, 1988; and Jones et al. *Nature* 321:522, 1986) and rodent CDRs supported by recombinantly veneered rodent FRs have also been described (e.g., see EPO Patent Pub. No. 519,596).

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes (e.g., see Lonberg and Huszar *Int. Rev. Immunol.* 13:65-93, 1995 and U.S. Pat. Nos. 5,545,806; 5,569,825; 5,625,126; 5,633,425; and 5,661,016).

Veneered versions of the inventive antibodies may also be used in the methods of the present invention. The process of veneering involves selectively replacing FR residues from, e.g., a murine heavy or light chain variable region, with human FR residues in order to provide an antibody that comprises an antigen binding portion which retains substantially all of the native FR protein folding structure. Veneering techniques are based on the understanding that the antigen binding characteristics of an antigen binding portion are determined primarily by the structure and relative disposition of the heavy and light chain CDR sets within the antigen-association surface (e.g., see Davies et al., *Ann. Rev. Biochem.* 59:439, 1990). Thus, antigen association specificity can be preserved in a humanized antibody only wherein the CDR structures, their interaction with each other and their interaction with the rest of the variable region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

6. Single-Chain Antibodies

Single chain antibodies can also be prepared based on the inventive antibodies. For example, a single-chain antibody (scFv) can be engineered as described in, for example, Colcher et al., *Ann. N Y Acad. Sci.* 880:263-80, 1999; and Reiter, *Clin. Cancer Res.* 2:245-52, 1996. Specific methods are described in the Examples. The single-chain antibody can be dimerized or multimerized to generate multivalent antibodies having specificities for different epitopes of human TrkB.

7. Pharmaceutical Compositions

Monoclonal antibodies of the invention may be administered neat in order to activate TrkB in accordance with the present invention. More commonly, however, they are administered in the context of a pharmaceutical composition, that contains a therapeutically effective amount of one or more antibodies together with one or more other ingredients known to those skilled in the art for formulating pharmaceutical compositions.

As used herein, the terms "pharmaceutically effective amount" or "therapeutically effective amount" mean the total amount of each active ingredient of the pharmaceutical composition or method that is sufficient to show a meaningful patient benefit, i.e., treatment, prevention or amelioration of a condition which requires TrkB activation. When applied to an individual active ingredient that is administered alone, the term refers to that ingredient alone. When applied to a combination of active ingredients, the term refers to combined amounts of the active ingredients that result in the therapeutic effect, whether administered in combination, serially or simultaneously.

In certain embodiments of the invention, inventive antibodies are administered with a weekly dose in the range of about 0.1 to about 1000 mg/kg body weight, or about 1 to about 500 mg/kg body weight, in certain embodiments about 10 to about 300 mg/kg body weight. Doses may be administered as a single regimen or as a continuous regimen divided by two or more doses over the course of a day or week. Delivery may be as a bolus or in certain embodiments as a gradual infusion (e.g., by injection over 30 mins). In certain embodiments one or more higher doses (e.g., 2, 3 or 4 fold higher) may be administered initially followed by one or more lower maintenance doses. The higher dose(s) may be administered at the onset of treatment only or at the beginning of each treatment cycle. These dosage levels and other dosage levels herein are for intravenous or intraperitoneal administration. The skilled person will readily be able to determine the dosage levels required for a different route of administration. It will be appreciated that, in general, the precise dose used will be as determined by the prescribing physician and will depend not only on the weight of the subject and the route of administration, but also on the age of the subject and the severity of the symptoms.

Additional ingredients useful in preparing pharmaceutical compositions in accordance with the present invention include, for example, carriers (e.g., in liquid or solid form), flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof.

Liquid pharmaceutical compositions preferably contain one or more monoclonal antibodies of the invention and one or more liquid carriers to form solutions, suspensions, emulsions, syrups, elixirs, or pressurized compositions. Pharmaceutically acceptable liquid carriers include, for example water, organic solvents, pharmaceutically acceptable oils or fat, or combinations thereof. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators, or combinations thereof. If the liquid formulation is intended for pediatric use, it is generally desirable to avoid inclusion of alcohol.

Examples of liquid carriers suitable for oral or parenteral administration include water (preferably containing additives such as cellulose derivatives such as sodium carboxymethyl cellulose), alcohols or their derivatives (including monohydric alcohols or polyhydric alcohols such as glycols) or oils (e.g., fractionated coconut oil and arachis oil). For parenteral administration the carrier can also be an oily ester such as ethyl oleate and isopropyl myristate. The liquid carrier for pressurized compositions can be halogenated hydrocarbons or other pharmaceutically acceptable propellant.

Solid pharmaceutical compositions preferably contain one or more solid carriers, and optionally one or more other additives such as flavoring agents, lubricants, solubilizers, suspending agents, fillers, glidants, compression aids, binders or tablet-disintegrating agents or an encapsulating material. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier is preferably a finely divided solid which is in admixture with the finely divided active ingredient. In tablets, the active ingredient(s) are generally mixed with a carrier having the necessary compression properties in suitable proportions, and optionally, other additives, and compacted into the desired shape and size.

In some embodiments of the invention, pharmaceutical compositions are provided in unit dosage form, such as tablets or capsules. In such form, the composition is sub-divided in unit dose containing appropriate quantities of the active ingredient(s). The unit dosage forms can be packaged compositions, for example packeted powders, vials, ampoules, pre-filled syringes or sachets containing liquids. The unit dosage form can be, for example, a capsule or tablet itself, or it can be an appropriate number of any such compositions in package form.

Thus, the present invention also provides a pharmaceutical composition in unit dosage form for activating TrkB, where the composition contains a therapeutically effective unit dosage of at least one monoclonal antibody of the invention. As one skilled in the art will recognize, the certain therapeutically effective unit dosage will depend on the method of administration.

The present invention also provides a therapeutic package for dispensing the monoclonal antibodies of the invention to an individual being treated for a condition which requires TrkB activation. In some embodiments, the therapeutic package contains one or more unit dosages of at least one inventive monoclonal antibody, a container containing the one or more unit dosages, and labeling directing the use of the package for treatment. In certain embodiments, the unit dose is in tablet or capsule form. In some cases, each unit dosage is a therapeutically effective amount.

8. Other Pharmaceutical Agents

According to the present invention, monoclonal antibodies of the invention may be administered alone to modulate TrkB activity. Alternatively the antibodies may be administered in combination with (whether simultaneously or sequentially) one or more other pharmaceutical agents useful in the treatment, prevention or amelioration of one or more other conditions (including symptoms, disorders, or diseases) which require TrkB activity.

For example, other pharmaceutical agents that can modulate TrkB activity may be used in combination with the monoclonal antibodies of the invention, including other activators of TrkB. U.S. Pat. Nos. 5,770,577; 6,077,829; 6,723,701 and 6,800,607 (each incorporated herein by reference in their entirety) describe BDNF derivatives and compositions that may be useful in accordance with the practice of the present invention.

Additionally or alternatively, the monoclonal antibodies may be used in conjunction with other pharmaceutical agents that are useful in the treatment, prevention or amelioration of neurological disorders and diseases. In certain embodiments, the monoclonal antibodies are combined with agents that are useful in the treatment, prevention or amelioration of disorders and diseases caused by injuries to the nervous system (e.g., by wound, surgery, ischemia, infection, metabolic diseases, malnutrition, malignant tumor, toxic drugs, etc.). It is to be understood that any suitable agent known in the art may be used, including those listed in the Physicians' Desk Reference, 55$^{th}$ Edition, 2001, published by Medical Economics Company, Inc. at Monvale, N.J., the relevant portions of which are incorporated herein by reference.

9. Therapeutic Uses

In one aspect, inventive antibodies are Useful for treating conditions (including symptoms, disorders, or diseases) which require activation of TrkB. Such methods involve administering a therapeutically effective amount of one or more inventive antibodies to the individual. In certain embodiments, the invention provides methods for treating neurological conditions. For example, and without limitation, inventive antibodies may be used to treat individuals with a nervous system that has been injured by wound, surgery, ischemia, infection, metabolic diseases, malnutrition, malignant tumor, toxic drug, etc. Specific examples include stroke, spinal cord injury, traumatic brain injury, retinal degeneration and axotomy. The inventive antibodies may also be used to treat disorders such as attention-deficit hyperactivity disorder (ADHD), depression and age-associated mental impairment (i.e., by providing cognitive enhancement). The inventive antibodies may also be used to treat congenital or neurodegenerative conditions including Alzheimer's disease, Parkinson's disease, Huntington's chorea, amyotrophic lateral sclerosis (ALS) and conditions related to these. The benefits of TrkB activation in treating non-neurological diseases such as cancer and diabetes has also been described and the inventive antibodies may therefore find utility in such contexts (e.g., U.S. Pat. Nos. 5,877,016 and 6,800,607 describe the benefits of TrkB activation for treating cancer and diabetes, respectively).

The methods of this invention are useful for treating the conditions described herein in adults and children. They may also be utilized for veterinary applications, particularly including canine and feline applications. If desired, the methods herein may also be used with farm animals, such as ovine, bovine, porcine and equine breeds.

Inventive methods involve delivery of inventive monoclonal antibodies via any appropriate route of administration including, for example, parenteral, intravenous, topical, nasal, oral (including buccal or sublingual), rectal or other modes. In general, the antibodies may be formulated for immediate, delayed, modified, sustained, pulsed, or controlled-release delivery.

In certain embodiments, the antibodies are formulated for delivery by injection. In such embodiments, administration may be, for example, intracavernous, intravenous, intra-arterial, intraperitoneal, intrathecal, intraventricular, intraurethral, intrasternal, intracranial, intramuscular or subcutaneous, or via by infusion or needleless injection techniques. For such parenteral administration, the antibodies of the invention may be prepared and maintained in conventional lyophylized formulations and reconstituted prior to administration with a pharmaceutically acceptable saline solution, such as a 0.9% saline solution. The pH of the injectable formulation can be adjusted, as is known in the art, with a pharmaceutically acceptable acid, such as methanesulfonic acid. Other acceptable vehicles and solvents that may be employed include Ringer's solution and U.S.P. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the inventive antibody, it may be desirable to slow its absorption from an intramuscular or subcutaneous injection. Delayed absorption of such an administered antibody may be accomplished by dissolving or suspending the agent in an oil vehicle. Injectable depot forms are made by forming microencapsule matrices of the antibody in biodegradable polymers such as polylactide-polyglycolide. Depending upon the ratio of antibody to polymer and the nature of the particular polymer employed, the rate of antibody release can be controlled. Examples of other biodegradable polymers include poly(orthoesters) and poly(anhydrides). Depot injectable formulations are also prepared by entrapping the antibodies in liposomes or microemulsions which are compatible with body tissues.

For application topically to the skin, the antibodies can be formulated as a suitable ointment containing the active ingredient suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The inventive antibodies can also be administered intranasally or by inhalation and are conveniently delivered in the form of a dry powder inhaler or an aerosol spray presentation from a pressurized container, pump, spray, atomiser or nebuliser, with or without the use of a suitable propellant, e.g. dichlorodifluoromethane, trichlorofluoromethane, dichlorotetrafluoroethane, a hydrofluoroalkane, carbon dioxide or other suitable gas. In the case of a pressurized aerosol, the dosage unit may be determined by providing a valve to deliver a metered amount. The pressurized container, pump, spray, atomiser or nebuliser may contain a solution or suspension of the antibody, e.g., using a mixture of ethanol and the propellant as the solvent, which may additionally contain a lubricant, e.g., sorbitan trioleate. Capsules and cartridges (made, for example, from gelatin) for use in an inhaler or insufflator may be formulated to contain a powder mix of the antibodies of the invention and a suitable powder base such as lactose or starch.

For inventive methods utilizing oral delivery, such delivery may be accomplished using solid or liquid formulations, for example in the form of tablets, capsules, multi-particulates, gels, films, ovules, elixirs, solutions or suspensions. In certain embodiments, the monoclonal antibodies are administered as oral tablets or capsules. Such preparations may be mixed chewable or liquid formulations or food materials or liquids if desirable, for example to facilitate administration to children, to individuals whose ability to swallow tablets is compromised, or to animals.

Compositions for rectal administration are preferably suppositories which can be prepared by mixing the inventive antibodies with suitable non-irritating excipients or carriers such as cocoa butter, polyethylene glycol or a suppository wax which are solid at ambient temperature but liquid at body temperature and therefore melt in the rectal vault and release the antibodies. Retention enemas and rectal catheters can also be used as is known in the art. Viscosity-enhancing carriers such as hydroxypropyl cellulose are also certain carriers of the invention for rectal administration since they facilitate retention of the pharmaceutical composition within the rectum. Generally, the volume of carrier that is added to the pharmaceutical composition is selected in order to maximize retention of the composition. In particular, the volume should not be so large as to jeopardize retention of the administered composition in the rectal vault.

10. Diagnostic Uses

In another aspect, inventive antibodies may be used for detecting TrkB in a sample (e.g., in order to diagnose a disorder characterized by over or under expression of TrkB). According to such methods an inventive antibody is combined with a sample under conditions to allow specific binding. The specific binding is then detected thereby indicating the presence of TrkB in the sample.

The sample can be derived from a body fluid (e.g., from cerebrospinal fluid, blood, serum, urine, etc.) or an extract of cells or tissue (e.g., a biopsy sample). Detection of binding can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$ or $^{3}H$.

A variety of protocols for measuring antibody binding, including ELISA and FACS, are known in the art and provide a basis for diagnosing altered or abnormal levels of TrkB expression. ELISA and FACS are further described in the Examples. Normal or standard values for TrkB expression are established by combining samples taken from normal individuals with an inventive antibody under conditions suitable for complex formation. The amount of standard complex formation may be quantified by various methods depending on the nature of the detectable substance. Preferably the amount of standard complex formation is quantified by photometric means. Levels of TrkB expression in samples from diseased individuals are then compared with the standard values. Deviation between standard and diseased values establishes the parameters for diagnosing disease.

In certain embodiments, the inventive methods may be used to diagnose neurological conditions that are characterized by over or under expression of TrkB. For example, and without limitation, inventive methods may be used to identify nervous systems that have been injured by wound, surgery, ischemia, infection, metabolic diseases, malnutrition, malignant tumor, toxic drug, etc. Specific examples include stroke, spinal cord injury, traumatic brain injury, retinal degeneration and axotomy. The inventive methods may also be used to diagnose disorders such as attention-deficit hyperactivity disorder (ADHD), depression and age-associated mental impairment (i.e., by providing cognitive enhancement). The inventive methods may also be used to diagnose congenital or neurodegenerative conditions including Alzheimer's disease, Parkinson's disease, Huntington's chorea, amyotrophic lateral sclerosis (ALS) and conditions related to these.

11. Purification Uses

The invention also provides a method of using an antibody to purify TrkB from a sample comprising combining an inventive antibody with a sample under conditions to allow specific binding, thereby producing an antibody-TrkB receptor complex, separating the antibody-TrkB receptor complex from the remainder of the sample and then separating the antibody from the TrkB receptor, thereby obtaining a purified TrkB receptor. It will be appreciated that the inventive antibodies can be used to isolate TrkB by any standard technique, such as affinity chromatography or immunoprecipitation.

EXAMPLES

The present invention is further illustrated and supported by the following examples. However, these examples should in no way be considered to further limit the scope of the invention. To the contrary, one having ordinary skill in the art would readily understand that there are other embodiments, modifications, and equivalents of the present invention without departing from the spirit of the present invention and/or the scope of the appended claims.

Example 1

This example describes the preparation and in vitro characterization and testing of a plurality of TrkB antibodies.

Materials and Methods

Immunogens

Murine anti-TrkB antibodies were prepared using a mixture of two protein immunogens: a first recombinant protein that includes the extracellular domain (ECD) of human TrkB (rhTrkB-ECD) (R&D systems, Inc., Cat. No. 397-TR/CF) and a second recombinant protein that includes the extracellular domain of murine TrkB (rmTrkB-ECD) (R&D system, Inc., Cat. No. 1494-TB/CF).

The extracellular domain of human TrkB is comprised of amino acid residues C32-H430 of the full length protein (which is set forth as SEQ ID NO:1, GenBank Accession No. NP_006171). rhTrkB-ECD was expressed in murine myeloma cell line NSO. The calculated molecular mass of monomeric rhTrkB-ECD is 44 kDa; however, when glycosylated it migrates as a broad band of 80-100 kDa in SDS-PAGE under reducing conditions.

The extracellular domain of murine TrkB is comprised of amino acid residues C32-H429 of the full length protein (which is set forth as SEQ ID NO:2, GenBank Accession No. P15209). In the mhTrkB-ECD used for this Example, this sequence is flanked by an N-terminal human CD33 signal peptide which is cleaved during expression and a C-terminal His Tag. rhTrkB-ECD was also expressed in murine myeloma cell line NSO. The calculated molecular mass of the monomeric mhTrkB-ECD is 45.9 kDa; however, when glycosylated it migrates as a broad band of 75-100 kDa in SDS-PAGE under reducing conditions.

Immunization Schedules

Five 8-week old female BALB/c mice were immunized with 10 μg of rhTrkB-ECD that was pre-mixed with complete Freund's adjuvant (CFA). The mixture was separated into portions that were injected subcutaneously and intraperitoneally 4 times biweekly (i.e., at weeks 0, 2, 4, and 6). The mice were also immunized at week 7 by subcutaneous and intraperitoneal injection with 1 μg of rmTrkB-ECD that was pre-mixed with complete Freund's adjuvant (CFA). Mice bleeds were collected at weeks 5 and 7 and antibody responses in the sera were evaluated.

Generation of Murine Anti-TrkB Monoclonal Antibodies (mAbs)

Three of the five mice were additionally boosted intravenously with 10 μg rhTrkB and 1 μg rmTrkB 3 days prior to the cell fusion (which occurred at week 12). Splenocytes from these three mice were fused with murine myeloma cells P3X63Ag8.653 (ATCC, Cat. No. CRL-1580) at 4:1 ratio using 50% polyethylene glycol (MW 1500) (Roche Diagnostics Corp., Cat. No. 783641). After fusion, cells were seeded and cultured in 96-well plates at $1 \times 10^5$ cells/well in selection medium (RPMI1640 containing 20% FBS and 5% Origen) (IGEN International, Inc., Cat. No. 210001), 2 mM L-glutamine, 100 U/ml penicillin, 100 μg/ml streptomycin, 1×HEPES and 1×HAT (hypoxanthine-aminopterin-thymidine) (Sigma, Cat. No. H0262). Hybridoma supernatants were screened for binding with rhTrkB by ELISA and staining on rhTrkB-expressing HEK293 stable cells by FACS analysis (see below). The hybridoma supernatants selected to be positive were subsequently tested for agonist activities on rhTrkB using a luciferase assay (see below). Selected hybridomas were subcloned four times by serial dilutions and once by FACS sorting (see below). Conditional medium was harvested from the stable hybridoma culture. Prosep-A (Montage Antibody Purification Spin columns, Millipore, Cat. No. P36486) was used to purify IgG from the hybridoma conditional medium. The Ig class of each mAb was determined with a murine mAb isotyping kit (IsoStrip, Boehringer Mannheim Corp., Cat. No. 1493027).

ELISAs

To measure the presence of TrkB-specific antibodies, 96-well plates (Maxisorp, Nunc) were coated with 1 μg/ml rhTrkB-EDC-Fc (R&D system, Cat. No. 688-TK) or rmTrkB-Fc (R&D system) and incubated overnight at 4° C. After washing the plates and blocking the wells with PBS (10 mM sodium phosphate, 150 mM NaCl, pH 7.2) containing 1% BSA and 0.05% Tween-20, 100 μl of diluted immune serum or hybridoma supernatants were added and incubated for 1 hr at room temperature. The plates were washed, and the bound anti-TrkB antibodies were detected using peroxidase conjugated goat anti-murine IgG (H+L) (PIERCE, Cat. No. 31434) followed by incubation with the substrate TMB (BioFX Laboratories, Cat. No. TMBW_1000-01). The absorbance values were determined at 450 nm in a spectrophotometer.

To determine the mAb concentration in the hybridoma supernatant, 96-well plates were coated with 1 μg/ml goat anti-murine IgG (Fcγ) (PIERCE, Cat. No. 31123) in PBS and incubated overnight at 4° C. After washing and blocking the wells with PBS containing 1% BSA and 0.05% Tween-20, 100 μl of diluted hybridoma supernatants were added for 1 hr at room temperature. Purified isotype-matching murine IgG was used as a standard for the quantification of anti-TrkB IgG concentrations. The plates were washed, and HRP labeled goat anti-murine IgG-Fc were added and incubated for 1 hr at room temperature. After washing the wells, the substrate TMB was added. Absorbance was determined at 450 nm.

Characterization of Relative Antibody Binding Epitopes using Competition Binding To determine how the binding of anti-TrkB IgG to TrkB protein affects the BDNF interaction with TrkB, a 96-well plate was coated with 0.3 μg/ml of BDNF (R&D system, Cat. No. 248-BD/CF) in PBS and incubated overnight at 4° C. After washing and blocking the wells with PBS containing 1% BSA and 0.05% Tween-20, 100 μl of pre-incubated hybridoma supernatant (or diluted immune serum) mixture with rhTrkB-EDC-Fc was added to the plate and incubated for 1 hr at room temperature. After washing the plate, peroxidase conjugated goat anti-human IgG, (Fcγ) (PIERCE, Cat. No. 31416) was added and incubated for 1 hr at room temperature. The wells were washed and the substrate TMB was added. Absorbance was determined at 450 nm.

To map the relative antibody binding epitopes on rhTrkB, a 96-well plate was coated with 1 μg/ml of each individual TrkB-specific mAb in PBS and incubated overnight at 4° C. After washing and blocking the wells with PBS containing 1% BSA and 0.05% Tween-20, 100 μl of mixture of each individual pre-incubated TrkB mAb (20 μg/ml) and rhTrkB-EDC-Fc (0.1 μg/ml) was added to the wells and incubated for 1 hr at room temperature. The plate was washed and incubated for 1 hr with peroxidase conjugated goat ant-human IgG, (Fcγ). After washing the plate, the substrate TMB was added. Absorbance was determined at 450 nm.

Luciferase Assay

A stable line of HEK-293 cells expressing rhTrkB was generated by transfecting HEK-293 cells with pcDNA-hTrkB (full length, see GenBank Accession No. NM_006180). Transfected cells were selected in the presence of hygromycin for 2 wks with limited dilutions. Following initial evaluation, a single clone of cells was chosen for the study. For the luciferase assay, cells were plated at $1.5 \times 10^4$ cells/well in 100 μl growth medium in 96-well plates. The next day, cells were treated with 10 of 10× final concentration of BDNF or test antibodies. Luciferase activities were measured 16 hr after the treatments using the Promega Steady-Glo assay kit according to the manufacturer's protocol. In brief, media was replaced with 100 μl of PBS and 100 μl of Steady-Glo reagent was added. After sealing the plates with TopSeal, the plates were shaken at Titer Plate Shaker at speed ~5 for 5 minutes and then luminescence was measured using a TopCount NXT v2.13 instrument (Packard).

FACS Analysis

HEK-293 cells expressing rhTrkB were detached from the plates with PBS containing 5 mM EDTA and transferred in to 5 ml Falcon tubes (Becton Dickinson, Cat. No. 352063) with $2 \times 10^5$ cells per tube. Cells were washed once with PBS by centrifuging at 800 rpm at 4° C. for 3 min, and incubated for 30 min at 4° C. with 100 μl of hybridoma culture supernatant, purified antibodies or immune serum diluted in PBS with 1% FBS. The cells were washed 3 times with 1 ml PBS containing 1% FBS and incubated for 30 min at 4° C. in the dark with PE labeled goat anti-murine IgG, F(ab')$_2$ fragment (DAKO Corporation, Cat. No. R0480) in PBS containing 1% FBS. Cells were washed three times again and re-suspended in 250 μl PBS containing 1% FBS. Popidium iodide was used for detection of dead cells, which were excluded from analysis. The fluorescence of 5000 cells/tube was counted by a FAC-Scan flow cytofluorometer (Becton Dickinson).

TrkB Autophosphorylation Assay

HEK-293 cells expressing rhTrkB were plated in 24 well plates at $2 \times 10^5$ cells/well in a DMEM growth media. The next day, cells were incubated in serum-free DMEM for 90 min, then stimulated with BDNF or testing antibodies at different concentrations for 30 min at 37° C. After washing with PBS once, cells were lysed in Laemmli Sample Buffer (Bio-Rad) preheated at 95° C. Lysates were run through QIAshredder column (Qiagen) and 20 μl of samples were resolved on 4-12% Bis-Tris gel (Invitrogen). Following transfer to nitrocellulose membranes, phosphorylated TrkB bands were detected using PY490 phospho-Trk-specific antibody (1:100, Cell Signaling, Cat. No. 9141) followed by incubation with HRP-conjugated anti-rabbit secondary antibody (Molecular Probes). The signals were developed using ECL plus kit (Amersham).

Neurite Outgrowth Assay

Human neuroblastoma SH-SY5Y cells were grown in DMEM:F12(1:1) supplemented with 2 mM L-glutamine, 15% FBS and pen/strep. For the neurite outgrowth assay, cells were plated in 96 well tissue culture plates at the density of $4 \times 10^3$ cells/well and incubated with 10 μM all-trans-retinoic acid (RA) to induce neuronal differentiation. On the third day, the media was replaced with fresh growth media with or without BDNF or testing antibodies, as indicated in the results. After three additional days in culture, cells were fixed by IC-Fix for 30 min at room temperature and further processed for immunostaining of beta-Tubulin III. First, cells were permeabilized by brief incubation in 0.2% Triton in phosphate-buffered solution (TPBS). Then samples were incubated in 1.5% normal goat serum (NGS) in TPBS for 30 min to block non-specific binding, followed by incubation with anti-beta-Tubulin III mAb (Tuj1, 1:1000, Covance) in 1.5% NGS/TPBS. Tuj1 signals were detected using Alexa 488 murine anti-goat antibody (1:500, Molecular Probes) and neurite outgrowth was analyzed using Cellomics arrayscan.

For the measurement of neurite promoting effects in the primary neurons, rat or murine cerebellar granular neuron (CGN) cultures were prepared. Briefly, the cerebellum was dissected from animals postnatal day 7 and cut into small pieces. The tissue was treated with papain (Worthington Biochemical Corp.) for 30 min at 37° C. and dispersed by gentle trituration. Following centrifugation at 300 g for 5 min, dissociated cells were reconstituted in Neurobasal medium containing B27 supplement, 0.5 mM 1-glutamine, and 25 mM potassium chloride and plated in 96 well Biocoat plates precoated with poly-d-lysin (BD bioscience) at a density of $1.2 \times 10^4$ cells/well. Cells were treated with BDNF or testing antibodies for 24 hrs, fixed with IC-Fix for 30 min at room temperature and processed for Tuj1 immunostaining as described above.

Cell Survival Assay

SH-SY5Y cells were plated in 96 well plates at $1 \times 10^4$ cells/well and incubated with RA (10 μM) to induce neuronal differentiation. After 3 days, the culture media was switched to growth media without serum (serum-free media) and cells were treated with BDNF, testing antibodies or vehicle. Following two additional days in culture, cell viability was measured by MTT assay using the CellTiter 96 Non-Radioactive Cell Proliferation Assay Kit (Promega) according to the manufacturer's protocol.

Neuroprotection Assay

Rat or murine CGN cultures were prepared from 7 day-old pups as described above and plated in 96 well Biocoat plates precoated with poly-d-lysin (BD bioscience) at a density of $7.3 \times 10^4$ cells/well. 24 hrs after plating, cells were subjected to potassium serum deprivation (KSD) injury, which is known to result in significant death of cerebellar granular neurons. Sister cultures were co-treated with BDNF or testing antibodies. Following 24 hr incubation, cell viability was measured using a CellTiter 96 Non-Radioactive Cell Proliferation Assay Kit (Promega).

Results

Evaluation of Antibody Responses from TrkB Immunized Mice

Figure 1B:
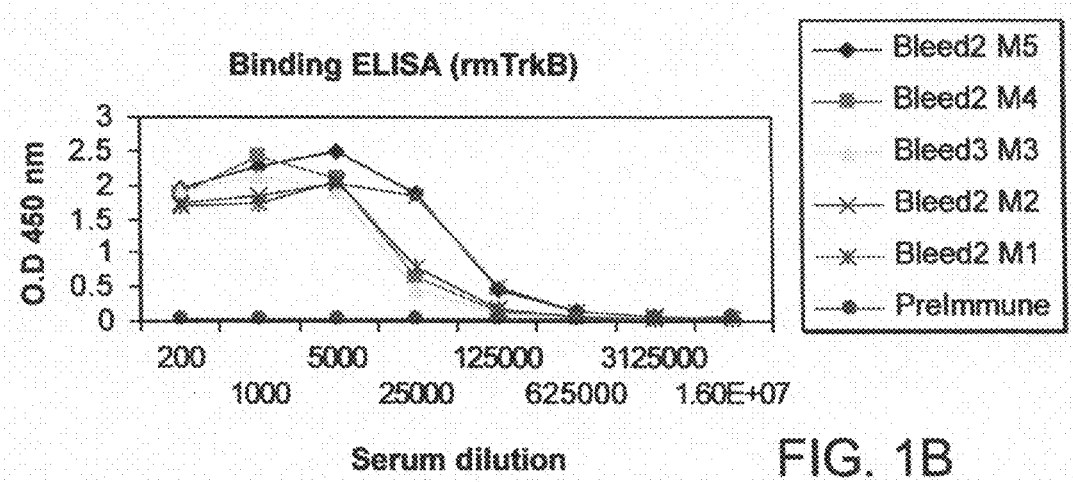
Figure 1C:
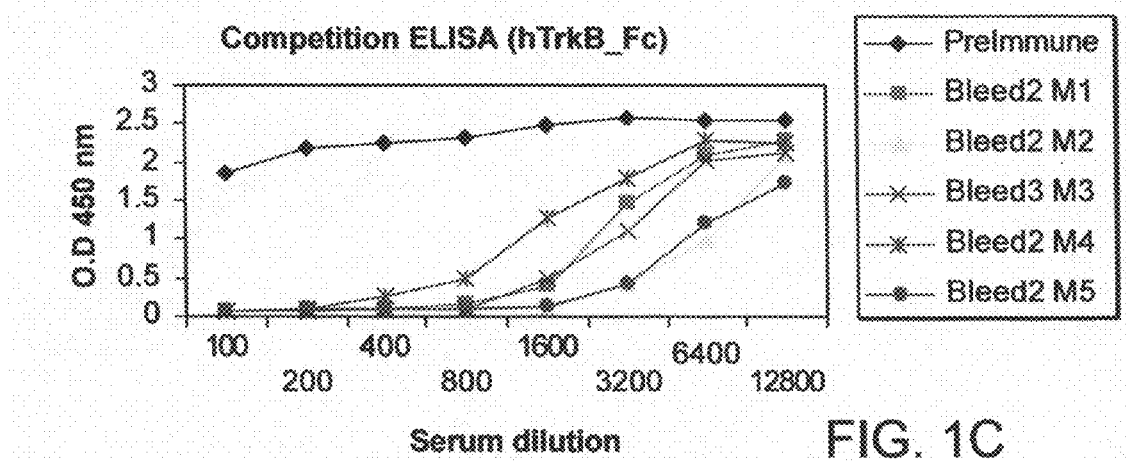
Figures 1, 1D, 2:
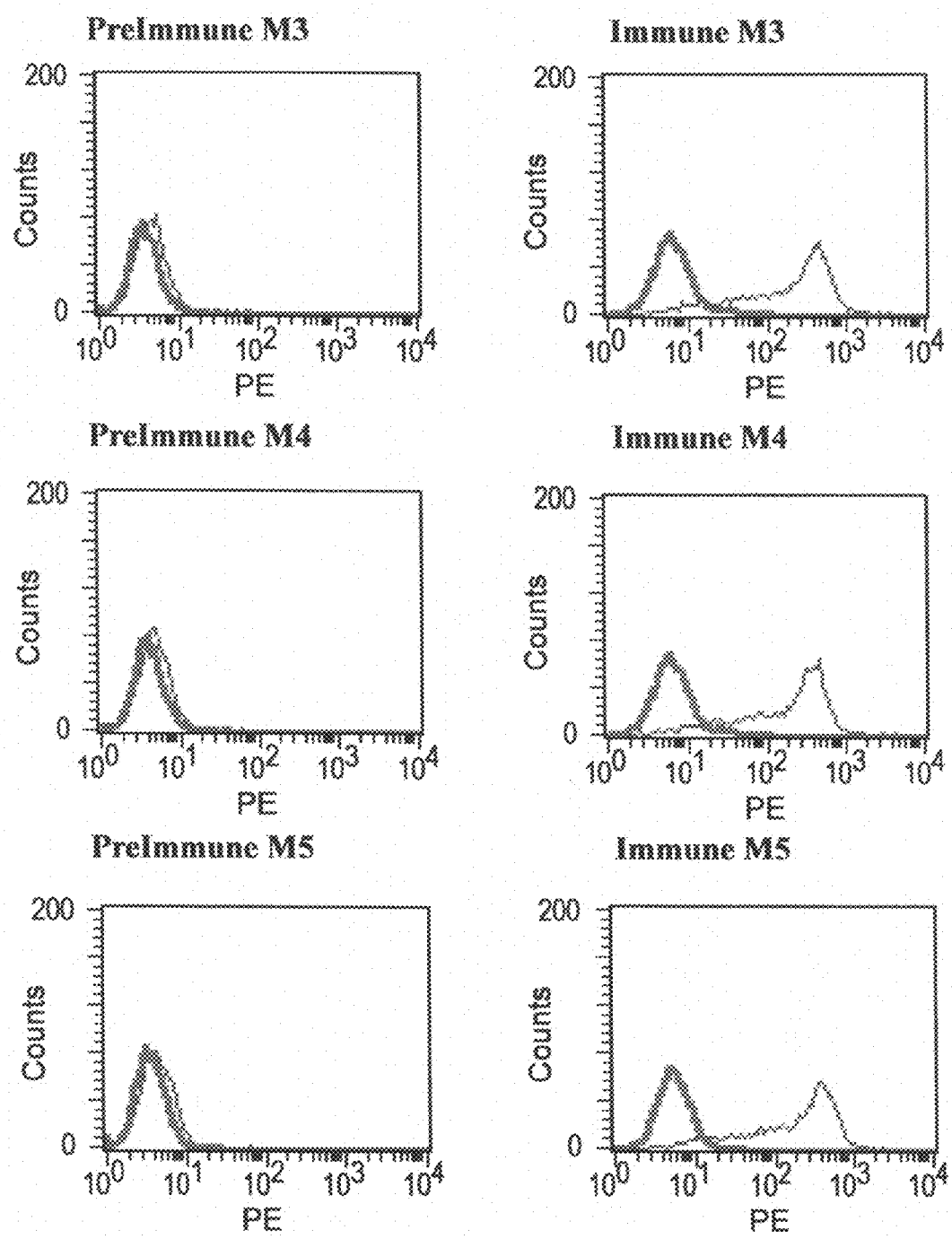
Figure 2A:
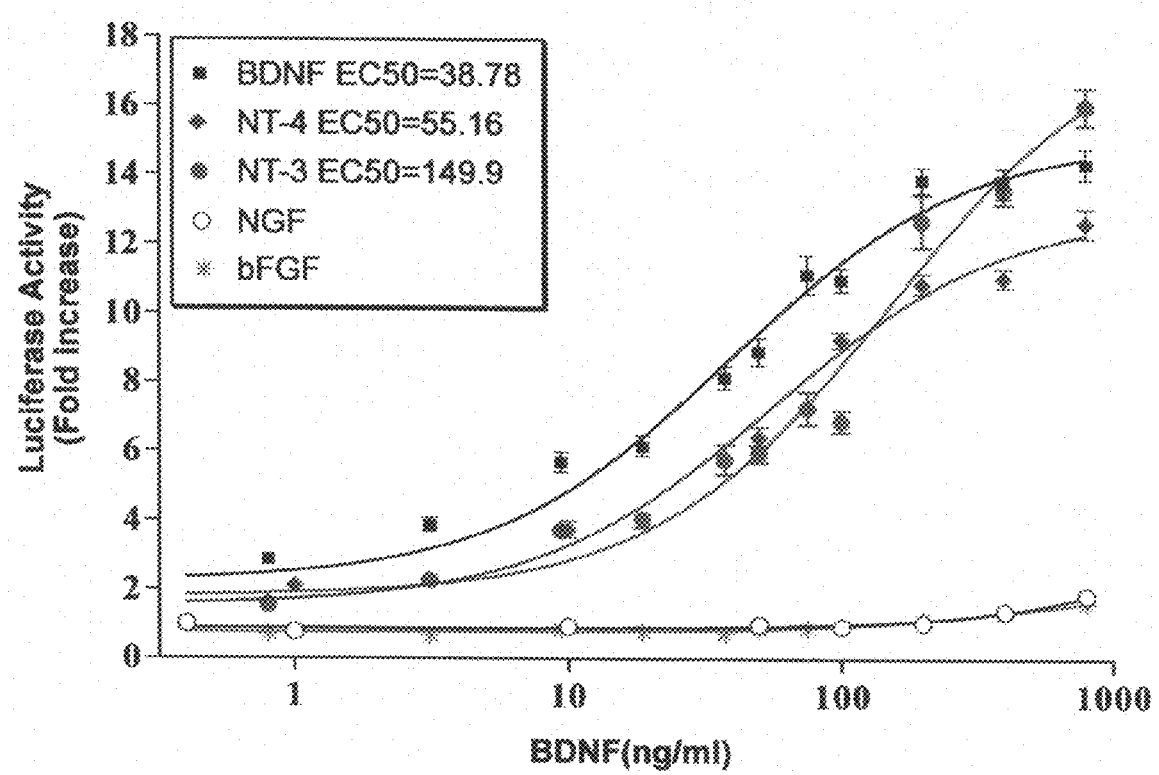
FIGS. 2A and 2B depict control results that were obtained with neurotrophins in a luciferase activity assay that uses HEK-293 cells which express surface rhTrkB. These control results show that the assay can selectively represent the activation of TrkB.
Figure 2B:
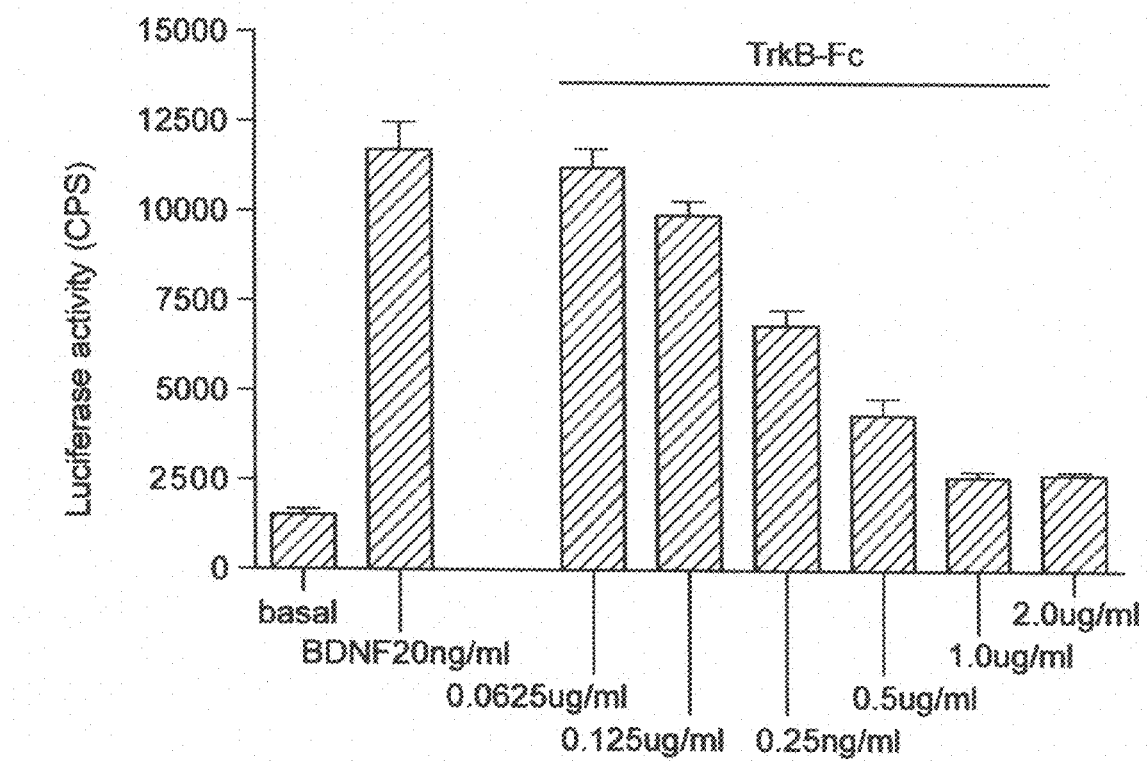

To evaluate the specific immune responses to TrkB, the five immunized mice (M1-M5) were bled one week following the third and fourth immunizations. High anti-TrkB antibody titers in the serum were determined by ELISA and FACS analysis in both the third and the fourth bleeds. FIG. 1 represents results from the bleeds after the fourth immunization. All five mice generated high titers recognizing both rhTrkB-ECD and rmTrkB-ECD in ELISA (FIGS. 1A and 1B).

The location of antibody binding epitopes on hTrkB relative to the BDNF binding site was also evaluated. Results from competition ELISA showed that the immune bleeds can block rhTrkB-EDC-Fc and BDNF interactions in an order of M2=M5>M3>M4=M1 (FIG. 1C). Interestingly, the efficacies of antibodies in blocking the rhTrkB-BDNF interaction correlated with the antibody binding titers (compare FIGS. 1A and 1C). All immune bleeds were also shown to bind to cell surface expressed rhTrkB on HEK-293 cells as demonstrated by FACS analysis (FIG. 1D).

Figure 3B:
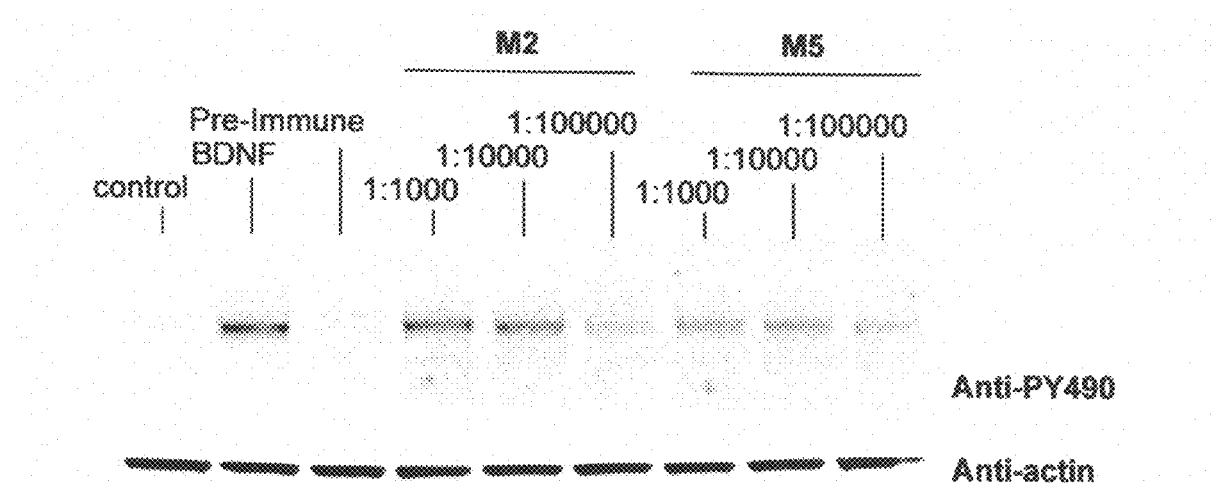
FIG. 3 depicts results that were obtained with immune sera in the same luciferase activity assay as FIG. 2 (FIG. 3A) and by anti-PY490 immunoblot analysis (FIGS. 3B and 3C). These results show that incubation of hTrkB cells with immune bleeds significantly increased the luciferase signals in a dose-dependent manner.
Figure 3C:
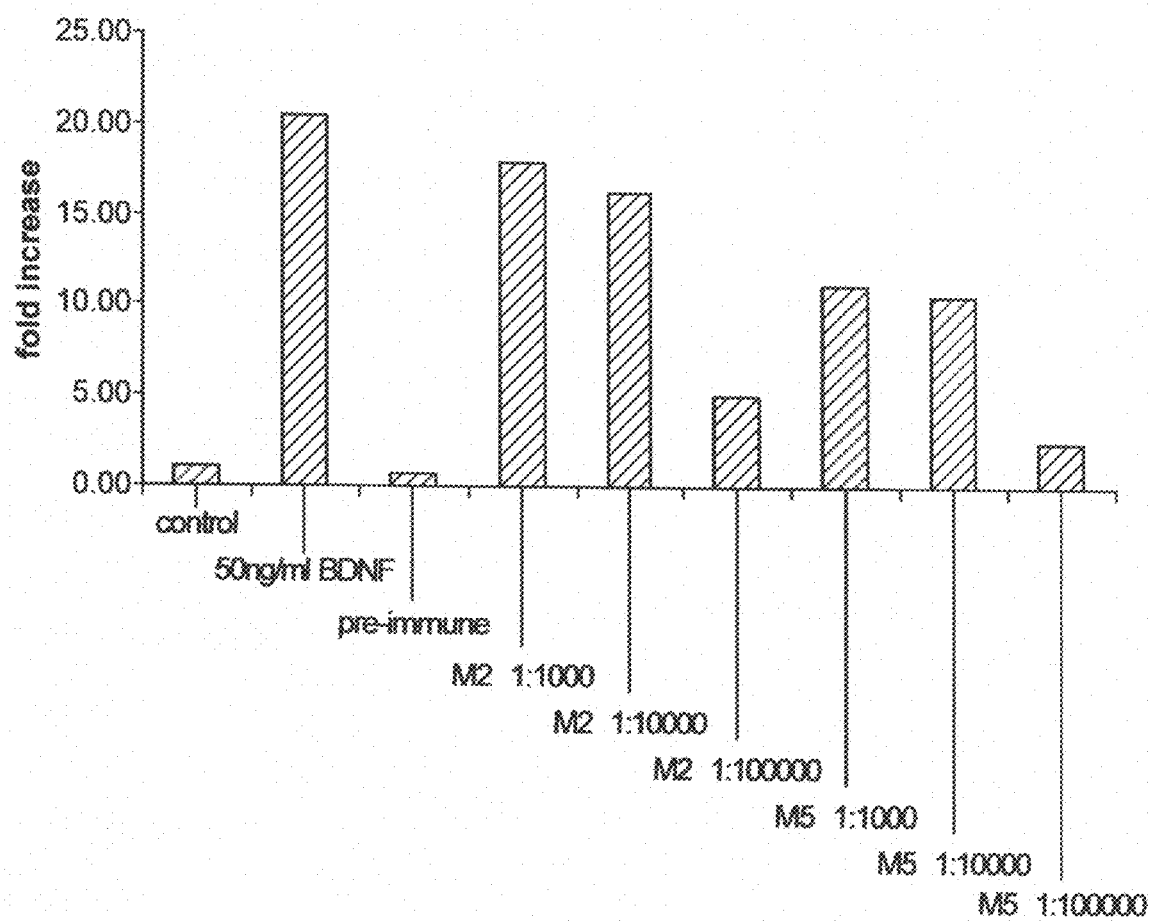

Following the observation of high titer specific binding of immune sera to hTrkB, these immune bleeds were evaluated in a luciferase reporter assay to test their agonistic activities. The luciferase activity in HEK-293 cells expressing rhTrkB has been shown to selectively represent the activation of TrkB (FIG. 2). Incubation of these cells with immune bleeds significantly increased the luciferase signals in a dose-dependent manner (FIG. 3). Again, the efficacy of agonistic activities was in an order of M2=M5>M3>M4=M1. The three mice with the highest antibody titers and robust agonist activities (M2, M3 and M5) were chosen for subsequent hybridoma generation.

Production of Monoclonal Antibodies

As described previously, the three selected mice (M2, M3 and M5) were boosted intravenously with 10 µg of rhTrkB-ECD and 1 µg of rmTrkB-ECD three days prior to the fusion. From the first round of hybridoma screening, ninety-four clones were picked up which bound strongly to rhTrkB-EDC-Fc in an ELISA assay. Twenty of these clones cross-reacted with rmTrkB-ECD in an ELISA assay. FACS analysis confirmed that fifty-four clones bound to rhTrkB expressed on the surface of HEK-293 cells.

The TrkB agonist activity of each clone was tested using a luciferase assay and seventeen hybridoma clones with highest activities were selected for further characterization. Following stabilization of these clones, three rounds of subcloning with serial dilution, and one round of subcloning with FACS sorting, the monoclonal antibodies from each culture conditional medium were collected and purified by using ProSep-A (Montage Antibody Purification Kits). The IgG isotypes of each antibody were determined by Murine Isotyping test kit (Table 1). The antibody concentrations were determined by Murine IgG quantification ELISA and all seventeen clones produced good levels of Ig in the culture supernatants.

TABLE 1

| mAb | Murine IgG Isotype | Ig concentration (µg/ml) |
| --- | --- | --- |
| 2E8 | IgG2b, k | 14 |
| 4C7 | IgG2b, k | 8 |
| 5D8 | IgG2b, k | 28 |
| 5E11 | IgG2b, k | 55 |
| 6D5 | IgG2b, k | 26 |
| 6E2 | IgG2b, k | 18 |
| 6E6 | IgG2b, k | 14 |
| 7E1 | IgG2b, k | 26 |
| 7F5 | IgG2b, k | 16 |
| 11E1 | IgG1, k | 20 |
| 16E11 | IgG2b, k | 5 |
| 17D11 | IgG1, k | 22 |
| 18C3 | IgG1, k | 18 |
| 19E12 | IgG2a, k | 10 |
| 29D7 | IgG1, k | 52 |

Characterization of Monoclonal Antibodies

The purified TrkB-specific monoclonal antibodies were characterized for their binding activities to hTrkB by ELISA. Most of the antibodies bound to rhTrkB with high binding affinities ($ED_{50}=10^{-11}$ (M)), except for a clone 29D7, for which the $ED_{50}$ dropped from $10^{-11}$ (M) to $10^{-10}$ (M) after purification (data not shown). Two clones 12F4 and 18C8 lost their binding activities after purification and were therefore deselected from the priority list (and thus were not included in Table 1). Using FACS analyses, all of the fifteen remaining TrkB binding mAbs were also shown to specifically bind to hTrkB expressed on the surface of HEK293 cells. Antibodies were also tested for their cross-species binding activities to rmTrkB by ELISA. While most of the antibodies were found to bind rmTrkB weakly, clones 17D11, 18C3 and 29D7 were found to bind rmTrkB with $ED_{50}=10^{-10\sim-11}$ (M) (Table 2).

A competition ELISA assay was used to determine whether the antibodies block the interaction of rhTrkB and BDNF. Clone 29D7 showed no blocking activity, while clones 17D11, 18C3 and 19E12 partially blocked rhTrkB-BDNF interaction. All of the other clones blocked rhTrkB-BDNF interaction with $IC_{50}=3-\times10^{-10}$ (M) (Table 2).

TABLE 2

| | Binding Activity | | Blocking activity | |
| --- | --- | --- | --- | --- |
| mAb | rhTrkB [ED$_{50}$ (nM)] | rmTrkB [ED$_{50}$ (nM)] | 293-hTrkB [Mean value] | hTrkB-BDNF [IC$_{50}$ (nM)] |
| 2E8 | 0.020 | W* | 251.88 | 0.30 |
| 4C7 | 0.017 | W* | 241.26 | 0.30 |
| 5D8 | 0.019 | W* | 247.43 | 0.30 |
| 5E11 | 0.016 | W* | 263.27 | 0.40 |
| 6D5 | 0.021 | W* | 258.74 | 0.58 |
| 6E2 | 0.016 | W* | 235.47 | 0.28 |
| 6E6 | 0.019 | W* | 246.15 | 0.40 |
| 7E1 | 0.016 | W* | 237.89 | 0.27 |
| 7F5 | 0.016 | W* | 240.03 | 0.30 |
| 11E1 | 0.020 | NB** | 117.83 | 0.30 |
| 16E11 | 0.020 | W* | 224.55 | 0.28 |
| 17D11 | 0.020 | 0.300 | 134.52 | Partial block |
| 18C3 | 0.020 | 0.300 | 132.03 | Partial block |
| 19E12 | 0.031 | W* | 194.41 | Partial block |
| 29D7 | 0.120 | 0.013 | 95.59 | No block |

W*: Weak binding
NB**: No binding

Mapping of the relative antibody binding epitopes on rhTrkB was conducted by examining the activity of each individual antibody in blocking the binding of other antibodies to rhTrkB. For example, the observation that two antibodies blocked each other's binding with rhTrkB suggests these antibodies may bind to the same epitope or overlapping epitopes on rhTrkB (Table 3). In Table 3, the pre-bound antibodies are presented in each row while the competing (i.e., coating) antibodies are presented in each column. The results showed that clones 11E1, 19E12 and 29D7 may recognize unique epitopes. Clones 17D11 and 18C3 appear to compete for the same binding site. All the remaining clones competed with each other and may share the same binding epitope.

TABLE 3

| | 2E8 | 4C7 | 5D8 | 5E11 | 6D5 | 6E2 | 6E6 | 7E1 | 7F5 | 11E1 | 16E11 | 17D11 | 18C3 | 19E12 | 29D7 | c mAb* |
| --- | --- | --- | --- | --- | --- | --- | --- | --- | --- | --- | --- | --- | --- | --- | --- | --- |
| 2E8 | + | + | + | + | + | + | + | + | + | +/− | + | − | − | − | − | − |
| 4C7 | + | + | + | + | + | + | + | + | + | +/− | + | − | − | − | − | − |
| 5D8 | + | + | + | + | + | + | + | + | + | +/− | + | − | − | − | − | − |
| 5E11 | + | + | + | + | + | + | + | + | + | +/− | + | − | − | − | − | − |
| 6D5 | + | + | + | + | + | + | + | + | + | +/− | + | − | − | − | − | − |
| 6E2 | + | + | + | + | + | + | + | + | + | +/− | + | − | − | − | − | − |
| 6E6 | + | + | + | + | + | + | + | + | + | +/− | + | − | − | − | − | − |
| 7E1 | + | + | + | + | + | + | + | + | + | +/− | + | − | − | − | − | − |
| 7F5 | + | + | + | + | + | + | + | + | + | +/− | + | − | − | − | − | − |
| 11E1 | + | + | + | + | + | + | + | + | + | + | + | − | − | − | +/− | − |
| 16E11 | + | + | + | + | + | + | + | + | + | +/− | + | − | − | − | − | − |
| 17D11 | − | − | − | − | − | − | − | − | − | − | − | + | + | +/− | − | − |

TABLE 3-continued

| | 2E8 | 4C7 | 5D8 | 5E11 | 6D5 | 6E2 | 6E6 | 7E1 | 7F5 | 11E1 | 16E11 | 17D11 | 18C3 | 19E12 | 29D7 | c mAb* |
|---|---|---|---|---|---|---|---|---|---|---|---|---|---|---|---|---|
| 18C3 | − | − | − | − | − | − | − | − | − | − | − | + | + | +/− | − | − |
| 19E12 | − | − | − | − | − | − | − | − | − | − | − | + | + | + | − | − |
| 29D7 | − | − | − | − | − | − | − | − | − | − | − | − | − | − | + | − |
| c mAb* | − | − | − | − | − | − | − | − | − | − | − | − | − | − | − | − |

+: Complete block.
+/−: Partial block.
−: No block.
c mAb*: A mixture of murine IgG1, IgG2a and IgG2b.

Luciferase Activities

Figure 4A:
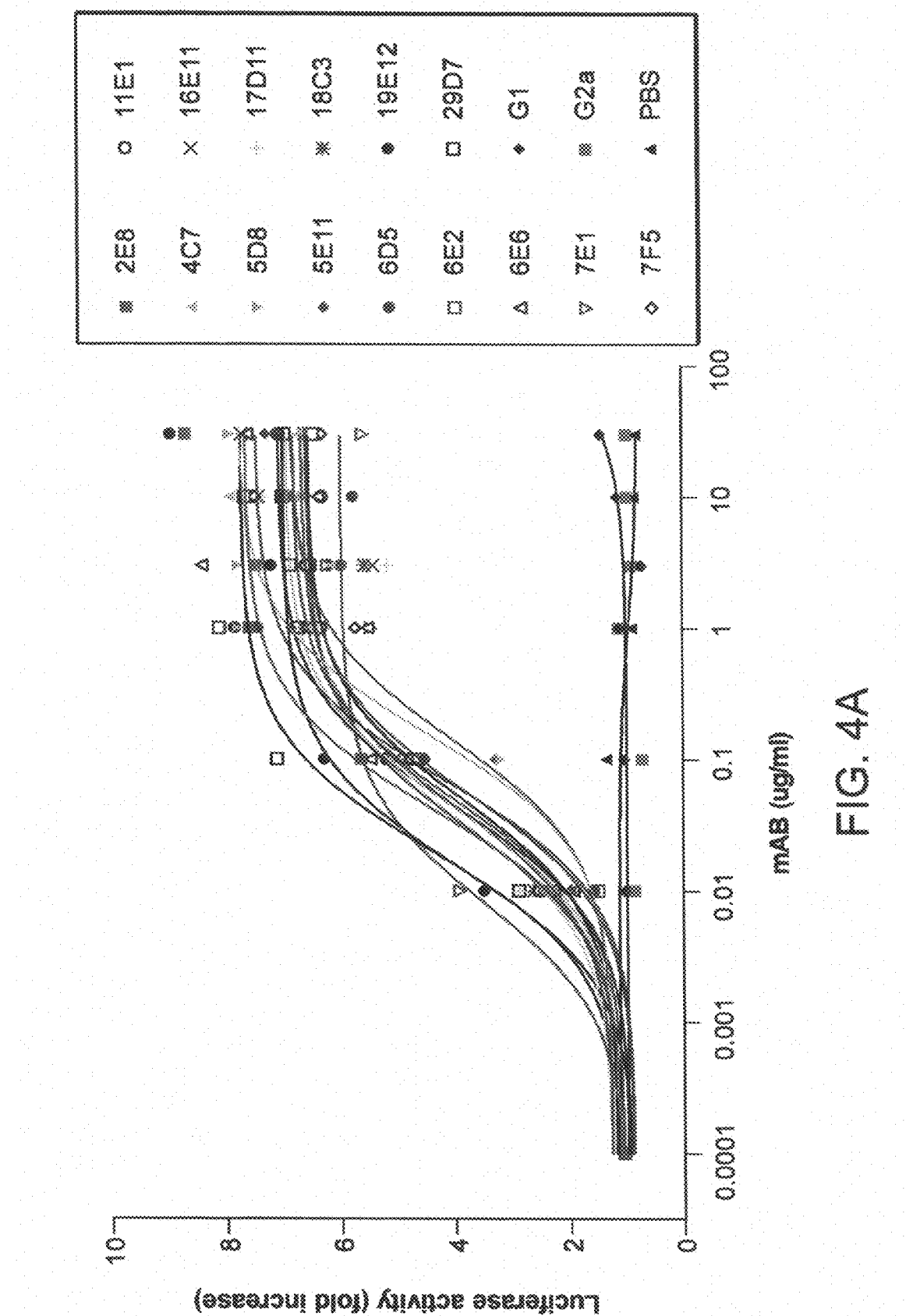
FIG. 4 depicts results that were obtained with certain TrkB antibodies in the same luciferase activity assay as FIG. 2 in graph (FIG. 4A) and table (FIG. 4B) formats. All of the antibodies caused dose-dependent increases in the signal with $EC_{50}$ in the range of $10^{-10}$ (M). The maximum signal window was ~7 fold over basal for most of the antibodies, which was comparable to the response induced by BDNF at 200 ng/ml (6.2 fold over basal).

The purified TrkB-specific antibodies were examined using a luciferase assay to demonstrate agonist activities. All of the antibodies caused dose-dependent increases in the signal with $EC_{50}$ in the range of $10^{-10}$ (M) (FIG. 4). The maximum signal window was ~7 fold over basal for most of the antibodies, which was comparable to the response induced by BDNF at 200 ng/ml (6.2 fold over basal).

Functional Activities of mAbs

Figure 5A:
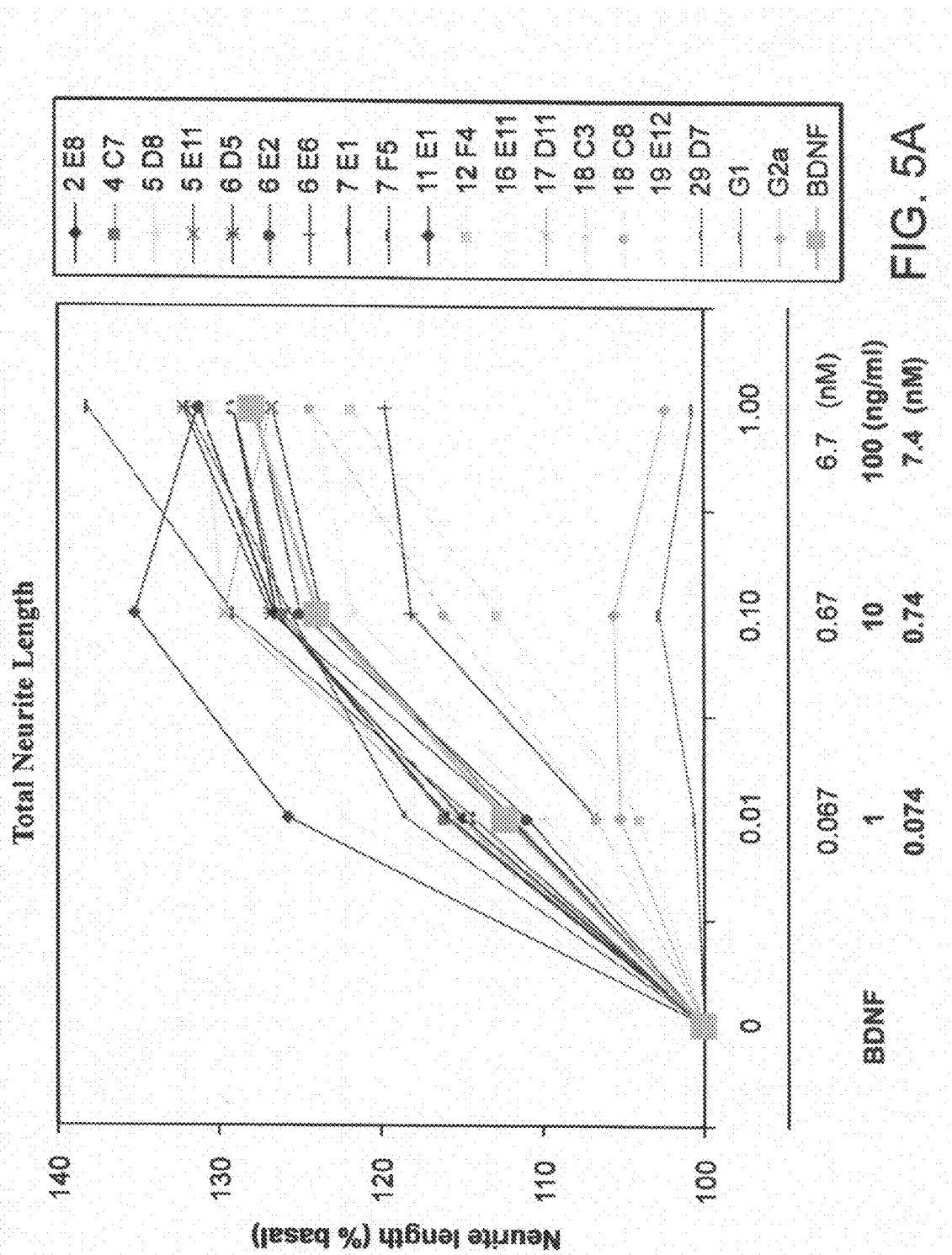
FIG. 5 depicts the results that were obtained with certain TrkB antibodies in a neurite outgrowth assay. The assay used human neuroblastoma SY5Y cells, which are known to express TrkB upon neuronal differentiation. Addition of BDNF and of most antibodies promoted neurite outgrowth as demonstrated by increases in the neurite length (FIG. 5A) and the number of branch points (FIG. 5B). Representative images of a few treatment groups are shown in (FIG. 5C). The results from full-dose response analyses obtained for a subset of these antibodies are shown in (FIG. 5D).
Figure 5B:
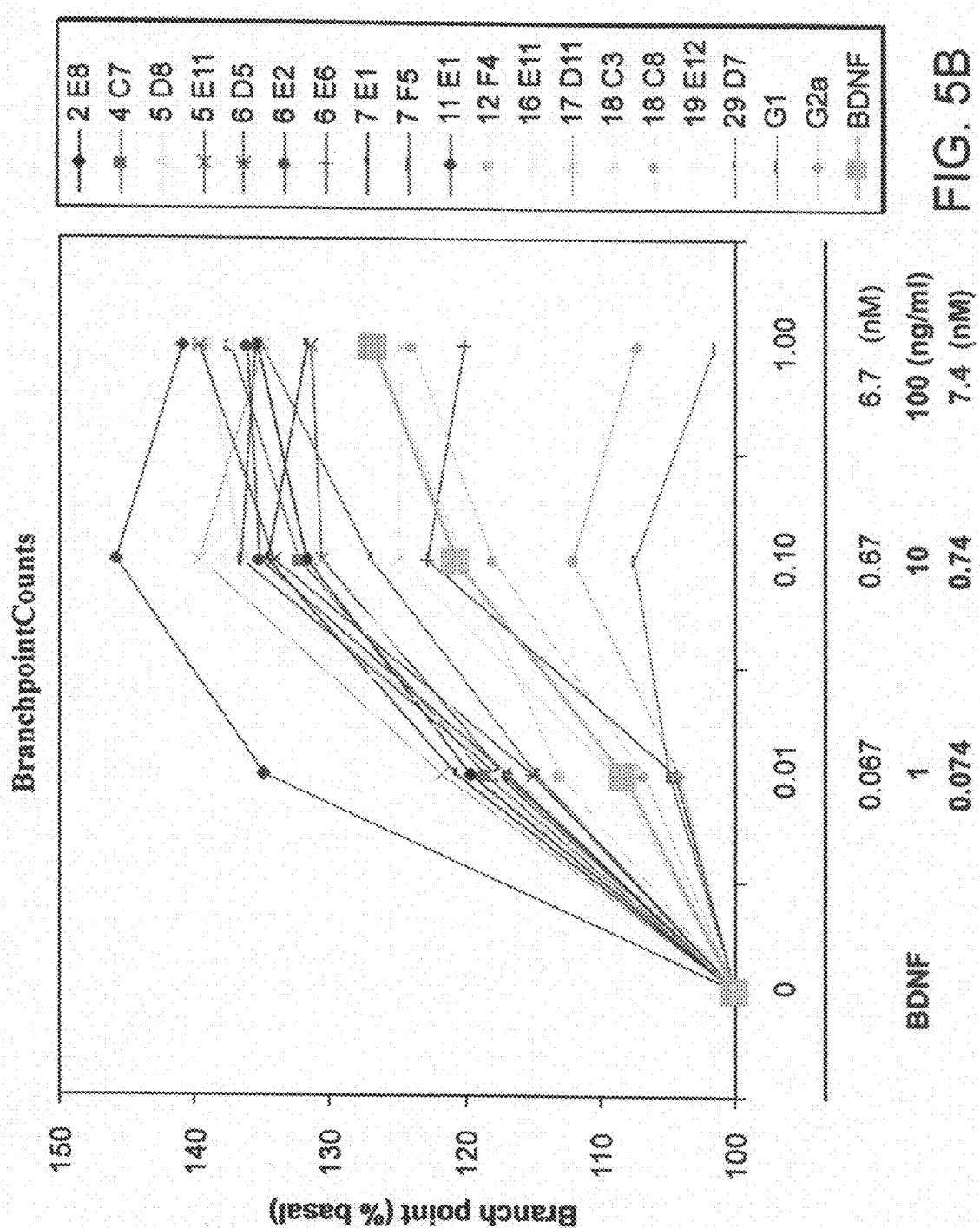
Figure 5C:
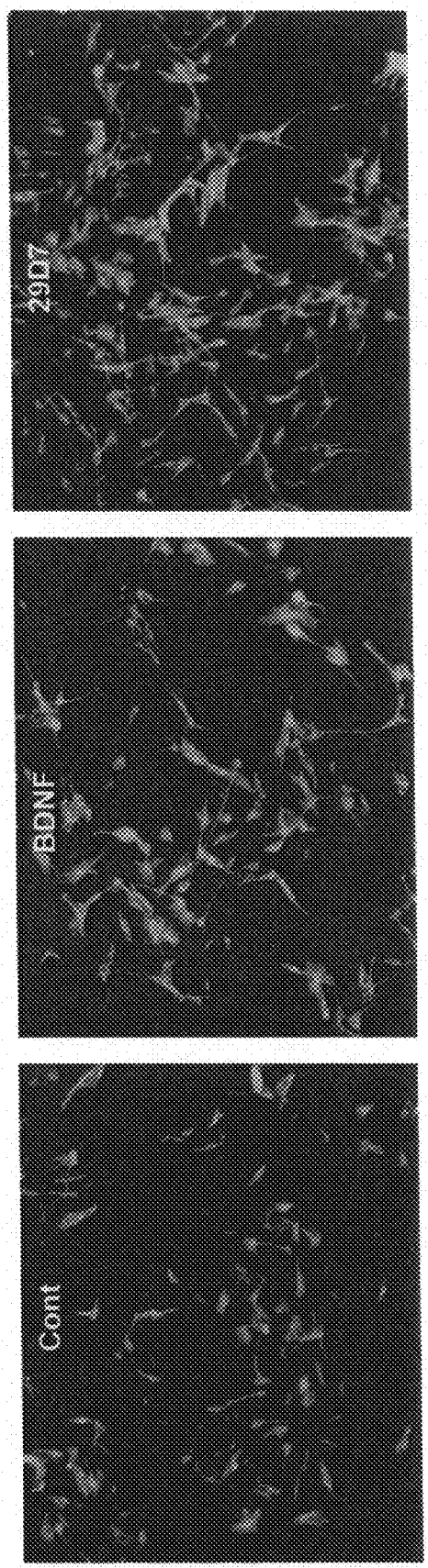

To test if the TrkB-binding antibodies have functional agonist activities mediated by endogenous TrkB receptor activation, neurite promoting effects were evaluated following treatments with these antibodies. Based on the species specific binding characteristic of the antibodies, we first utilized human neuroblastoma SY5Y cells, which are known to express TrkB upon neuronal differentiation. Consistent with previous reports, we observed that the addition of BDNF promoted neurite outgrowth as demonstrated by increases in the neurite length and the number of branch points (FIGS. 5A and 5B). Importantly, most antibodies also significantly increased neurite outgrowth with efficacies comparable or even superior to BDNF (FIGS. 5A and 5B). Examples of representative images of a few treatment groups are shown in FIG. 5C.

Figure 5D:
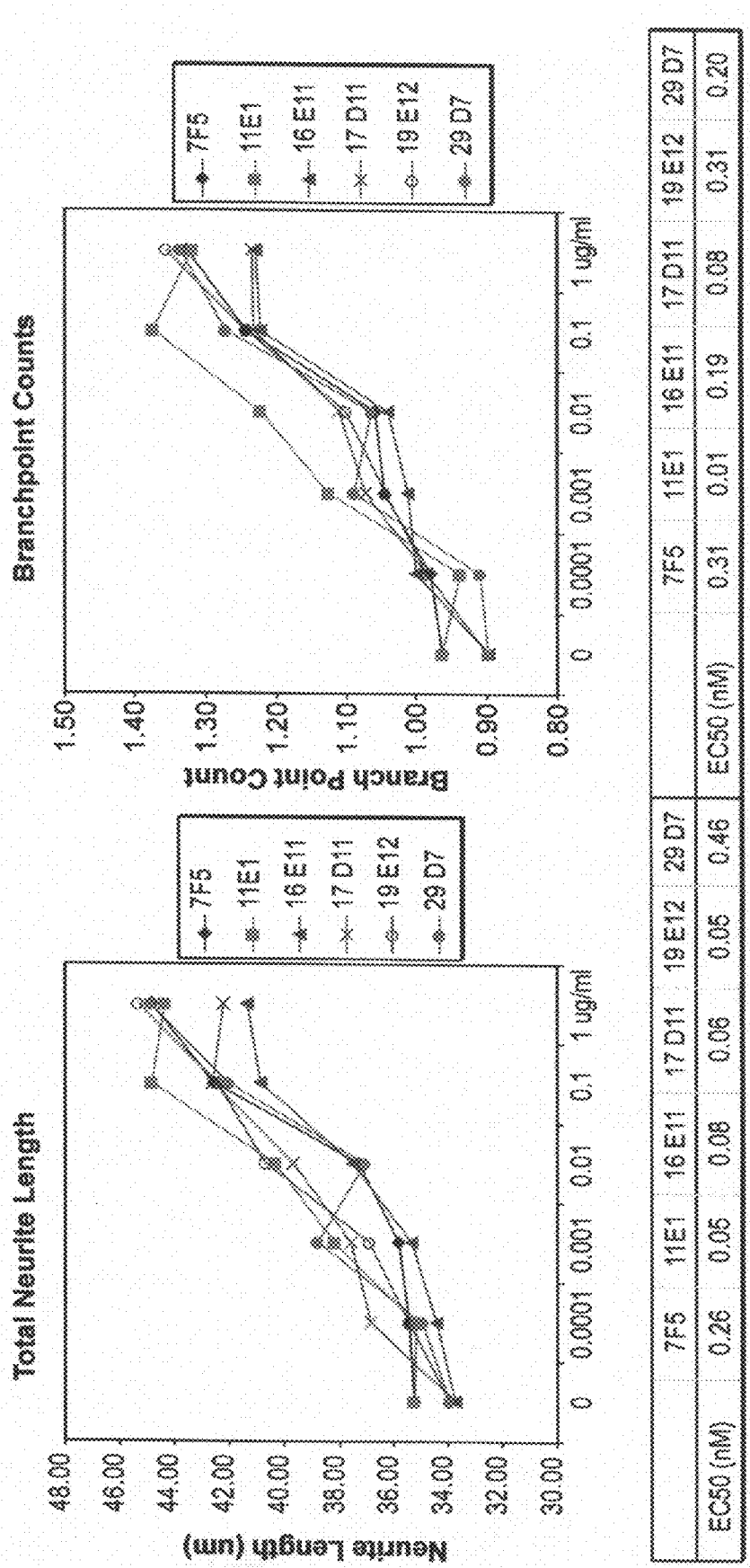
Figure 6:
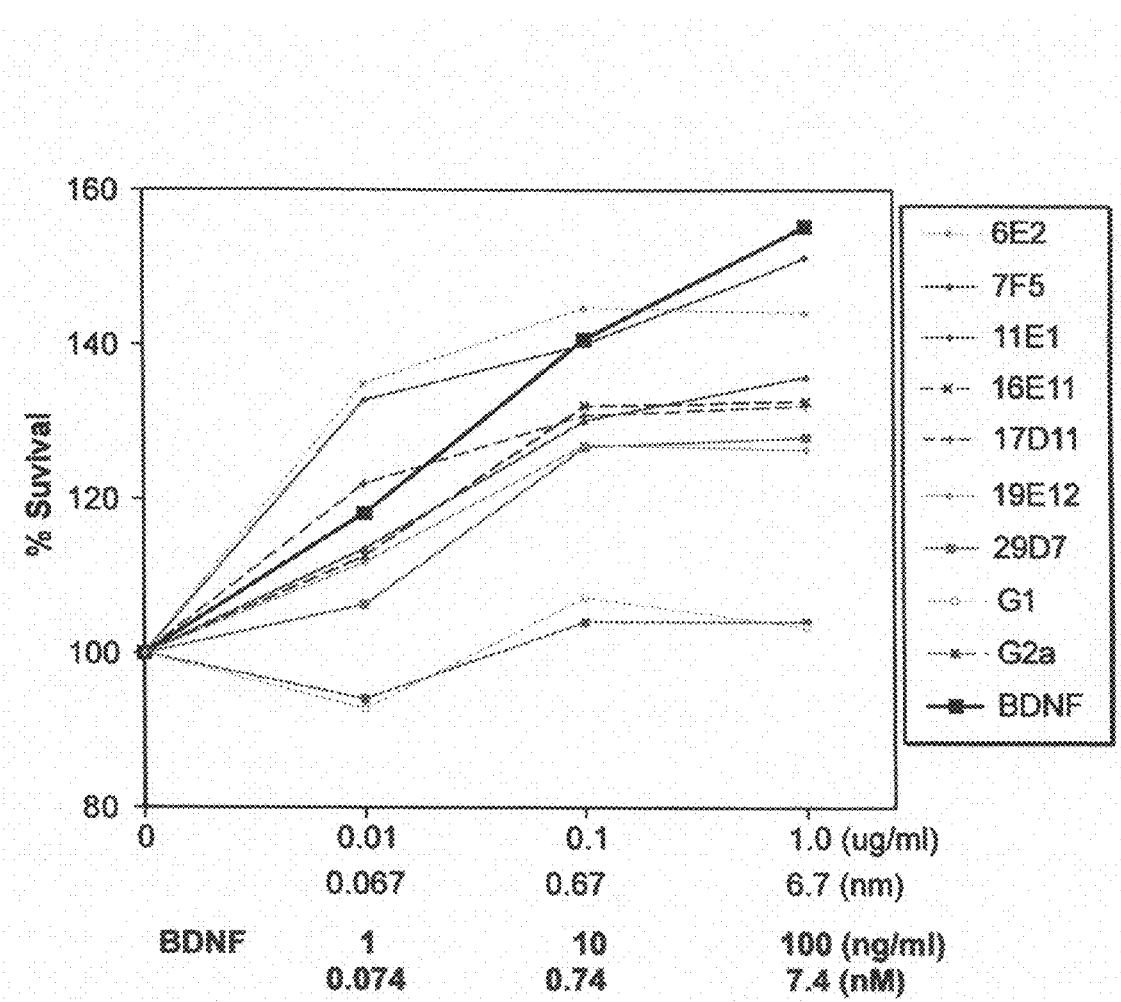
FIG. 6 depicts the results that were obtained with certain TrkB antibodies in a neuroprotection assay. The assay measures the survival of differentiated SY5Y cells following serum withdrawal injury. Results showed that BDNF and several antibodies protected differentiated SY5Y cells, demonstrating dose-dependent increases in cell viability.

Seven TrkB antibodies with highest activities (6E2, 7F5, 11E1, 16E11, 17D11, 19E12 and 29D7) were selected for full dose-response analysis. They induced dose-dependent increases in the neurite growth with $EC_{50}$ of around $10^{-10}$ (M) (FIG. 5D, data was not obtained for 6E2). These antibodies were also tested for their ability to increase survival of differentiated SY5Y cells following serum withdrawal injury. Results showed that BDNF and several antibodies protected differentiated SY5Y cells, demonstrating dose-dependent increases in cell viability (FIG. 6).

Figure 7C:
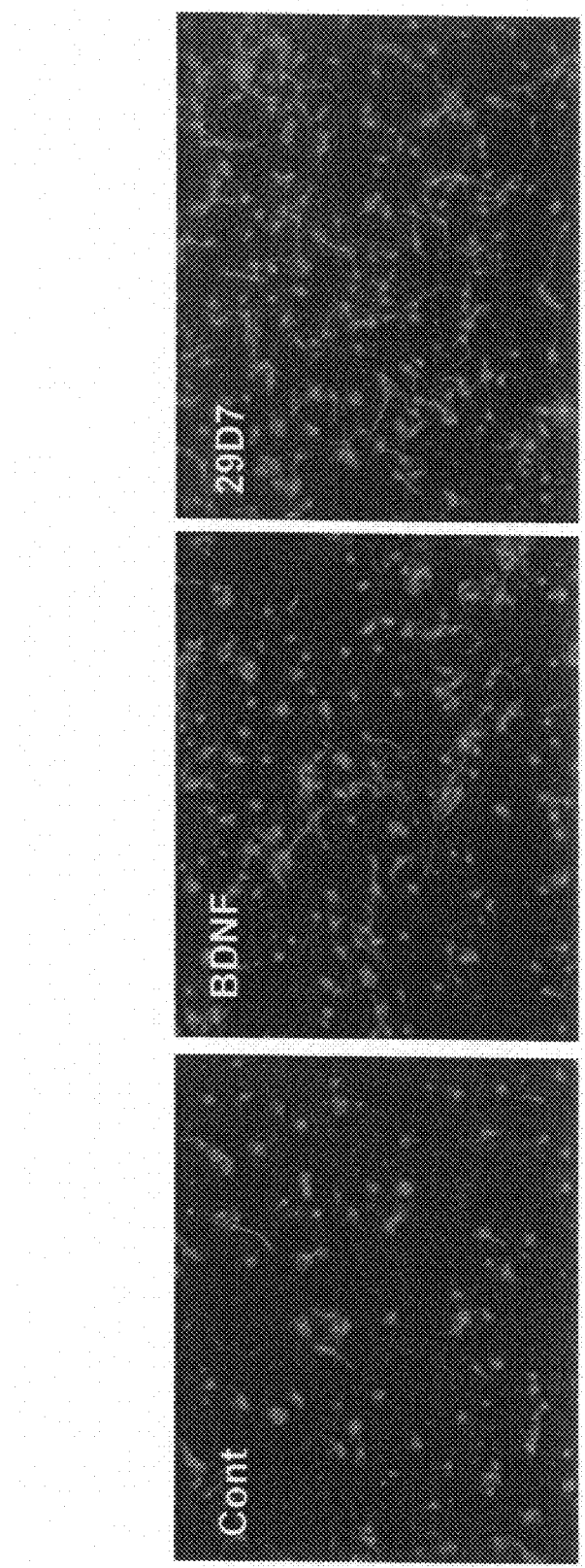
FIG. 7C shows examples of images of control cells and cells treated with BDNF or 29D7.

Two TrkB antibodies, 17D11, 18C3 and 29D7, which were shown to bind to rmTrkB, were also tested in rat cerebellar granule neuron (CGN) cultures for activity against the endogenous rat TrkB receptor. In both the neurite outgrowth assay and the neuroprotection assay, only 29D7 showed activities comparable to those of BDNF, while 17D11 and 18C3 were inactive (FIG. 7 and data not shown). It may suggest that 17D11 and 18C3 recognize an epitope on murine TrkB that contains different amino acids in rat TrkB.

TrkB Phosphorylation Analysis

Figure 8:
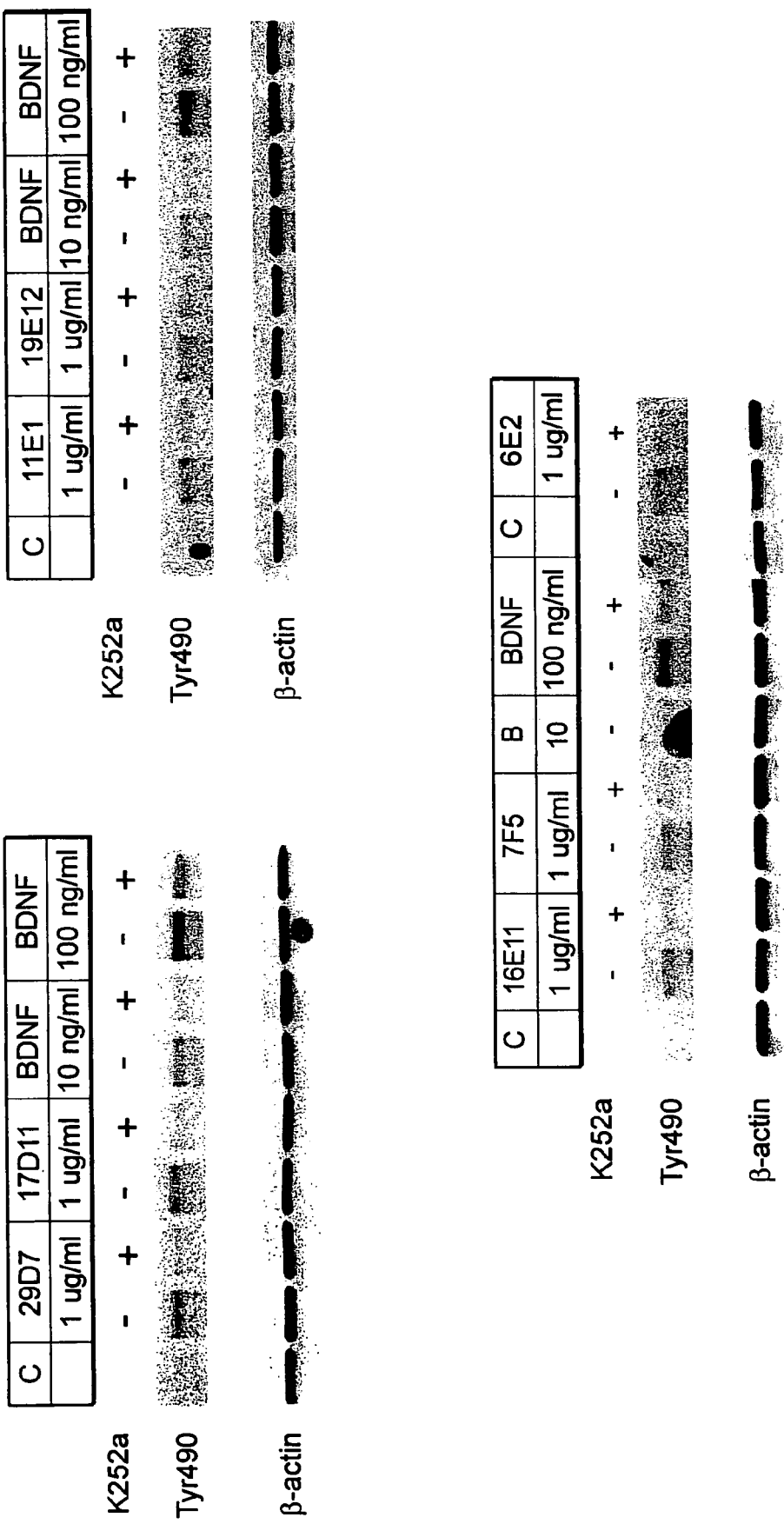
FIG. 8 depicts the results that were obtained when certain anti-TrkB antibodies were evaluated in Western analysis for induction of TrkB autophosphorylation. All antibodies led to robust TrkB phosphorylation, and these effects were antagonized by treatment with the kinase inhibitor K252a, indicating that these TrkB-binding antibodies caused activation of TrkB.

Seven TrkB antibodies (6E2, 7F5, 11E1, 16E11, 17D11, 19E12 and 29D7) selected based on all activities described above were evaluated in Western analysis for induction of TrkB autophosphorylation. All antibodies led to robust TrkB phosphorylation, and these effects were antagonized by treatment with the kinase inhibitor K252a, indicating that these TrkB-binding antibodies caused activation of TrkB (FIG. 8).

Two TrkB antibodies, 17D11, 18C3 and 29D7, which were shown to bind to rmTrkB, were also tested in rat cerebellar granule neuron (CGN) cultures for activity against the endogenous rat TrkB receptor. In both the neurite outgrowth assay and the neuroprotection assay, only 29D7 showed activities comparable to those of BDNF, while 17D11 and 18C3 were inactive (FIG. 7 and data not shown). It may suggest that 17D11 and 18C3 recognize an epitope on murine TrkB that contains different amino acids in rat TrkB.

TrkB Phosphorylation Analysis

Seven TrkB antibodies (6E2, 7F5, 11E1, 16E11, 17D11, 19E12 and 29D7) selected based on all activities described above were evaluated in Western analysis for induction of TrkB autophosphorylation. All antibodies led to robust TrkB phosphorylation, and these effects were antagonized by treatment with the kinase inhibitor K252a, indicating that these TrkB-binding antibodies caused activation of TrkB (FIG. 8).

ATCC Deposits

The hybridomas that produced the 17D11 and 29D7 TrkB antibodies were deposited with the ATCC on Aug. 18, 2005 and have been given ATCC patent deposit designations PTA-6948 and PTA-6949, respectively.

Example 2

This example describes further in vitro characterization and testing of a plurality of TrkB antibodies. In particular, this example describes experiments that were performed to assess the TrkB vs. TrkA and TrkC specificity of some of the antibodies of Example 1.

Materials and Methods

FACS Analysis

HEK-293 cells expressing human TrkA were detached from the plates with PBS containing 5 mM EDTA and transferred in to 5 ml Falcon tubes (Becton Dickinson, Cat. No. 352063) with $2\times10^5$ cells per tube. Cells were washed once with PBS by centrifuging at 800 rpm at 4° C. for 3 mM, and incubated for 30 mM at 4° C. with 100 μl of hybridoma culture supernatant or immune serum diluted in PBS with 1% FBS. The cells were washed 3 times with 1 ml PBS containing 1% FBS and incubated for 30 min at 4° C. in the dark with PE labeled goat anti-murine IgG, F(ab')$_2$ fragment (DAKO Corporation, Cat. No. R0480) in PBS containing 1% FBS. Cells were washed three times again and re-suspended in 250 μl PBS containing 1% FBS. Popidium iodide was used for detection of dead cells, which were excluded from analysis. The fluorescence of 5000 cells/tube was counted by a FAC-Scan flow cytofluorometer (Becton Dickinson).

Luciferase Assay

Stable lines of HEK-293 cells expressing human TrkA (or human TrkC) were prepared. Transfected cells were selected in the presence of hygromycin for 2 wks with limited dilutions. Following initial evaluation, a single clone of cells was chosen for the study. For the luciferase assay, cells were plated at $1.5 \times 10^4$ cells/well in 100 µl growth medium in 96-well plates. The next day, cells were treated with 10 µl of 10× final concentration of NGF (or NT-3) or test antibodies. Luciferase activities were measured 16 hr after the treatments using the Promega Steady-Glo assay kit according to the manufacturer's protocol. In brief, media was replaced with 100 µl of PBS and 100 µl of Steady-Glo reagent was added. After sealing the plates with TopSeal, the plates were shaken at Titer Plate Shaker at speed ~5 for 5 minutes and then luminescence was measured using a TopCount NXT v2.13 instrument (Packard).

Results

FACS Analysis of Monoclonal Antibodies

Figure 9A:
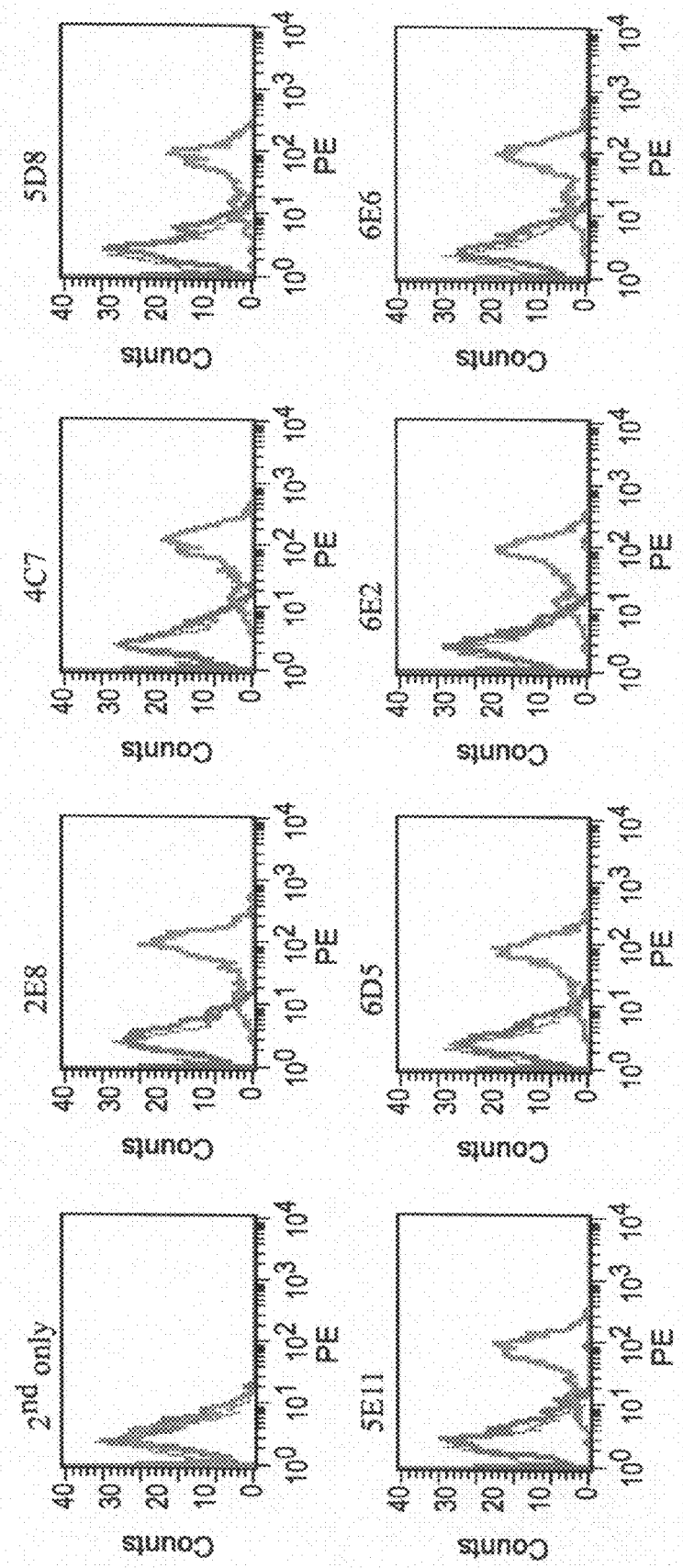
FIG. 9 depicts the results from a FACS TrkA binding assay (FIG. 9A) and a TrkA luciferase activity assay (FIG. 9B) that were obtained with certain anti-TrkB antibodies. These results show that inventive antibodies do not bind or activate human TrkA cells.
Figures 2, 9A:
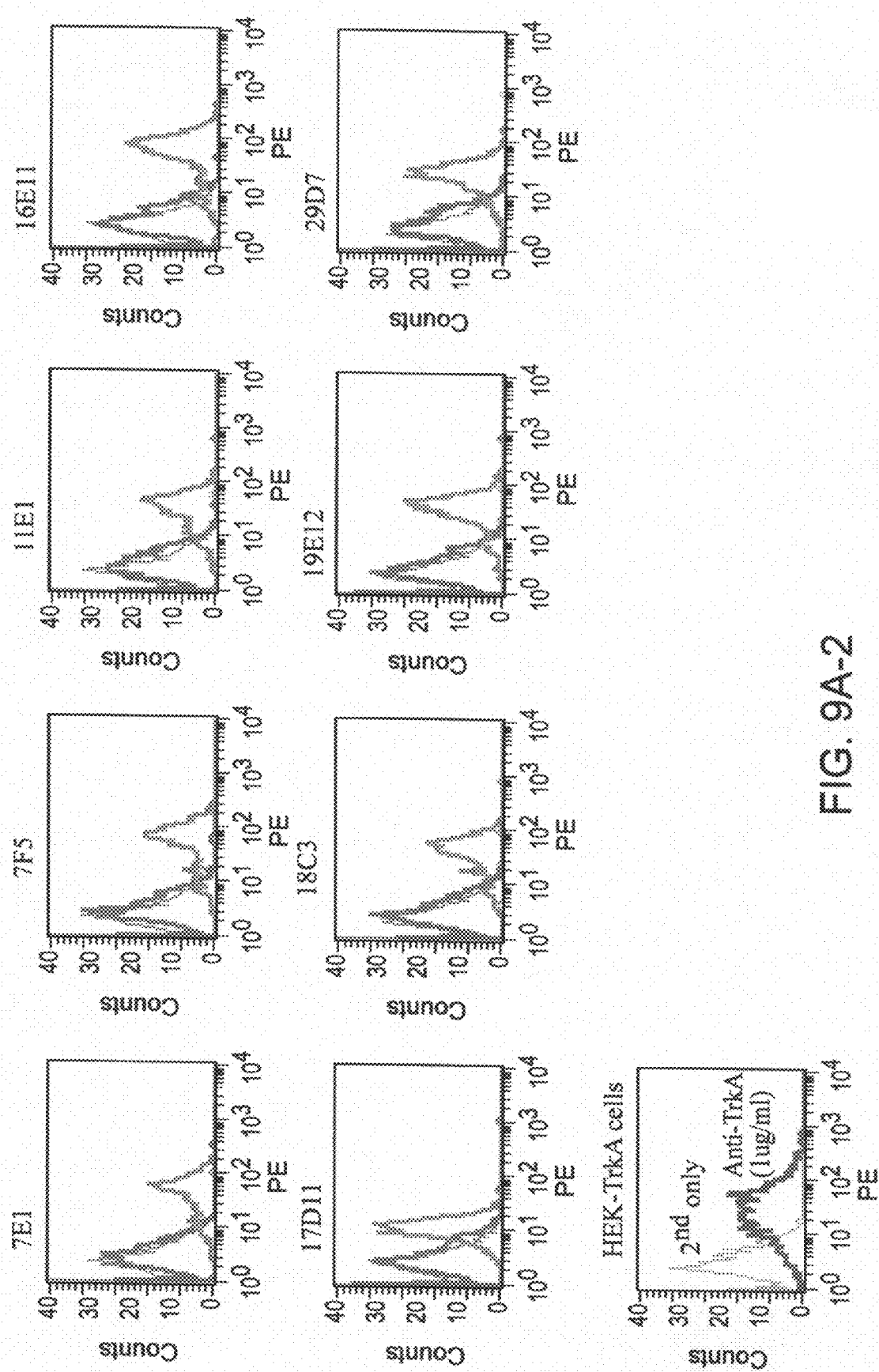

The neat conditioned media for each of the TrkB-specific monoclonal antibodies of Table 1 were characterized for their binding activities to human TrkA by FACS. All of the tested antibodies failed to bind to human TrkA. Specifically, the antibodies were tested at concentrations ranging from about 5 to about 60 µg/ml (see specific concentrations for each antibody in Table 1, these correspond to concentrations in the range of about 30 to about 500 nM) and each antibody failed to show any detectable binding. The FACS data is shown in FIG. 9A.

Luciferase Activities

Figure 9B:
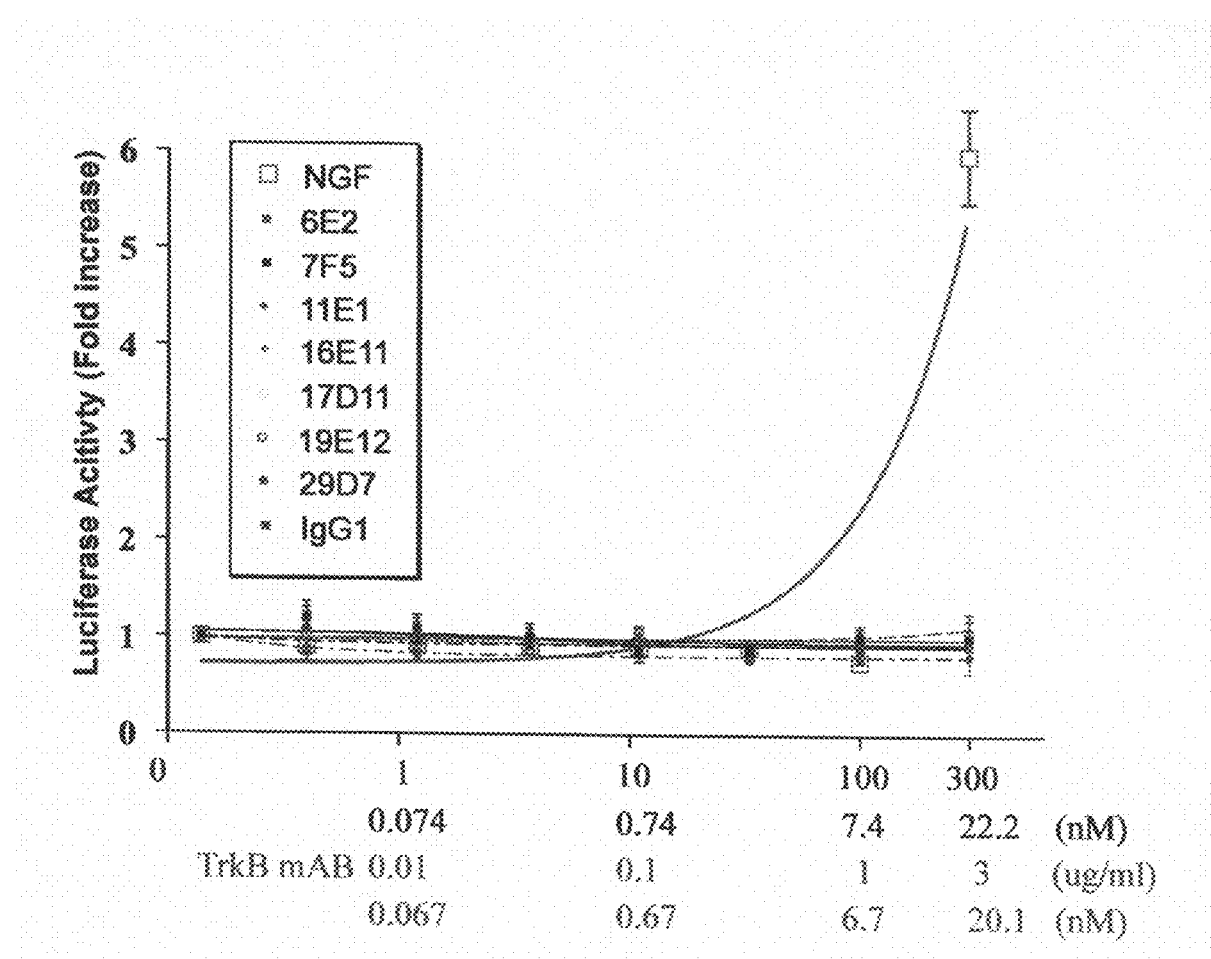
Figure 10:
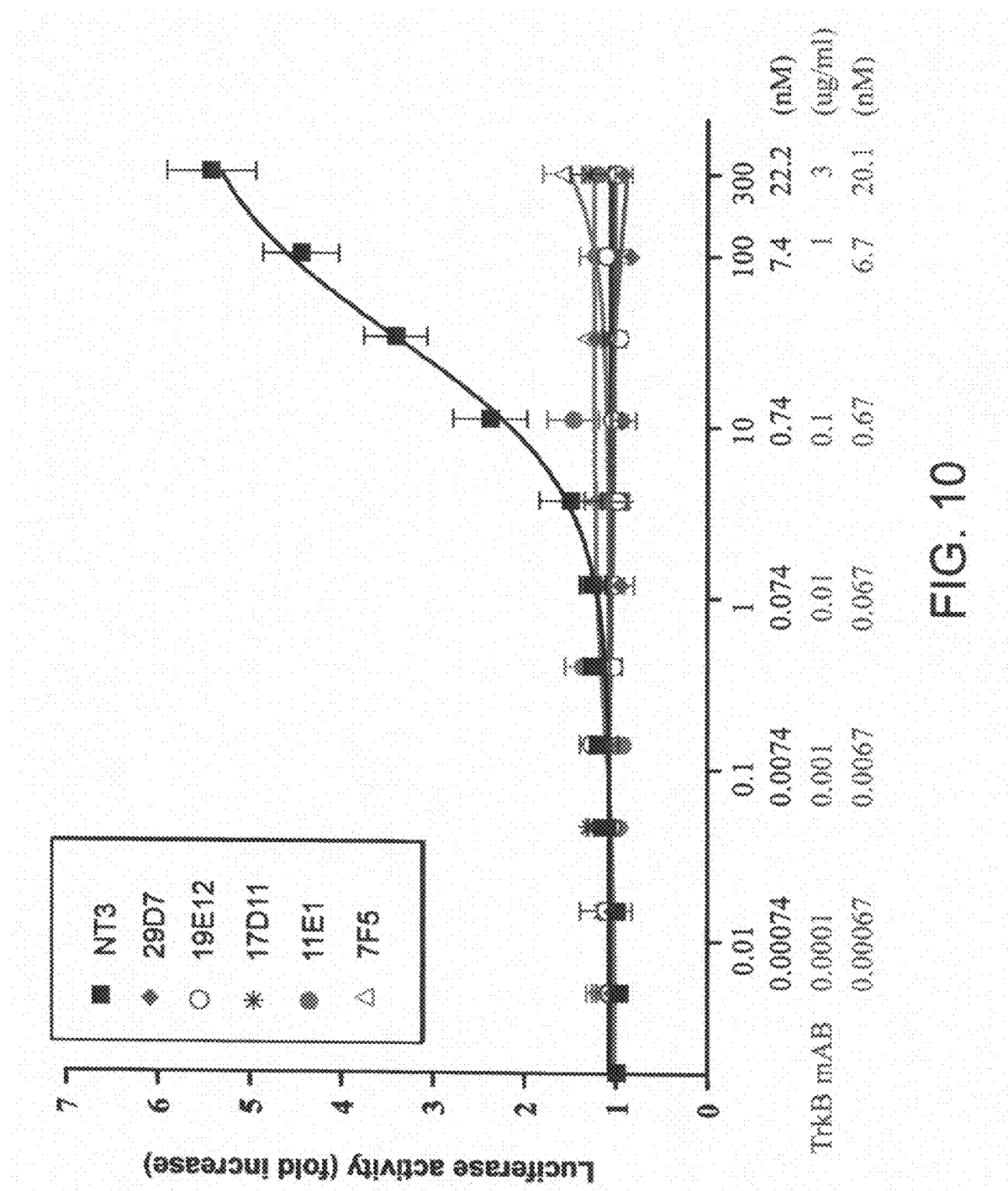
FIG. 10 depicts the results that were obtained when certain anti-TrkB antibodies were evaluated in a TrkC luciferase activity assay. These results show that inventive antibodies do not activate human TrkC cells.

A subset of the purified TrkB-specific antibodies of Table 2 were also examined using a TrkA or TrkC luciferase assay to assess agonist activities. None of the tested antibodies activated TrkA or TrkC. Specifically, the antibodies were tested at concentrations of up to about 3 µg/ml (about 20 nM) and in each case the antibodies failed to cause detectable increase above basal (see FIG. 9B for TrkA and FIG. 10 for TrkC). In contrast, NGF induced a ~6 fold increase over basal for TrkA at 300 ng/ml (FIG. 9A) and NT-3 induced a ~6 fold signal increase over basal for TrkC at 300 ng/ml (FIG. 10).

Example 3

This example describes the in vivo testing of a plurality of TrkB antibodies in a rodent model of neonatal hypoxia-ischemia (HI).

Materials and Methods

Animals and Surgical Procedures

Figure 11:
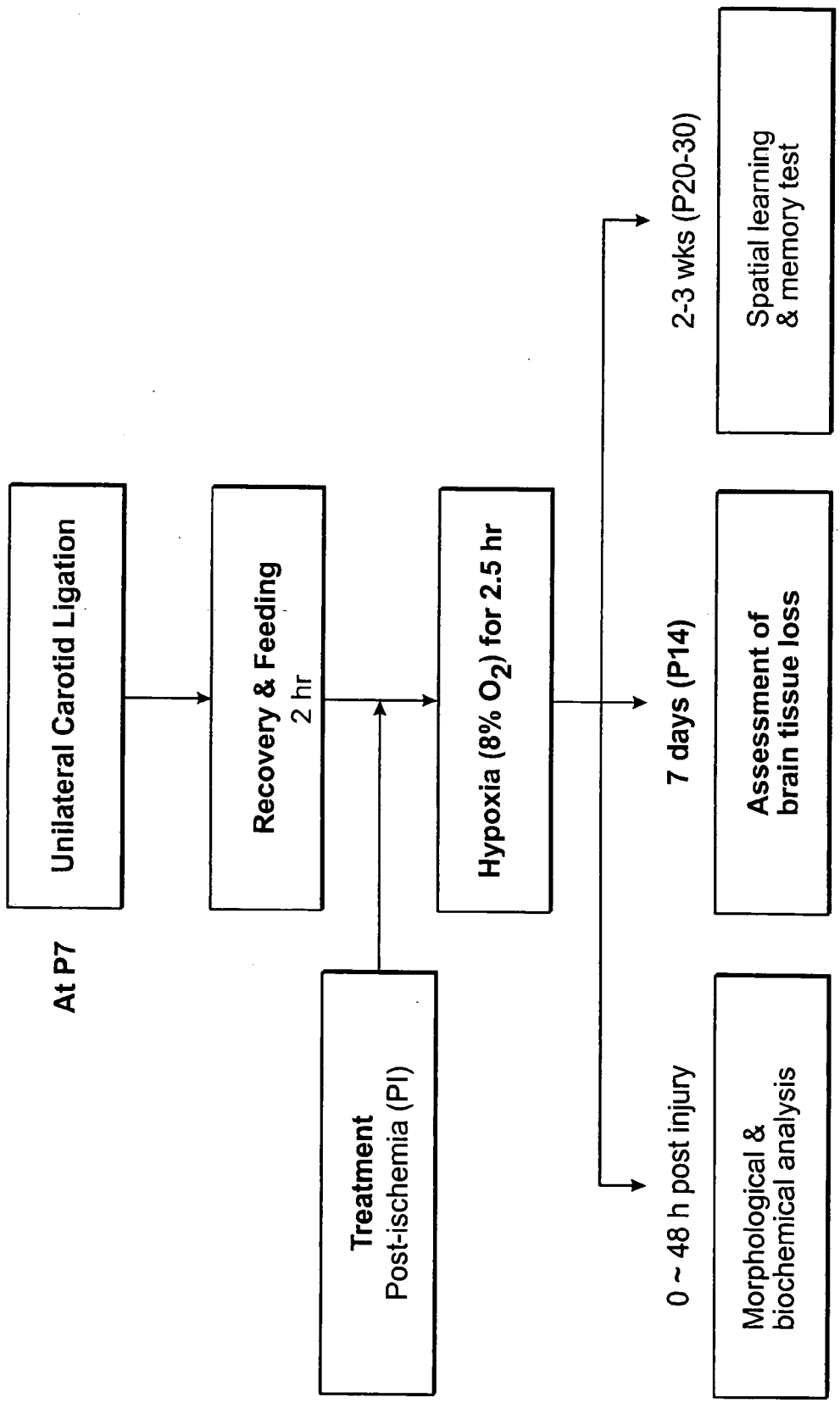
FIG. 11 depicts the rodent model of neonatal hypoxia-ischemia (HI) that is based on the Levine procedure.

The rodent model of neonatal hypoxia-ischemia (HI) was based on the Levine procedure that is set forth in FIG. 11 (e.g., see Levine, *Am. J. Pathol.* 36:1-17, 1960; Rice et al., *Ann. Neurol.,* 9:131-141, 1981 and Gidday et al., *Neurosci. Lett.* 168:221-224, 1994 each of which is incorporated herein by reference). Briefly, pups at P7 were anesthetized with 2.5% halothane and the left common carotid artery was permanently ligated. After the incisions were sutured, pups were returned to the home cage for recovery and feeding. Two hours later, pups were placed in individual containers, through which humidified 8% oxygen was flowed. After 2.5 hrs of a hypoxic ischemic period, the pups were returned to their home cages. For treatment, animals received a 5 µl intracerebroventricular injection of 0.1 or 0.3 nmole of either BDNF, anti-TrkB monoclonal antibody 29D7, control IgG1 or vehicle just prior to the hypoxic insult.

Assessment of Brain Tissue Loss

Figure 17:
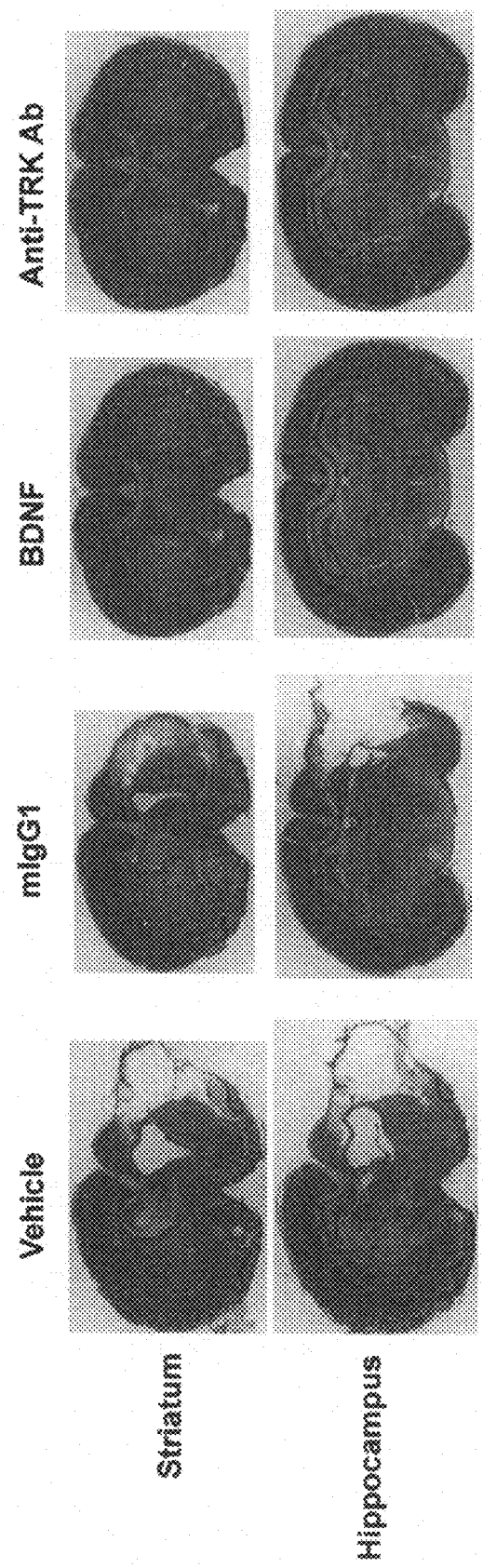
FIG. 17 compares the stains that were obtained from the striatum and hippocampus for different treatments after hypoxic-ischemic (HI) injury.
Figure 18B:
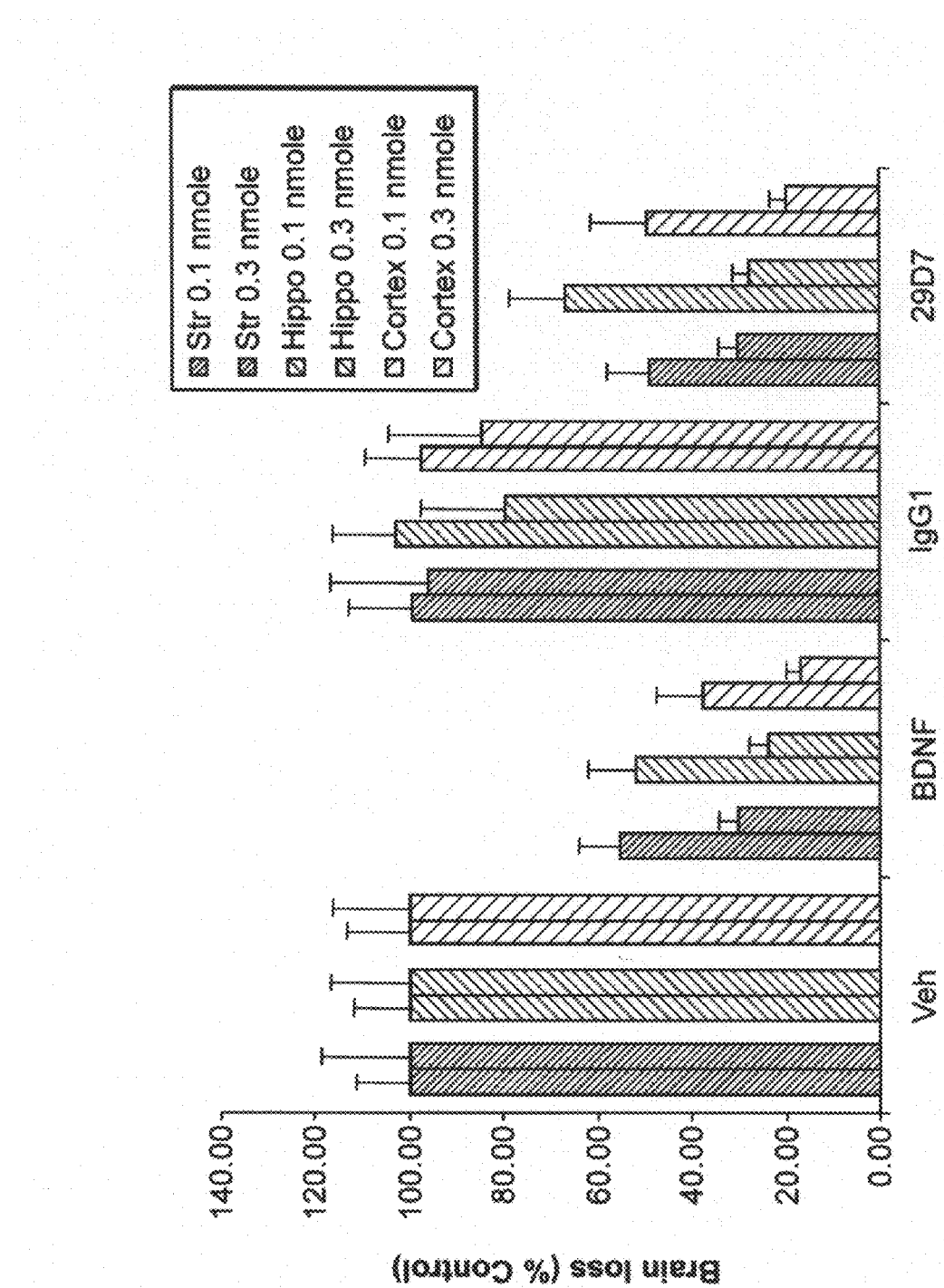
FIG. 18 compares the total brain tissue loss (A) and sub-regional tissue loss (B) for different treatments after HI injury. The data are shown as mean and standard error of the mean (S.E.M.). BDNF and anti-TrkB monoclonal antibody 29D7 showed significant dose-dependent protection of the brain from HI injury. The protection was not localized to any specific sub-region of the brain but greatest protection was generally observed in the cortex.

At P14, brain sections were prepared from some of the mice to determine damage caused by the HI injury. The coronal sections of the striatum, cortex and hippocampus were stained with cresyl violet and the percent area loss in the lesioned hemisphere was compared with the intact area. FIG. 17 compares the stains that were obtained from the striatum and hippocampus for different treatments. FIGS. 18A and 18B compare the total brain tissue loss and sub-regional tissue loss, respectively, for different treatments. The data are shown as mean and standard error of the mean (S.E.M.). BDNF and anti-TrkB monoclonal antibody 29D7 showed significant dose-dependent protection of the brain from HI damage. The protection was not localized to any specific sub-region of the brain but greatest protection was generally observed in the cortex.

Biochemical Analysis 24 hours after the HI injury, brain sections were prepared from a subset of the mice for biochemical analysis. Hippocampal and cortical brain tissues were dissected, lysed and subjected to several biochemical assays.

Figure 19:
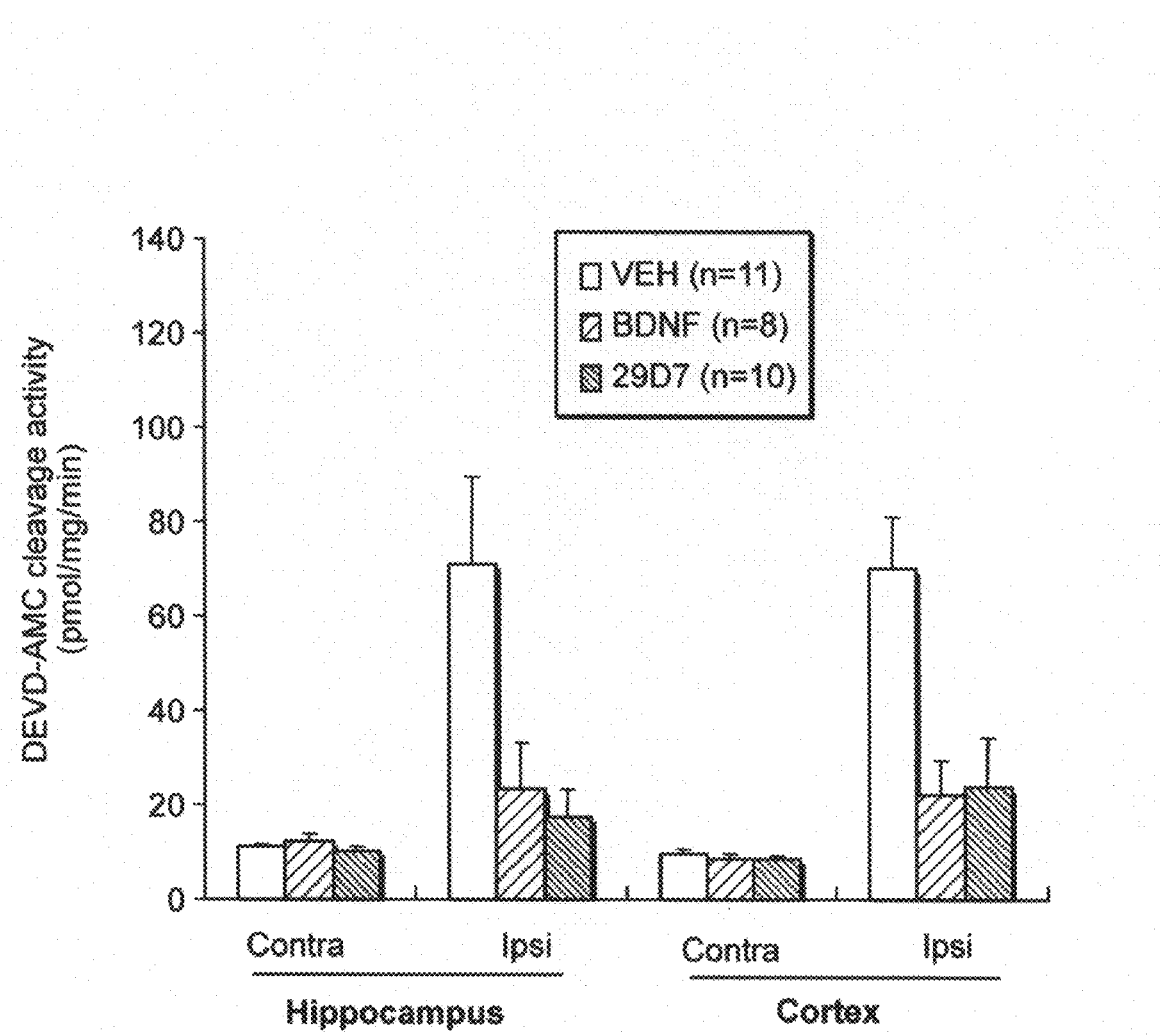
FIG. 19 shows the results of a DEVD-AMC cleavage assay that was used to determine caspase-3 activities for different treatments after HI injury. The results for different regions of the brain are shown as mean±S.E.M. BDNF and anti-TrkB monoclonal antibody 29D7 blocked caspase-3 activation caused by HI injury.

A DEVD-AMC cleavage assay was used to determine caspase-3 activities (e.g., see Nagase et al., *Immunol Lett.* 84:23, 2002 incorporated herein by reference). The results for different regions of the brain are shown in FIG. 19 for mice that were given 0.1 nmole of different test reagents (mean±S.E.M.). BDNF and anti-TrkB monoclonal antibody 29D7 blocked caspase-3 activation caused by HI injury.

Figure 20:
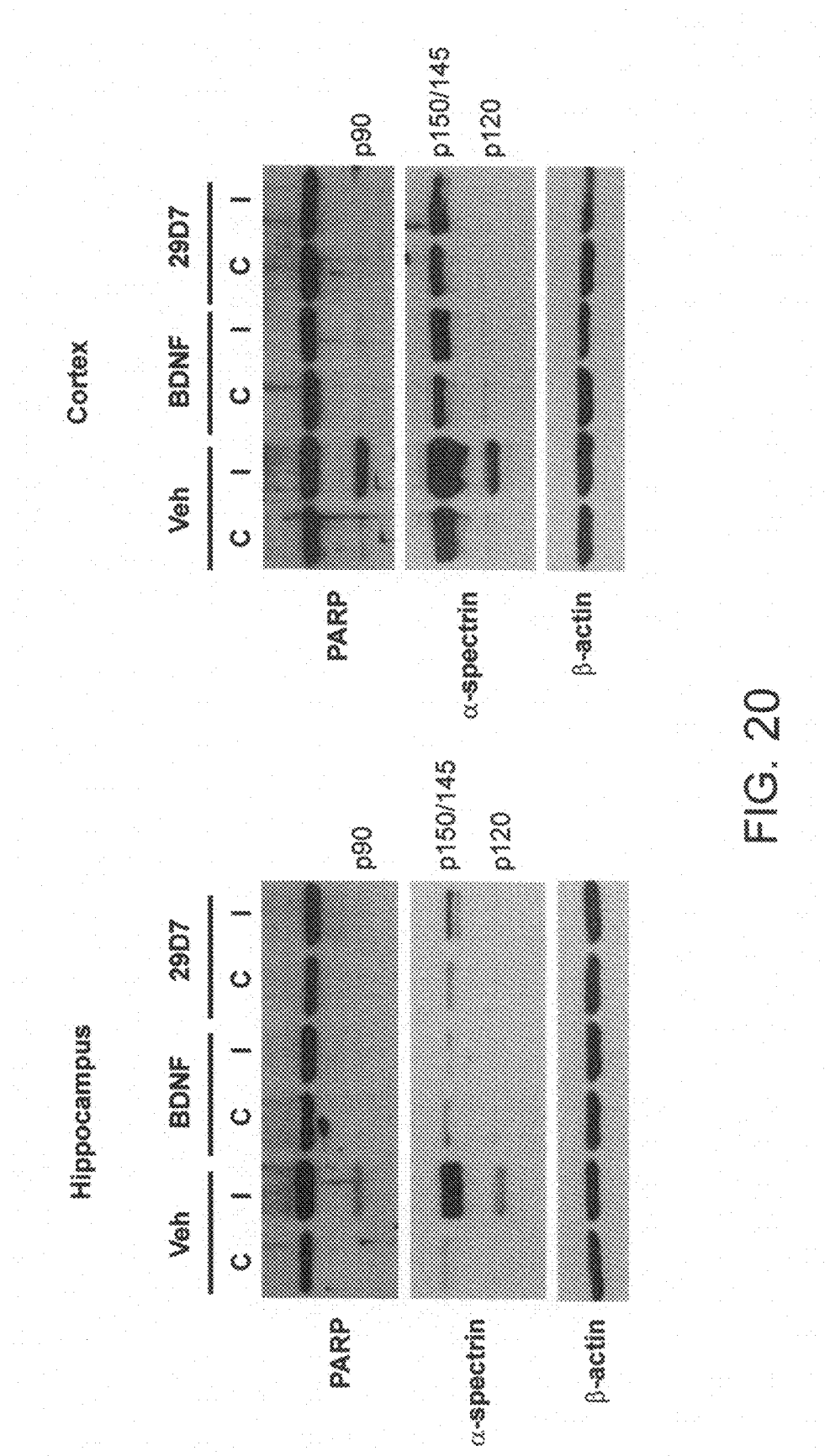
FIG. 20 shows immunoblots of protein samples taken from mice given different treatments after HI injury. The samples were separated by SDS-PAGE and subjected to immunoblotting with antibodies against certain caspase-3 substrates (PARP and α-spectrin). Antibodies against β-actin were used as controls to verify equal loading of proteins. The results show that cleavage of these caspase-3 substrates was inhibited by BDNF and anti-TrkB monoclonal antibody 29D7 (C=contra and I=ipsi sides of carotid ligation).

Protein samples (30 µg/lane) from mice treated with 0.3 nmole of different test reagents were separated by SDS-PAGE and subjected to immunoblotting with antibodies against certain caspase-3 substrates (PARD and α-spectrin). Antibodies against β-actin were used as controls to verify equal loading of proteins. The results shown in FIG. 20 demonstrate inhibition of cleavage of these caspase-3 substrates by BDNF and anti-TrkB monoclonal antibody 29D7 (C=contra and I=ipsi sides of carotid ligation).

Follow Up Experiments

The following are prophetic follow up experiments that could be performed on the mice of this study. The performance of the remaining mice in spatial learning and memory tests could be assessed (e.g., without limitation the tests described in Almli et al., *Exp. Neurology* 166:99-114, 2000 incorporated herein by reference). For example, the mice could be tested between P20-P30. Optionally, the performance could be assessed over several days during that period or even at later time points.

Treatment protocols that produce a positive outcome (as measured by a reduction in brain tissue loss, an improvement in spatial learning and memory or otherwise) could be repeated over an even greater range of dosages. Alternatively or additionally, treatment protocols could be repeated with different modes of administration (e.g., intraperitoneal administration, intravenous administration, etc.); with different start points (e.g., before ligation, immediately after hypoxia, with a variable delay after hypoxia, etc.); and/or with different duration or frequency (e.g., daily treatment for 2 wks post injury, etc.).

Example 4

This example describes the preparation and testing of human single-chain Fv (scFv) antibodies against human TrkB. Human antibody phage display libraries (CS, BMV and DP-47; Cambridge Antibody Technology) containing single-chain Fv fragments were selected for TrkB binding using the following methods.

Materials and Methods

Selection of Antibodies by Panning

10 μg of hTrkB-EDC-Fc was coated on Nunc Maxisorp plate in 100 μl and left overnight at 4° C. A phage library was pre-blocked (50 μl phage aliquot added to 50 μl of 6% skimmed milk in 2×PBS) and negatively selected against PSGL-Fc (Wyeth, Lot. No. 00H25M004) for 1 hr at room temperature to deplete phage reactive against Fc. Deselected phage were transferred to the target protein-coated plate (hTrkB-EDC-Fc) and incubated at room temperature for 2 hrs. Wells were washed 10 times with PBS/0.1% Tween 20 and 5 times with PBS. Bound phage were eluted with 50 μl/well of freshly made 100 mM TEA (140 μl of TEA in 10 ml of ultra pure water). Eluted phage were neutralized using 25 μl of sterile 1 M Tris-HCl pH 7.5. Phage were infected into 10 ml of a mid-log (O.D at 600 nm=0.5) of $E.\ coli$ TG1 cells. Transformed cells were spread onto a 2×TYAG agar Bioassay plate and incubated overnight at 30° C.

Soluble Phase Selection (Biotin Selection)

Phage antibodies were selected using biotinylated hTrkB-EDC-Fc according to the protocol described above with the following exceptions. Pre-blocked phage were deselected first against 100 nM biotinylated PSGL-Fc followed by positive selection on 100 nM biotinylated hTrkB-EDC-Fc. Human TrkB specific phage were captured using pre-blocked magnetic streptavidin beads (Dynabeads M-280 streptavidin, Cat. No. 112.06). Beads were washed 10 times with PBS/0.1% Tween 20 and 3 times with PBS. Bound phage were eluted with 200 μl of freshly made 100 mM TEA (140 μl of TEA in 10 ml of ultra pure water) and neutralized using 100 μl of sterile 1 M Tris-HCl pH 7.5 to the eluted phage to neutralize the TEA. Phage were infected into $E.\ coli$ and propagated as described in the previous step.

Phage Rescue $E.\ coli$ infected with phage were scrapped off the Bioassay agar plates and mixed with 10 ml 2×TYAG per Bioassay plate (2×TY with 100 μg/ml Amp and 2% glucose). 20 ml 2×TYAG was inoculated with 100 μl of cell suspension and grown at 37° C. (300 rpm) to OD at 600 nm=0.3-0.5. $E.\ coli$ were superinfected with 3.3 μl of MK13KO7 helper phage and incubated at 37° C. (150 rpm) for 1 hr. Superinfected cells were re-suspended in 20 ml 2×TYAK medium (2×TY/100 μg/ml Amp/50 μg/ml Kanamycin) and grown overnight at 25° C. at 280 rpm. $E.\ coli$ were spun at 3500 rpm for 15 min and the supernatant containing the phage were used for the next round of selection.

Phage Antibody Preparation for ELISA

Single colonies of infected $E.\ coli$ were picked into microtitre wells (Costat Cellwells) containing 150 ml of 2×TYAG media (2% glucose) per well. Clones were allowed to grow at 37° C. (100-120 rpm) for 5-6 hrs (OD at 600 nm=0.5). M13K07 helper phage stock ($10^{13}$ pfu/ml) was diluted 1:1000 with 2×TYAG medium and 20 μl was added to each well. The wells were incubated at 37° C. (100 rpm) for 1 hr. Plates were centrifuged at 3200 rpm for 10 min, the supernatant was removed and the cells were resuspended in 150 μl of 2×TYAK medium. Cultures were grown overnight at 25° C. (120 rpm). The next day, plates were centrifuged at 3200 rpm for 15 min and the supernatant was transferred to a fresh plate for the phage ELISA assay.

Phage ELISA

ELISA plates were coated with 50 μl per well of 1 μg/ml of hTrkB-EDC-Fc (BSA as a control) in PBS at 4° C. overnight. Wells were rinsed 3 times with PBS and blocked with 300 μl per well of PBS/3% skimmed milk at room temperature for 1 hr. Phage were blocked with equal volume of PBS/6% skimmed milk and incubated at room temperature for 1 hr. 50 μl of blocked phage were added to ELISA wells and incubated at room temperature for 1 hr. Plates were washed 3 times with PBS/0.1% Tween followed by 3 times with PBS. 50 μl of HRP-Mouse anti-M13 antibody in PBS/3% skimmed milk (1:5000, Amersham Pharmacia biotech, Cat. No. 27-9421-01) was added to each well and incubated at room temperature for 1 hr. Plates were washed as before and 50 μl TMB substrate was added to each well and developed for 2-5 min. The reaction was stopped by adding 50 μl of 0.5 M sulphuric acid and the absorbance was read at 450 nm.

Single-Chain Fv Preparation for FACS

Single colonies were picked and grown in deepwell microtiter plates containing 0.9 ml 2×TYAG media at 37° C. for 5-6 hrs. scFv expression was induced by adding IPTG to a final concentration of 0.02 mM in 2×TY medium and growth at 30° C. overnight. $E.\ coli$ were harvested after overnight growth and osmotically shocked with 150 μl TES buffer diluted 1:5 in water and incubated on ice for 30 min. Cells were centrifuged and the supernatant transferred to a fresh plate for the FACS assay. 293 cells stably transfected with TrkB were stained with scFv prepared as described. Cells were incubated on ice for 30 min and then washed with PBS buffer. Single-chain Fv was detected using a solution containing 9E10 anti-myc antibody diluted 1:1000 followed by addition of PE conjugated anti mouse IgG-Fc antibody diluted 1:500. Stained cells were analysed on a Bectin-Dickinson Flow Cytometer.

Results

Phage ELISA

Figure 12:
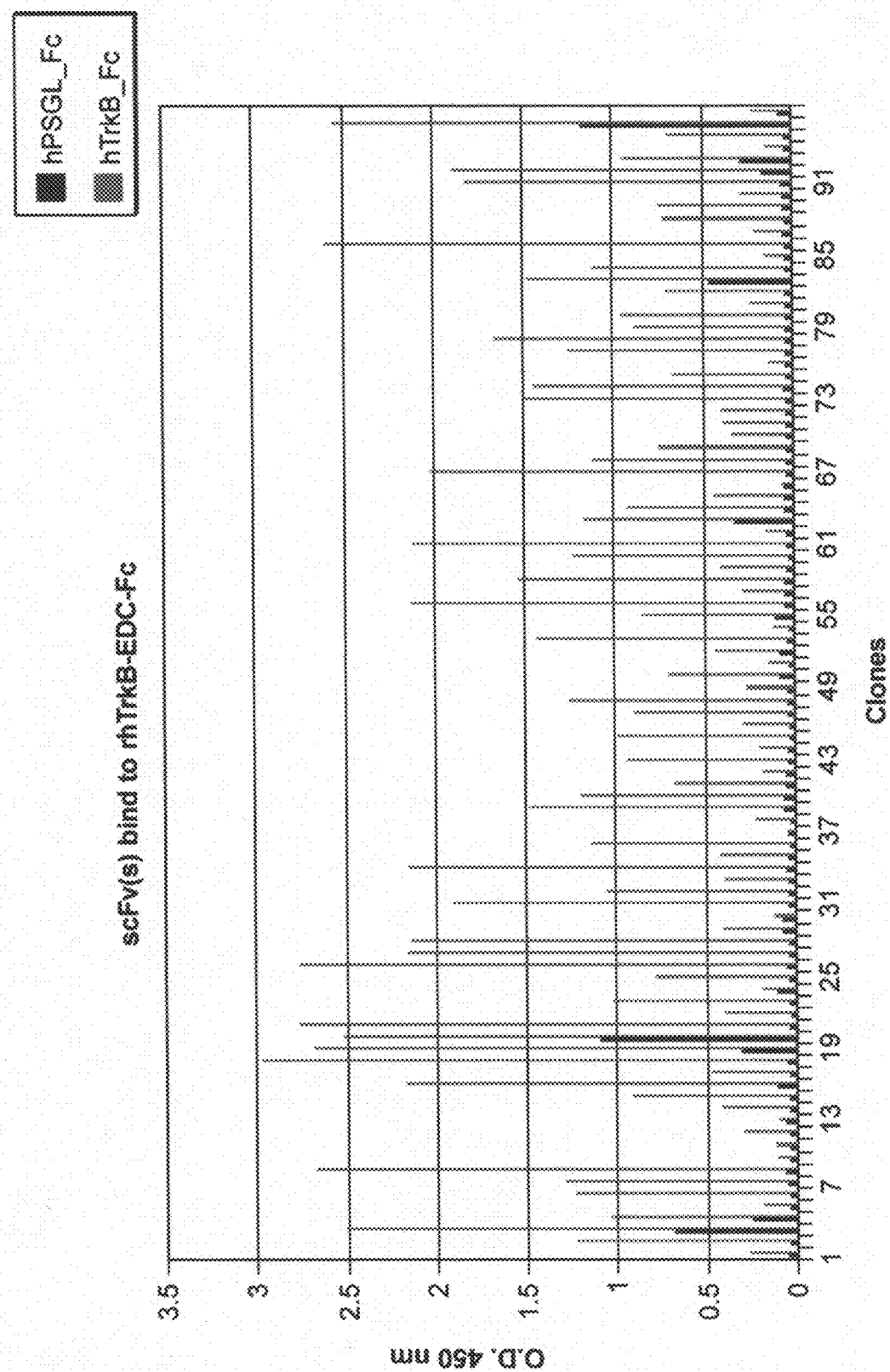
FIG. 12 shows the phage binding ELISA data from a representative set of TrkB positive scFv clones (BMV library panning selection).

Table 4 shows the results from phage ELISA assays from the different phage library selections (panning and soluble selections). FIG. 12 shows the phage binding ELISA data from a representative set of TrkB positive clones (BMV library panning selection). The majority of TrkB selected clones showed strong and specific reactivity against TrkB-EDC-Fc and not to the control protein PSGL-Fc.

TABLE 4

| Antigen (selection) | Library | phage ELISA (% positives) | Sequence (% diversity) |
|---|---|---|---|
| TrkB-EDC-Fc (panning) | CS | 78 | 53 |
| | BMV | 58 | 23 |
| | DP-47 | 45 | 39 |
| Biotinylated TrkB-EDC-Fc (soluble) | CS | 3 | 100 |
| | BMV | 6 | 50 |
| | DP-47 | 10 | 50 |

After two rounds of panning selection, 78% of randomly picked clones from the CS library were positive for TrkB-EDC-Fc binding but not for PSGL-Fc binding. Likewise, 3% of clones were positive after two rounds of the soluble selections. The numbers for the BMV and DP-47 libraries were 58% and 45% positive clones from panning selection and 6% and 10% from soluble selection. Using DNA sequencing, we confirmed that 53% of the CS panning clones were unique whereas 100% of the CS soluble selection clones were unique. The numbers for the BMV and DP-47 libraries were 23% and 39% unique from panning selections and 50% and 50% unique from soluble selections.

FACS Analysis

Figure 13B:
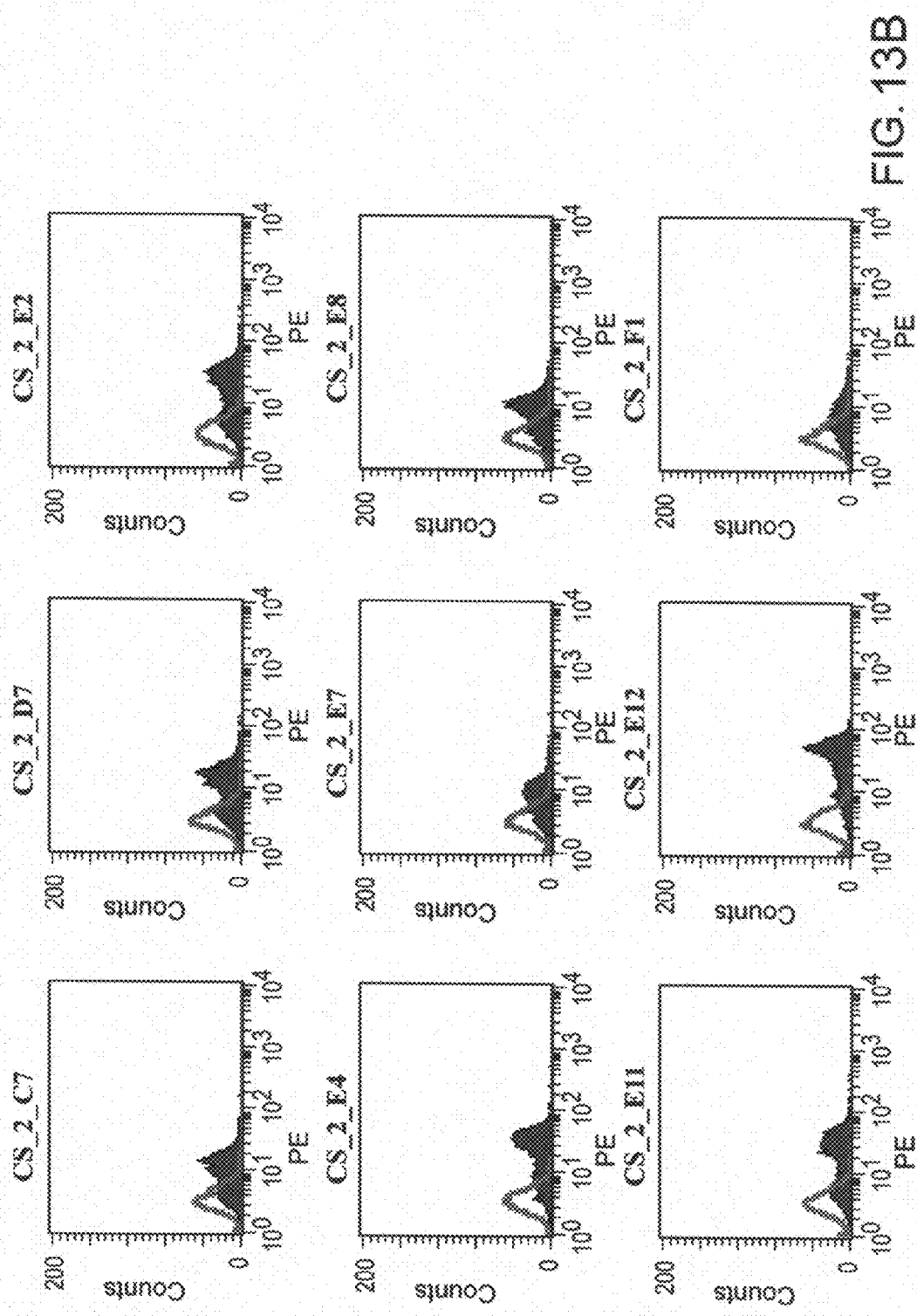
Figure 13C:
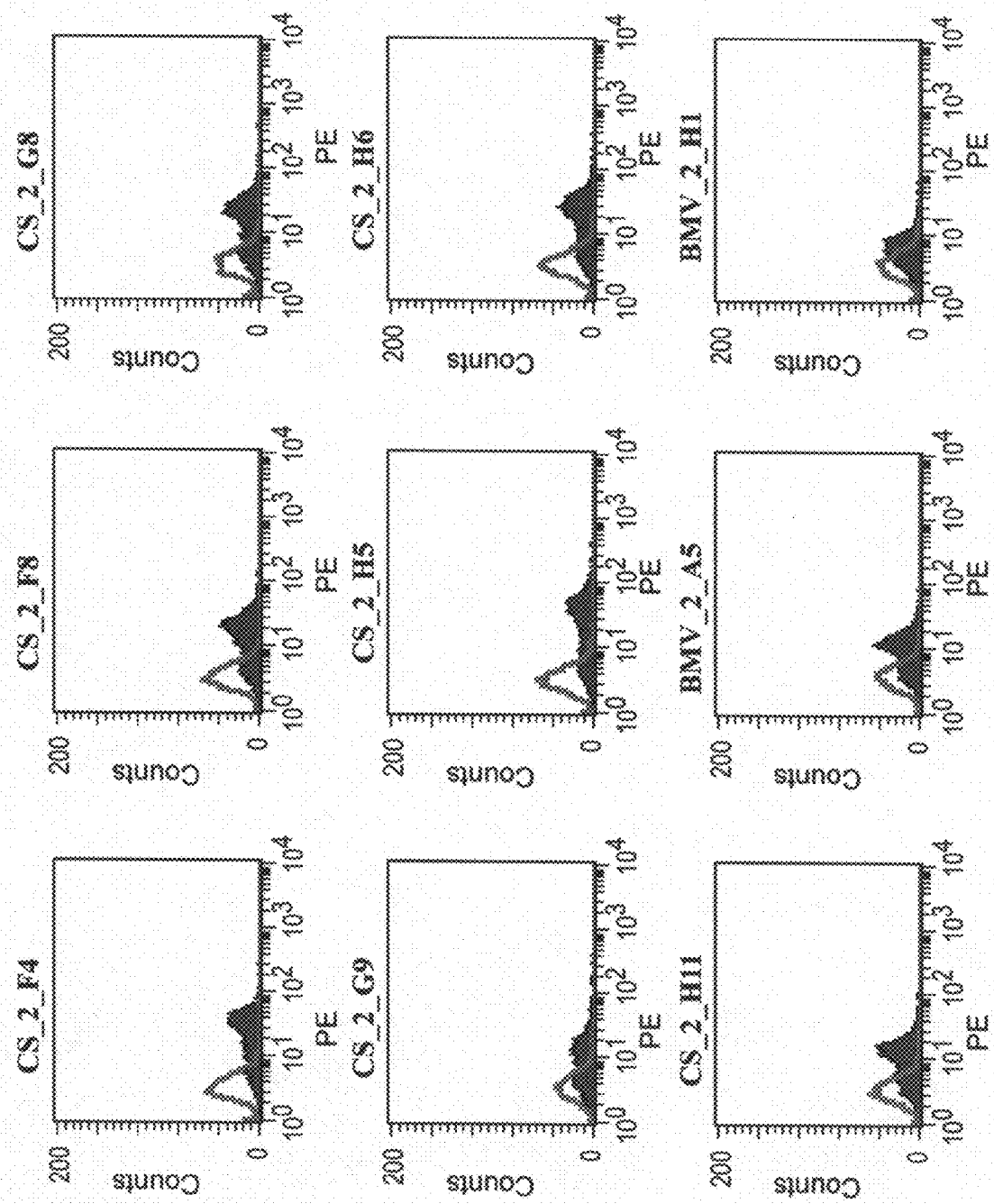
Figure 13D:
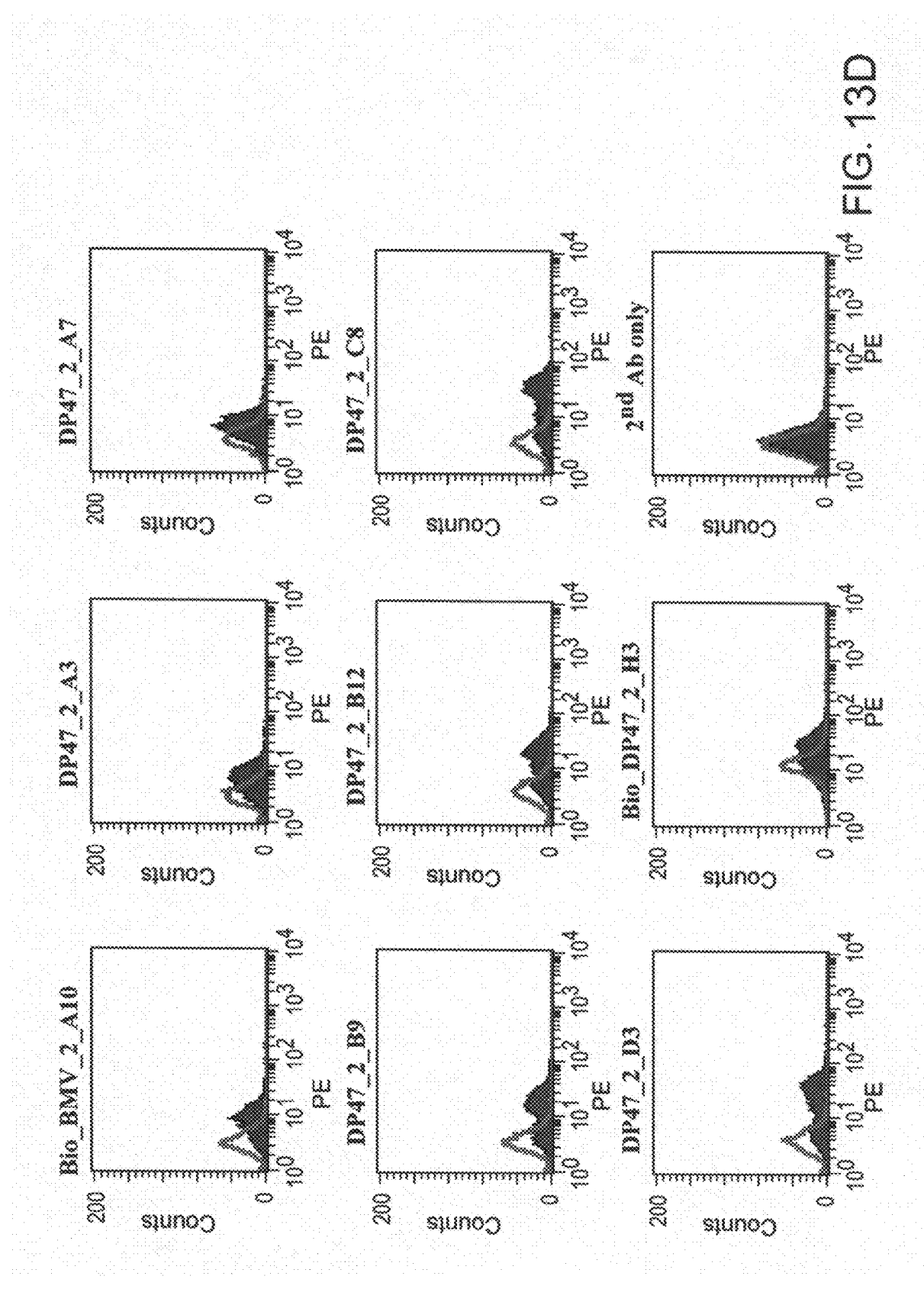

FIG. 13 shows the binding specificity of TrkB selected scFv antibodies tested using the FACS assay. The data shows that TrkB selected scFv antibodies react with membrane associated TrkB in a specific manner (filled blue histograms) with no cross-reactivity to control cells (open green histograms).

Example 5

This example compares the binding activities of the 29D7 TrkB antibody and a 29D7 Fab fragment against human and mouse TrkB. Mouse (rhTrkB-EDC-Fc) and human (rmTrkB-EDC) TrkB were coated on ELISA plates as described above in Example 1.

Figure 14A:
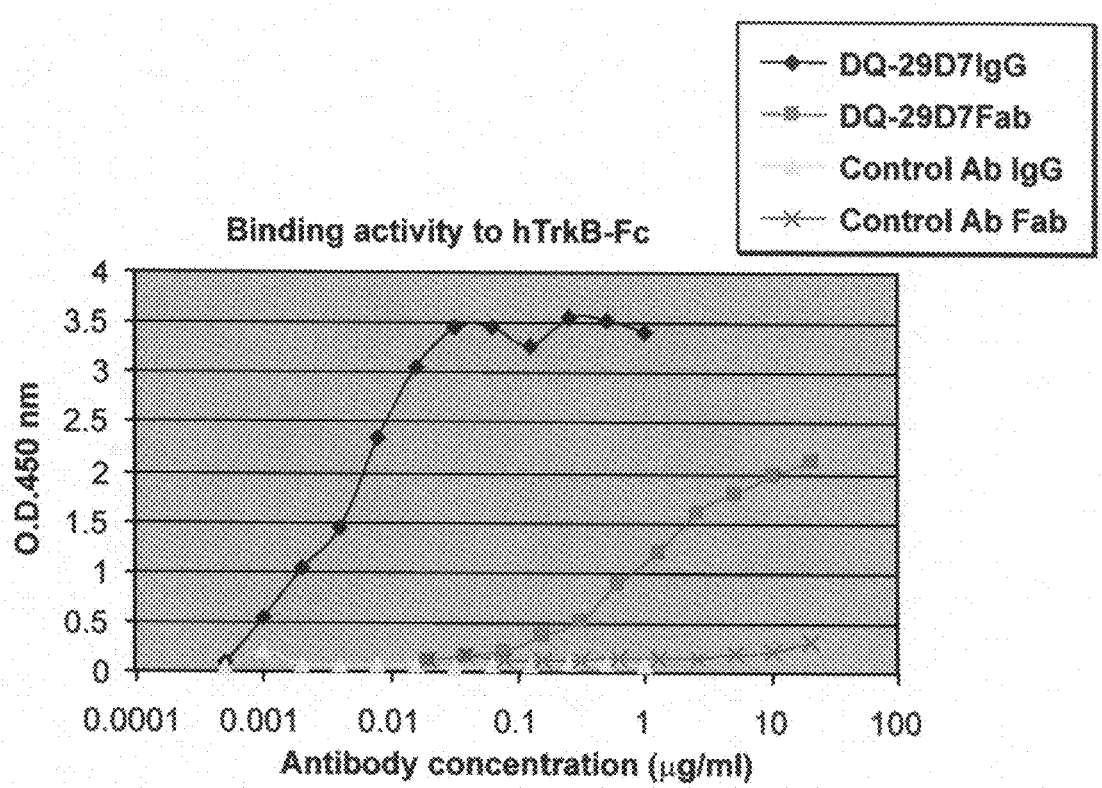
FIG. 14 show ELISA binding results for 29D7 IgG antibody and its Fab fragment with human (FIG. 14A) and mouse (FIG. 14B) TrkB. Both total IgG and Fab of 29D7 showed dose-dependent binding activities to human and mouse TrkB. However, the $ED_{50}$ value of the Fab was about 100 fold lower than that of intact 29D7. Neither an isotype control IgG1 nor its Fab fragment bound to TrkB.
Figure 14B:
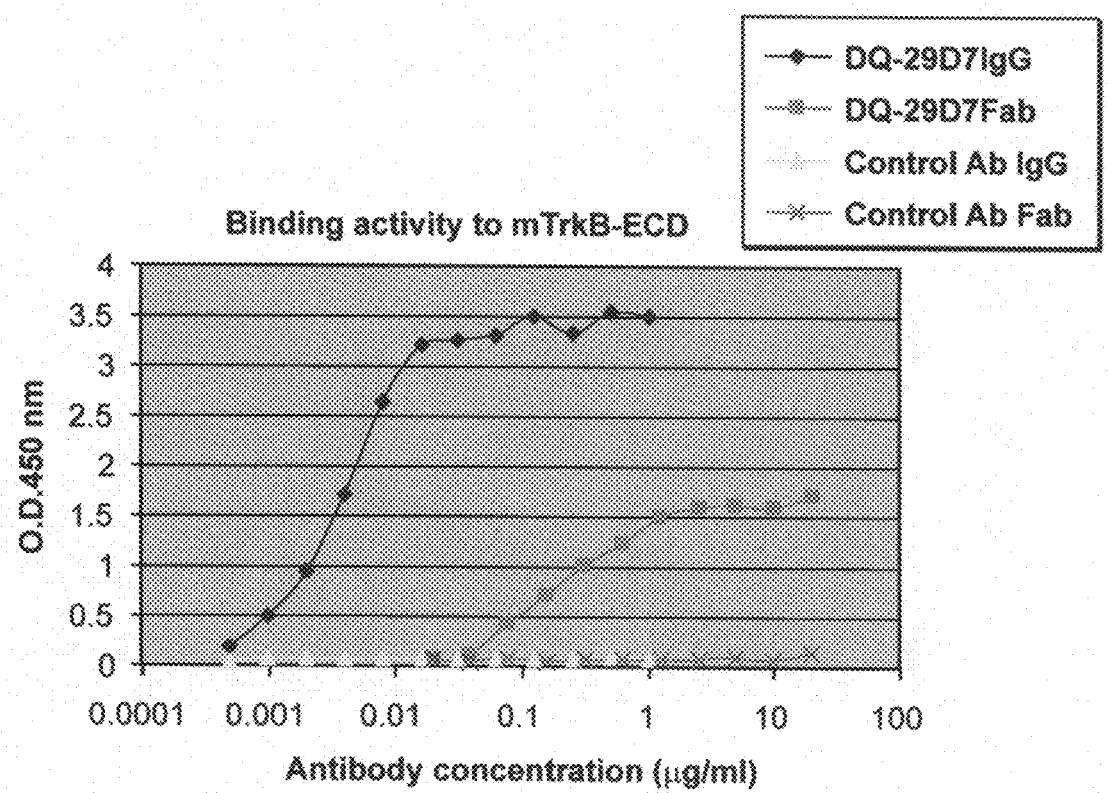

FIGS. 14A and 14B show the ELISA binding results for human and mouse TrkB, respectively. Both the 29D7 IgG antibody and its Fab fragment have dose-dependent binding activities to human and mouse TrkB. However, the $ED_{50}$ value of the Fab was about 100 fold lower than that of intact 29D7. Neither an isotype control IgG1 nor its Fab fragment bound to TrkB.

Example 6

This example compares the agonistic activities of the 29D7 TrkB antibody and the Fab fragment of Example 5 against human TrkB. Agonistic activities were examined using a luciferase assay and HEK-293 cells which express surface rhTrkB as described in Example 1.

Figure 15:
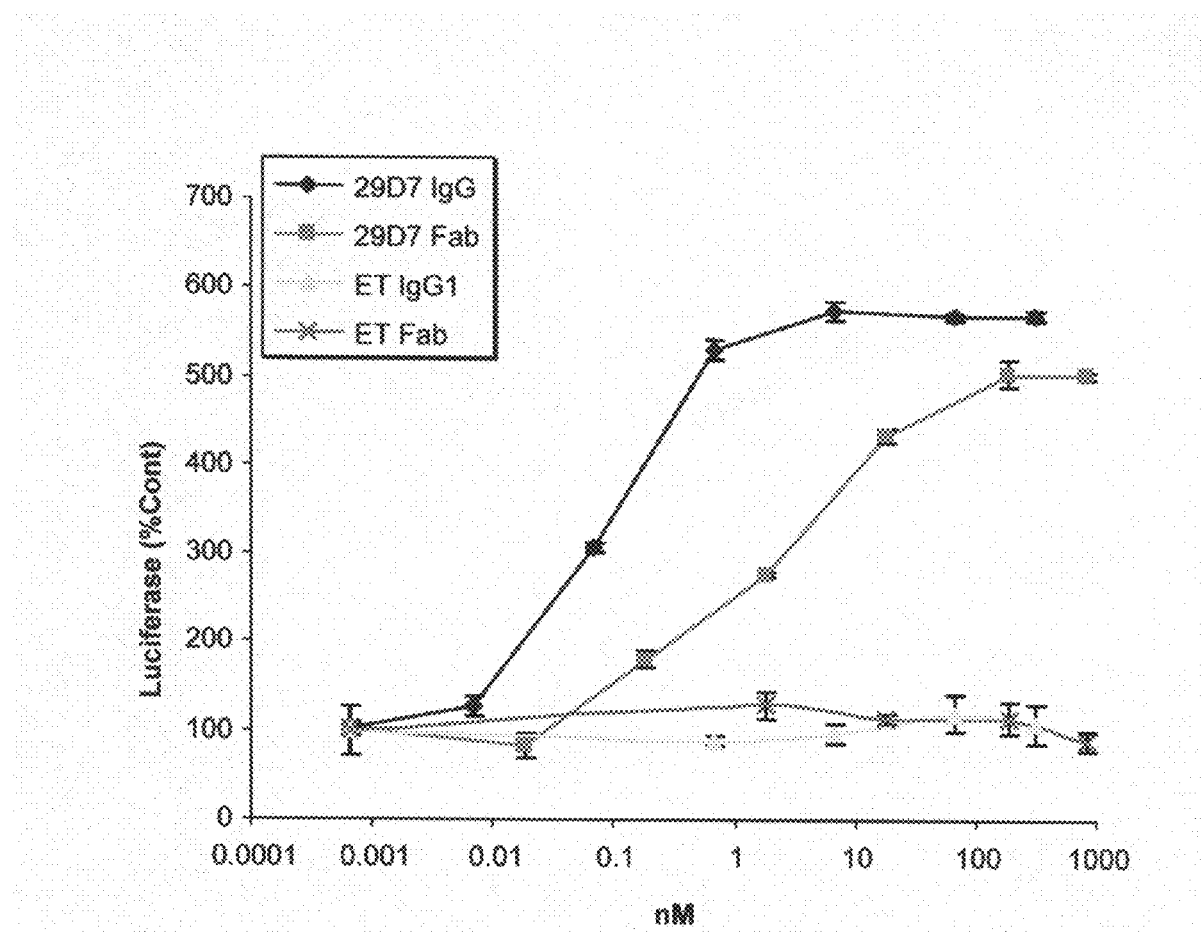
FIG. 15 shows luciferase activity in HEK-293 cells measured 16 hours post-treatment with 29D7 IgG or 29D7 Fab. Both total IgG and Fab of 29D7 induced dose-dependent luciferase activities, indicating activation of TrkB. However, the $EC_{50}$ value of 29D7 Fab was about 27 fold higher than that of 29D7 IgG (0.083 nM and 2.28 nM for 29D7 IgG and 29D7 Fab, respectively). Neither an isotype control IgG1 nor its Fab fragment had effects on TrkB activation.

HEK-293 cells were treated with 29D7 IgG or 29D7 Fab at indicated concentrations and accumulating luciferase activities were measured 16 hours post-treatment. As shown in FIG. 15, both total IgG and Fab of 29D7 induced dose-dependent luciferase activities, indicating activation of TrkB. However, the $EC_{50}$ value of 29D7 Fab was about 27 fold higher than that of 29D7 IgG (0.083 nM and 2.28 nM for 29D7 IgG and 29D7 Fab, respectively). Neither an isotype control IgG1 nor its Fab fragment had effects on TrkB activation.

Example 7

This example describes the epitope mapping analysis of certain inventive TrkB monoclonal antibodies. The mapping was performed against linear, single looped and double looped peptides that were deduced from sequences within the human TrkB extracellular domain.

Figure 16:
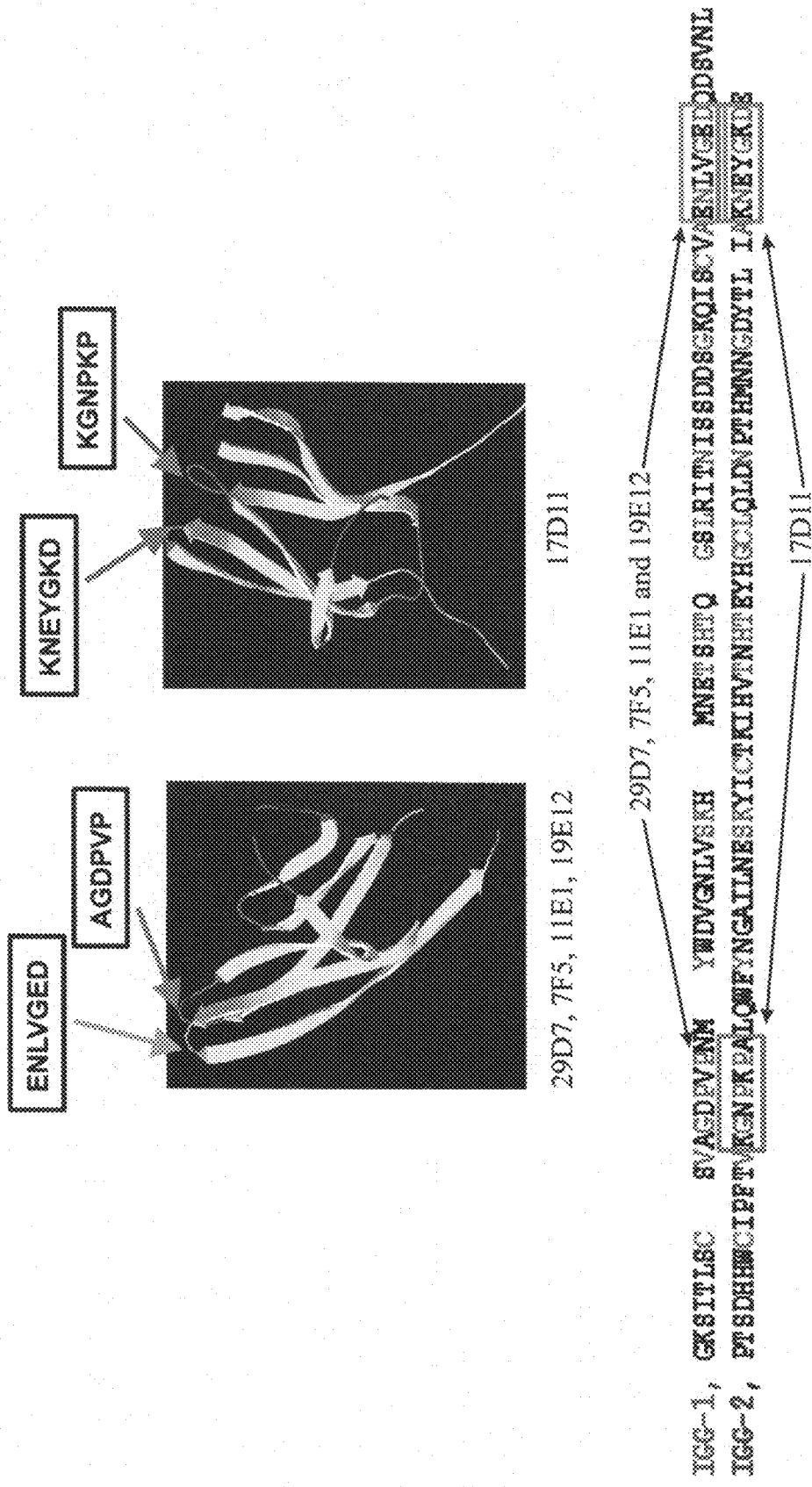
FIG. 16 shows results from the epitope mapping analysis of anti-TrkB monoclonal antibodies 17D11, 29D7, 7F5, 11E1 and 19E12. The 17D11 monoclonal antibody recognizes loop-3 of the IgG-2 segment of human TrkB (KNEYGKD, SEQ ID NO:7, amino acids 364 to 370 of SEQ ID NO:1); and loop-1 of the IgG-2 segment of human TrkB (KGNPKP, SEQ ID NO:8, amino acids 308 to 313 of SEQ ID NO:1). The 29D7, 7F5, 11E1 and 19E12 monoclonal antibodies all recognize loop-3 of the IgG-1 segment of human TrkB (ENLVGED, SEQ ID NO:10, amino acids 269 to 275 of SEQ ID NO:1); and may also recognize loop-1 of the IgG-1 segment of human TrkB (AGDPVP, SEQ ID NO:11, amino acids 221 to 226 of SEQ ID NO:1). The IgG-1 and IgG-2 segments of TrkB shown in FIG. 16 correspond to SEQ ID NOs: 12 and 13, respectively.

As shown in FIG. 16, the 17D11 monoclonal antibody recognizes loop-3 of the IgG-2 segment of human TrkB (KNEYGKD, SEQ ID NO:7, amino acids 364 to 370 of SEQ ID NO:1); and loop-1 of the IgG-2 segment of human TrkB (KGNPKP, SEQ ID NO:8, amino acids 308 to 313 of SEQ ID NO:1). The mouse sequence for the former epitope (KNEYGKD, SEQ ID NO:7, amino acids 364 to 370 of SEQ ID NO:2) is identical to the human sequence. The mouse sequence for the latter epitope (RGNPKP, SEQ ID NO:9, amino acids 308 to 313 of SEQ ID NO:2) differs by one amino acid.

As shown in FIG. 16, the 29D7, 7F5, 11E1 and 19E12 monoclonal antibodies all recognize loop-3 of the IgG-1 segment of human TrkB (ENLVGED, SEQ ID NO:10, amino acids 269 to 275 of SEQ ID NO:1); and may also recognize loop-1 of the IgG-1 segment of human TrkB (AGDPVP, SEQ ID NO:11, amino acids 221 to 226 of SEQ ID NO:1). The mouse sequence for the former epitope (ENLVGED, SEQ ID NO:10, amino acids 269 to 275 of SEQ ID NO:2) is identical to the human sequence. The mouse sequence for the latter epitope (GGDPLP, SEQ ID NO:12, amino acids 221 to 226 of SEQ ID NO:2) differs by two amino acids.

Example 8

This example describes in vivo TrkB activation experiments that were performed with the anti-TrkB antibody 29D7. Briefly, pups at P7 received a 5 µl intracerebroventricular injection of 0.3 nmole of either anti-TrkB monoclonal antibody 29D7 or vehicle. Brain tissues were then dissected 1, 2, 6, 12 and 24 hours after injection. Tissues were lysed and equal amounts of protein samples (30 µg/lane) were separated by SDS-PAGE and subjected to immunoblotting with antibodies specific to proteins that are phosphorylated as a result of TrkB activation (phospho-ERK1/2 and phospho-AKT). Antibodies against β-actin were used as controls to verify equal loading of proteins. The results of FIG. 21 show that anti-TrkB monoclonal antibody 29D7 induced time-dependent phosphorylation of ERK1/2 and AKT (data from hippocampal and cortical samples are shown and are representative of results obtained from four other samples).

Figure 21:
FIG. 21 shows immunoblots of protein samples taken from normal mice after an intracerebroventricular injection of anti-TrkB antibody 29D7 (or vehicle as control). Samples were taken 1, 2, 6, 12 and 24 hours after injection. Samples were separated by SDS-PAGE and subjected to immunoblotting with antibodies specific to proteins that are phosphorylated as a result of TrkB activation (phospho-ERK1/2 and phospho-AKT). Antibodies against β-actin were used as controls to verify equal loading of proteins. The results show that anti-TrkB monoclonal antibody 29D7 induced time-dependent phosphorylation of ERK1/2 and AKT (data from hippocampal and cortical samples are shown and are representative of results obtained from four other samples).
Figure 22:
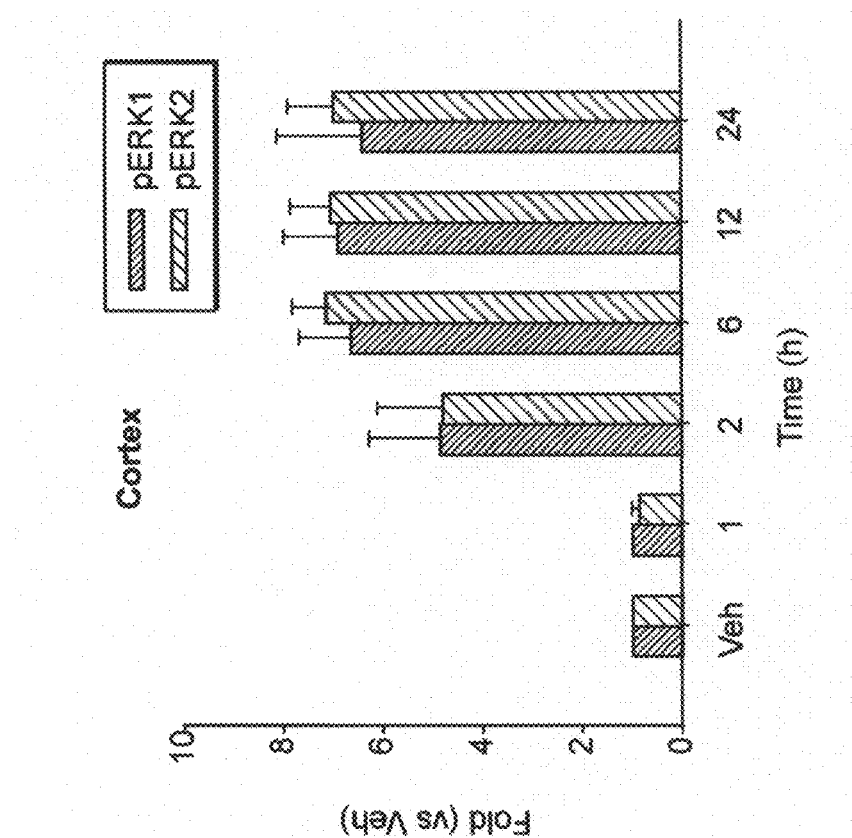
FIG. 22 is a densitometric quantification of the ERK phosphorylation shown in FIG. 21.
Figure 22:
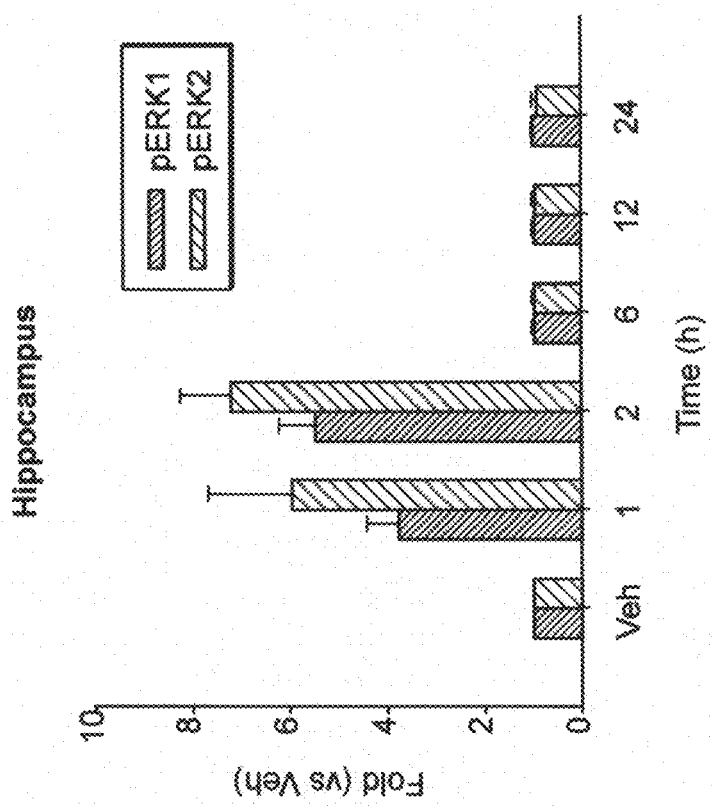
Figure 23:
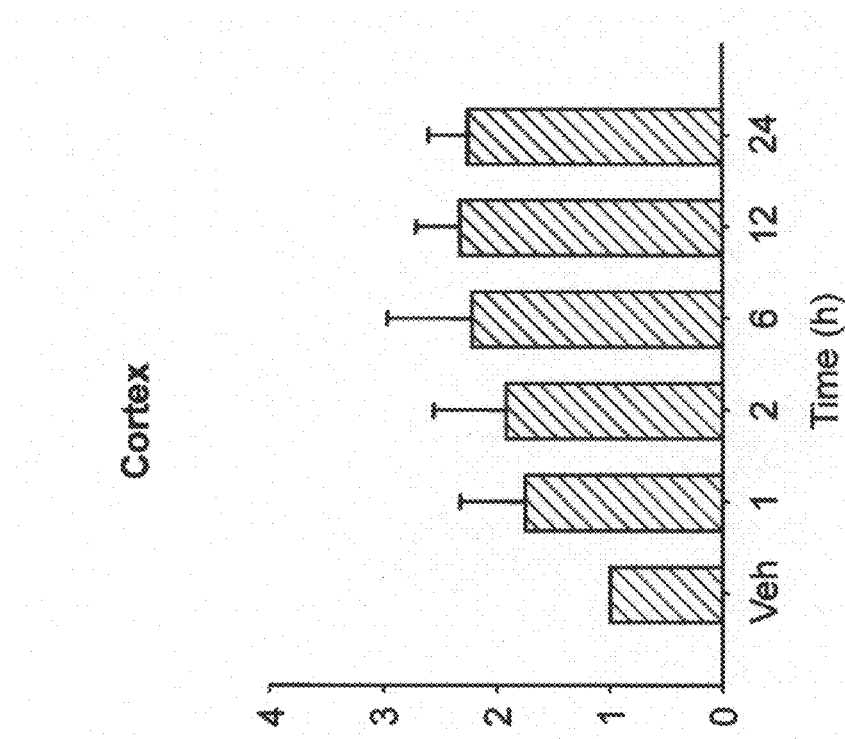
FIG. 23 is a densitometric quantification of the AKT phosphorylation shown in FIG. 21.
Figure 23:
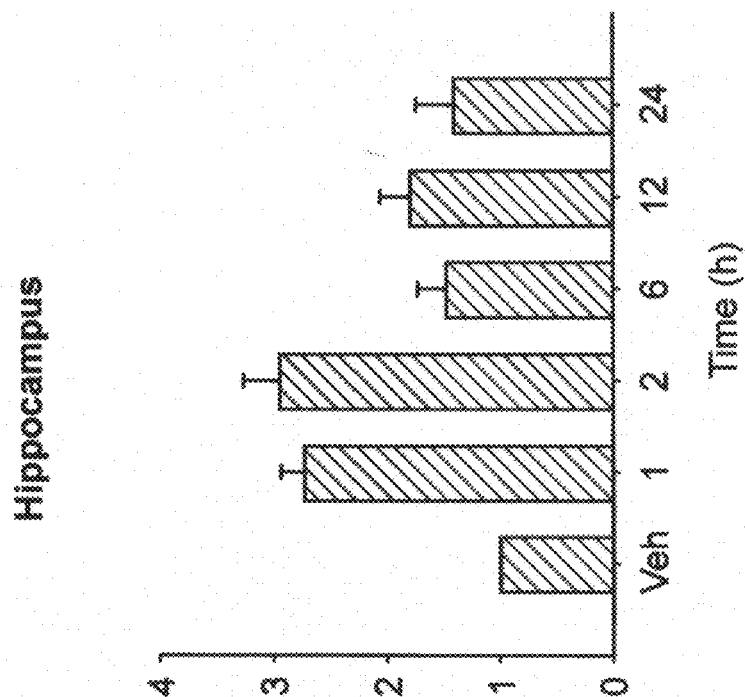
Figure 24:
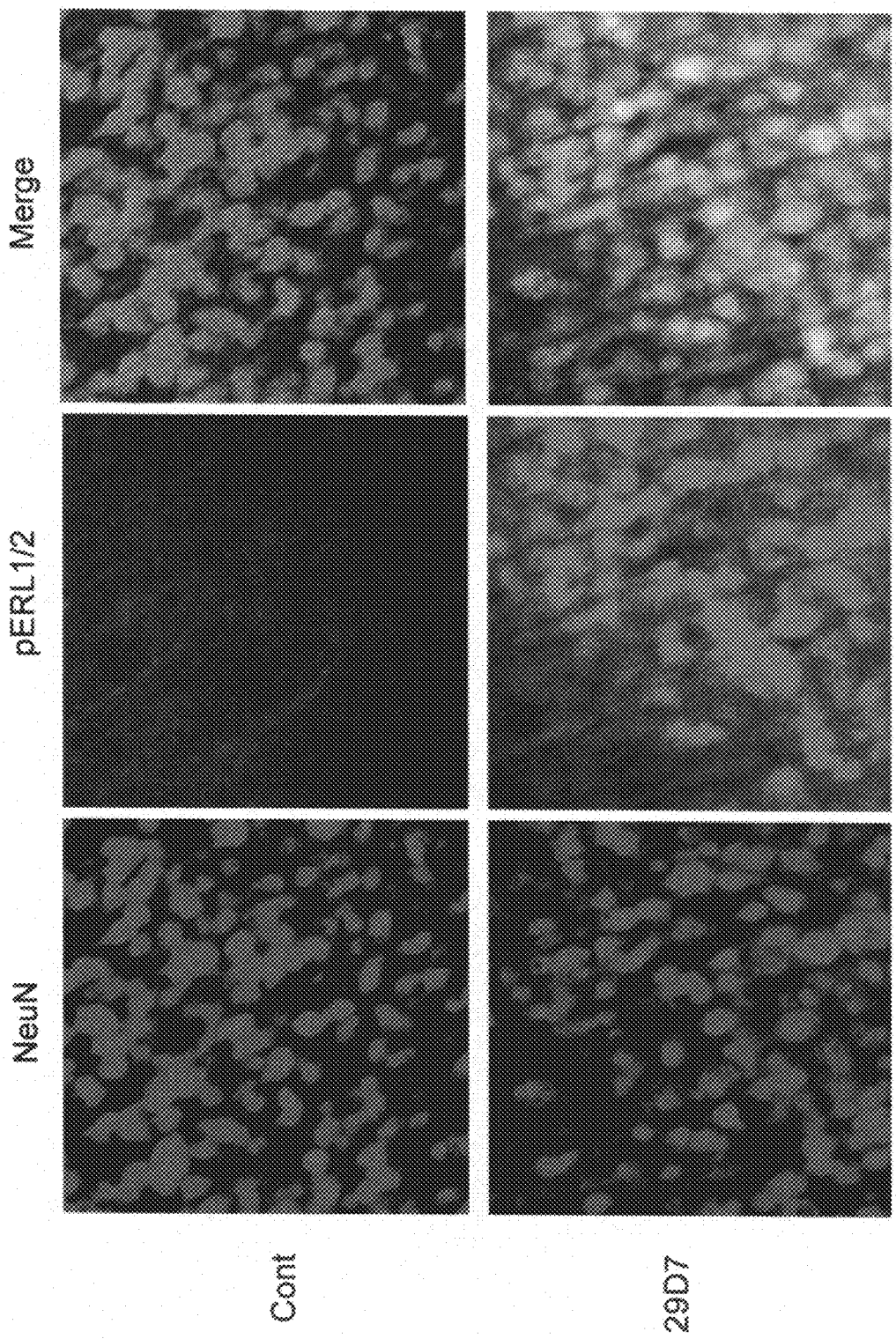
FIG. 24 shows vehicle and 29D7 treated brain tissues that have been fixed and immunoflourescently labeled with an antibody for the neuron-specific marker NeuN (left) and an anti-phospho-ERK1/2 antibody (center). The right hand figures show these two merged. ERK1/2 phosphorylation is significantly stronger in the 29D7 treated samples.
Figure 25:
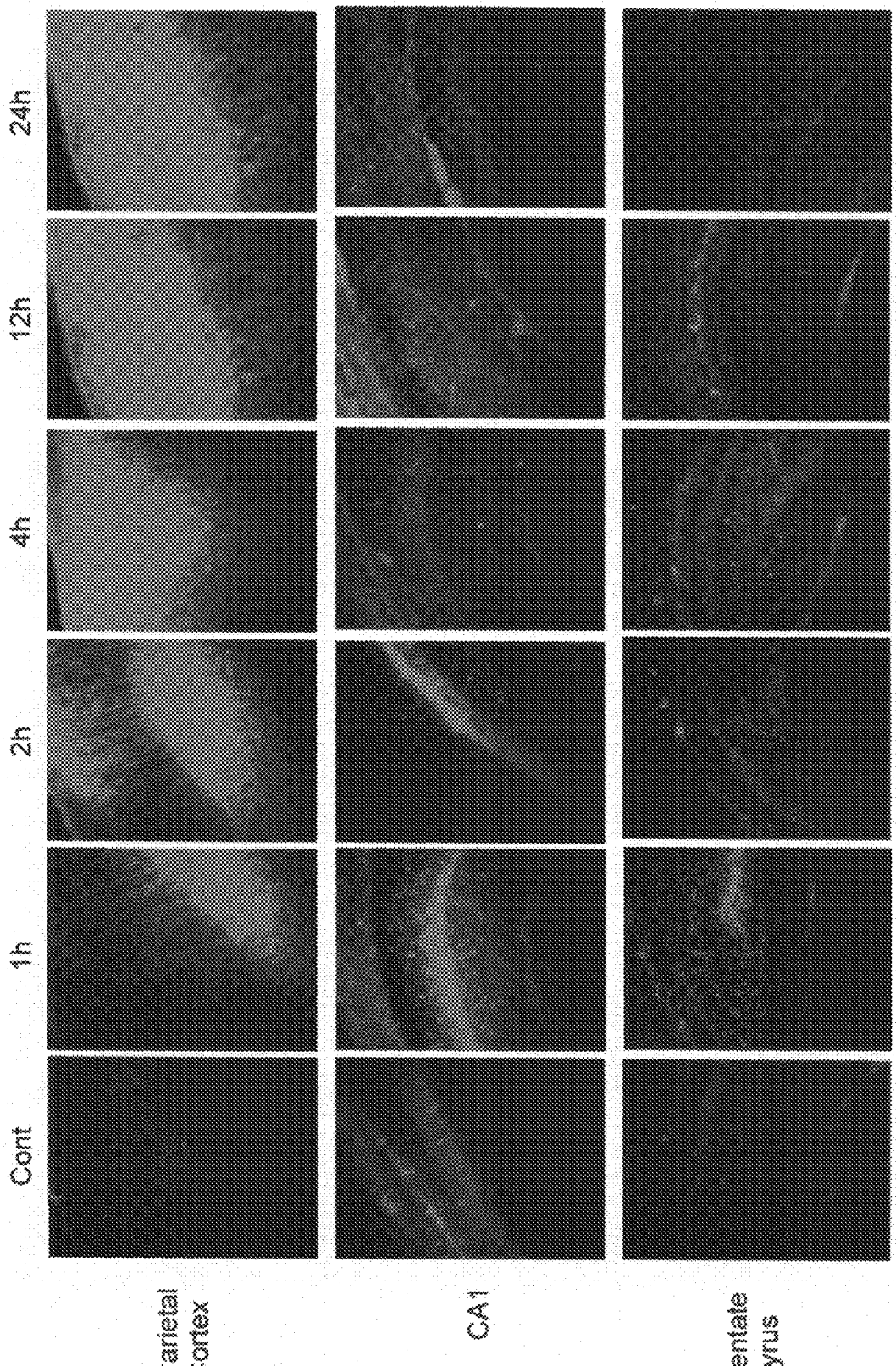
FIG. 25 shows the time-course of ERK1/2 activation in the cortical and hippocampal tissues following intracerebroventricular injection of anti-TrkB monoclonal antibody 29D7.

FIG. 22 is a densitometric quantification of the ERK phosphorylation shown in FIG. 21. FIG. 23 is a densitometric quantification of the AKT phosphorylation shown in FIG. 21. FIG. 24 shows vehicle and 29D7 treated brain tissues that have been fixed and immunoflourescently labeled with an antibody for the neuron-specific marker NeuN (left) and an anti-phospho-ERK1/2 antibody (center). The right hand figures show these two merged. ERK1/2 phosphorylation is significantly stronger in the 29D7 treated samples. FIG. 25 shows the time-course of ERK1/2 activation in the cortical and hippocampal tissues following intracerebroventricular injection of anti-TrkB monoclonal antibody 29D7.

Example 9

This example describes a MAG/myelin-induced neurite inhibition assay that was performed with the anti-TrkB antibody 29D7. Briefly, aliquots of 50 µl recombinant rat MAG (1-5) or purified rat myelin were added to 96 well flat bottom tissue culture plates and air-dried overnight at room temperature. The total amounts of MAG(1-5) or myelin were 0.25-0.5 µg per well, unless indicated differently. Next day, the MAG- or myelin-coated plates were treated with 50 µl of poly-D-lysine (17 µg/ml) for 1.5 hours, followed by incubation with a media containing 10% FBS for 1 hour at 37° C. After aspiration of the media, rat CGN cells were plated at a density of 8,000 cells/well in B27-supplemented Neurobasal growth media containing 200 mM L-Glutamine, 2 M KCl, and 100 U/ml penicillin and streptomycin. When indicated, treatment reagents were added at the time of cell plating. Neurons were grown in a 37° C. incubator equilibrated with 5% $CO_2$. Approximately 20 hours post plating, cells were fixed with 4% paraformaldehyde and proceeded for Tuj1 staining. Cells were permeabilized with 0.2% Triton X/PBS (TPBS) for 5 minutes at room temperature followed by incubation with 1.5% normal goat serum in TPBS (S-TPBS) for 30 minutes to block non-specific binding. An aliquot of anti-Neuronal Class III b-Tubulin monoclonal antibody (Tuj1, 1:1000; Covance # MMS-435P) was added to the cells. After 1 hour incubation at room temperature, unbound antibodies were washed with PBS three times and an aliquot of Alexa Fluor 488 mouse anti-goat IgG antibody (1:500, Molecular Probe # A-11001) was added to visualize the signals. Hoechst 33342 (Molecular Probe # H-3570, 2 µg/ml) was included to label the nucleus. After washing, plates were sealed and analyzed for neurite growth using a Cellomics array scan. Typically around 300 cells from 9 fields were analyzed per well and each treatment was conducted in quadruplets.

Figure 26:
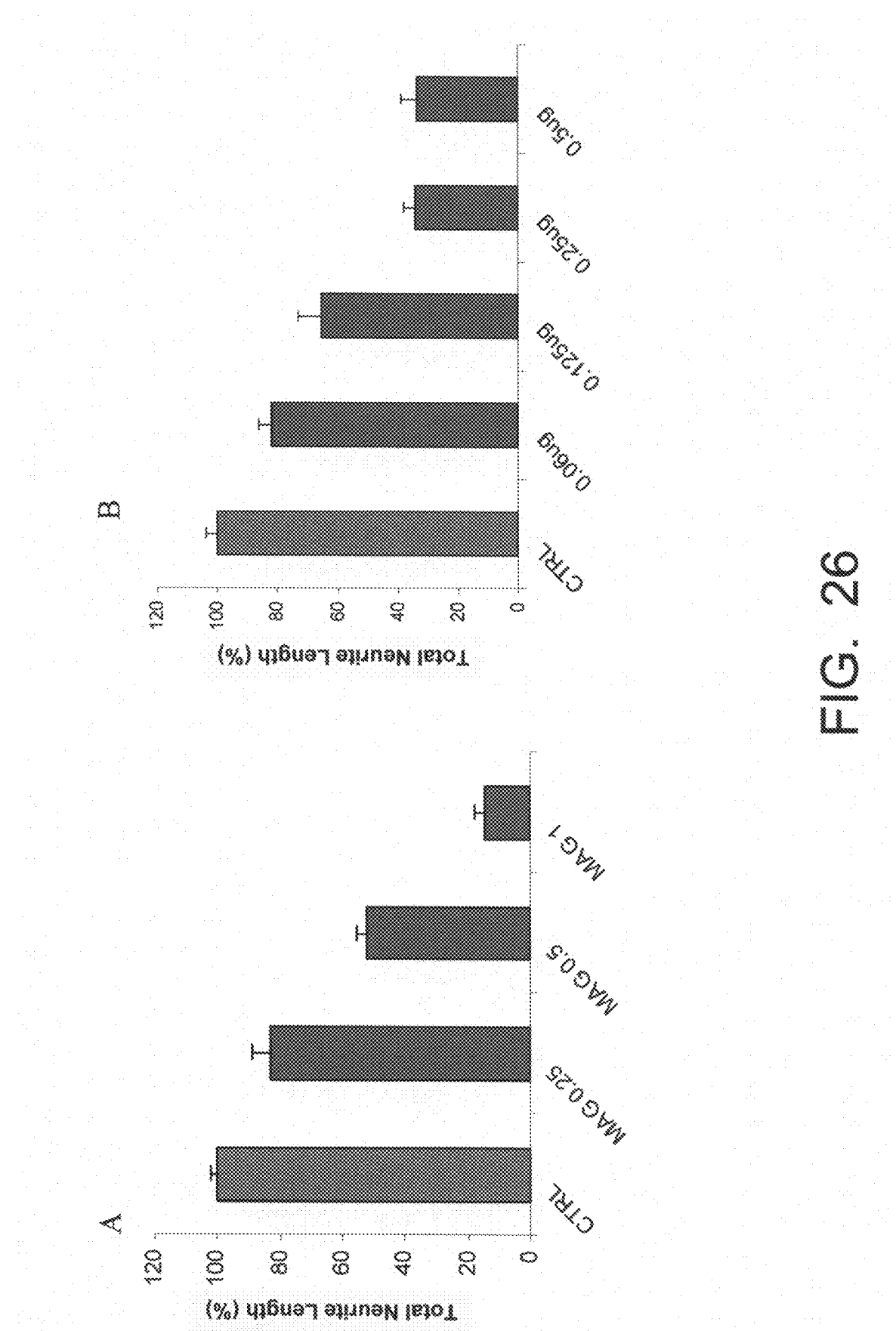
FIG. 26 shows the dose-dependent inhibition of neurite outgrowth of primary cerebellar granule neurons caused by (A) MAG and (B) myelin.

MAG and myelin inhibit neurite outgrowth of primary cerebellar granule neurons in cultures. Increasing concentrations of recombinant rat MAG(1-5) or purified rat myelin were coated on 96 well tissue culture plates and the neurite extension of primary neurons were measured at 20 hours as described above. As shown in FIG. 26, (A) MAG and (B) myelin resulted in dose-dependent inhibition of neurite outgrowth.

Figure 27:
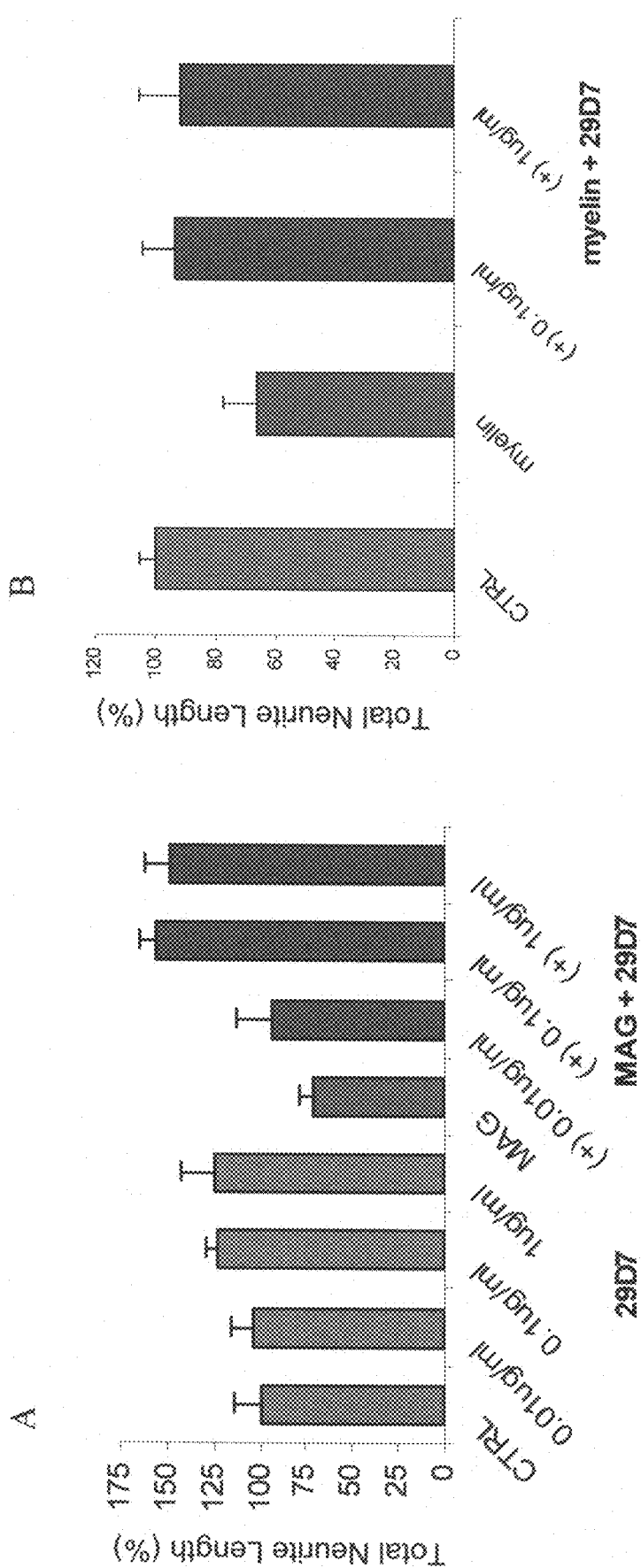
FIG. 27 shows the reversal of (A) MAG- and (B) myelin-mediated neurite inhibition that is caused by anti-TrkB monoclonal antibody 29D7.

CGN neurons were then plated on either MAG or myelin-coated plates with control or with a range of concentrations of the TrkB antibody 29D7. Neurite extension was measured 20 hours post-treatment. As shown in FIG. 27, 29D7 led to reversal of (A) MAG- and (B) myelin-mediated neurite inhibition.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

We claim:

1. An isolated monoclonal antibody that binds human TrkB, wherein the monoclonal antibody comprises complementarity-determining regions (CDRs) of an antibody produced by a hybridoma having ATCC patent deposit designation PTA-6949.

2. The monoclonal antibody of claim 1, wherein the binding with human TrkB has an $ED_{50}$ in the range of about 10 pM to about 500 nM.

3. The monoclonal antibody of claim 1, wherein the monoclonal antibody activates human TrkB with an $EC_{50}$ in the range of about 10 pM to about 500 nM.

4. The monoclonal antibody of claim 1, wherein the monoclonal antibody does not bind and/or does not activate human TrkA.

5. The monoclonal antibody of claim 4, wherein the monoclonal antibody exhibits no detectable binding with human TrkA and/or does not cause any detectable activation of human TrkA at antibody concentrations above about 1 nM.

6. The monoclonal antibody of claim 4, wherein the monoclonal antibody does not bind and/or does not activate human TrkC.

7. The monoclonal antibody of claim 1, wherein the monoclonal antibody does not bind and/or does not activate human TrkC.

8. The monoclonal antibody of claim 7, wherein the monoclonal antibody exhibits no detectable binding with human TrkC and/or does not cause any detectable activation of human TrkC at antibody concentrations above about 1 nM.

9. The monoclonal antibody of claim 1, wherein the monoclonal antibody blocks the binding between BDNF and human TrkB.

10. The monoclonal antibody of claim 9, wherein the monoclonal antibody blocks the binding between BDNF and human TrkB with an $IC_{50}$ in the range of about 100 pM to about 500 nM.

11. The monoclonal antibody of claim 1, wherein the monoclonal antibody has an IgG1 isotype.

12. The monoclonal antibody of claim 1, wherein the monoclonal antibody has an IgG2a isotype.

13. The monoclonal antibody of claim 1, wherein the monoclonal antibody has an IgG2b isotype.

14. The monoclonal antibody of claim 1, wherein the monoclonal antibody binds and/or activates murine TrkB.

15. The monoclonal antibody of claim 14, wherein the binding with murine TrkB has an $ED_{50}$ in the range of about 10 pM to about 500 nM.

16. The monoclonal antibody of claim 1, wherein the monoclonal antibody binds an epitope of human TrkB with the sequence ENLVGED (SEQ ID NO:10).

17. The monoclonal antibody of claim 16, wherein the monoclonal antibody further binds an epitope of human TrkB with the sequence AGDPVP (SEQ ID NO:11).

18. A hybridoma that produces the monoclonal antibody according to claim 1.

19. A method for detecting the presence of human TrkB in a sample, the method comprising:
combining a monoclonal antibody of claim 1 with a sample that includes an amount of human TrkB under conditions that allow specific binding between the monoclonal antibody and human TrkB; and
detecting the specific binding, thereby indicating the presence of human TrkB in the sample.

20. A method of obtaining purified human TrkB, the method comprising:
combining a monoclonal antibody of claim 1 with a sample that includes an amount of human TrkB under conditions that allow specific binding between the monoclonal antibody and human TrkB, thereby producing an antibody-TrkB complex;
separating the antibody-human TrkB complex from the remainder of the sample; and
separating the antibody from human TrkB, thereby obtaining purified human TrkB.

21. The monoclonal antibody of claim 1, wherein the monoclonal antibody comprises constant domains derived from a human antibody.

22. The monoclonal antibody of claim 1, wherein the monoclonal antibody comprises framework regions derived from a human antibody.

23. The monoclonal antibody of claim 1, wherein the monoclonal antibody comprises CDRs of a heavy chain variable region of an antibody produced by a hybridoma having ATCC patent deposit designation PTA-6949.

24. The monoclonal antibody of claim 1, wherein the monoclonal antibody comprises CDRs of a light chain variable region of an antibody produced by a hybridoma having ATCC patent deposit designation PTA-6949.

25. The monoclonal antibody of claim 1, wherein the monoclonal antibody comprises CDRs of a heavy chain variable region and a light chain variable region of an antibody produced by a hybridoma having ATCC patent deposit designation PTA-6949.

26. An isolated monoclonal antibody that is produced from the hybridoma deposited with the ATCC on Aug. 18, 2005 and having ATCC patent deposit designation PTA-6949.

27. A hybridoma deposited with the ATCC on Aug. 18, 2005 and having ATCC patent deposit designation PTA-6949.

* * * * *

SEQUENCE LISTING

```
<160> NUMBER OF SEQ ID NOS: 13

<210> SEQ ID NO 1
<211> LENGTH: 838
<212> TYPE: PRT
<213> ORGANISM: Artificial
<220> FEATURE:
<223> OTHER INFORMATION: Human - (homo sapiens) TrkB

<400> SEQUENCE: 1

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30

Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
```

-continued

```
                260                 265                 270
Gly Glu Asp Gln Asp Ser Val Asn Leu Thr Val His Phe Ala Pro Thr
            275                 280                 285
Ile Thr Phe Leu Glu Ser Pro Thr Ser Asp His His Trp Cys Ile Pro
290                 295                 300
Phe Thr Val Lys Gly Asn Pro Lys Pro Ala Leu Gln Trp Phe Tyr Asn
305                 310                 315                 320
Gly Ala Ile Leu Asn Glu Ser Lys Tyr Ile Cys Thr Lys Ile His Val
                325                 330                 335
Thr Asn His Thr Glu Tyr His Gly Cys Leu Gln Leu Asp Asn Pro Thr
            340                 345                 350
His Met Asn Asn Gly Asp Tyr Thr Leu Ile Ala Lys Asn Glu Tyr Gly
            355                 360                 365
Lys Asp Glu Lys Gln Ile Ser Ala His Phe Met Gly Trp Pro Gly Ile
            370                 375                 380
Asp Asp Gly Ala Asn Pro Asn Tyr Pro Asp Val Ile Tyr Glu Asp Tyr
385                 390                 395                 400
Gly Thr Ala Ala Asn Asp Ile Gly Asp Thr Thr Asn Arg Ser Asn Glu
                405                 410                 415
Ile Pro Ser Thr Asp Val Thr Asp Lys Thr Gly Arg Glu His Leu Ser
            420                 425                 430
Val Tyr Ala Val Val Val Ile Ala Ser Val Val Gly Phe Cys Leu Leu
            435                 440                 445
Val Met Leu Phe Leu Leu Lys Leu Ala Arg His Ser Lys Phe Gly Met
450                 455                 460
Lys Asp Phe Ser Trp Phe Gly Phe Gly Lys Val Lys Ser Arg Gln Gly
465                 470                 475                 480
Val Gly Pro Ala Ser Val Ile Ser Asn Asp Asp Ser Ala Ser Pro
                485                 490                 495
Leu His His Ile Ser Asn Gly Ser Asn Thr Pro Ser Ser Glu Gly
            500                 505                 510
Gly Pro Asp Ala Val Ile Ile Gly Met Thr Lys Ile Pro Val Ile Glu
            515                 520                 525
Asn Pro Gln Tyr Phe Gly Ile Thr Asn Ser Gln Leu Lys Pro Asp Thr
            530                 535                 540
Phe Val Gln His Ile Lys Arg His Asn Ile Val Leu Lys Arg Glu Leu
545                 550                 555                 560
Gly Glu Gly Ala Phe Gly Lys Val Phe Leu Ala Glu Cys Tyr Asn Leu
                565                 570                 575
Cys Pro Glu Gln Asp Lys Ile Leu Val Ala Val Lys Thr Leu Lys Asp
            580                 585                 590
Ala Ser Asp Asn Ala Arg Lys Asp Phe His Arg Glu Ala Glu Leu Leu
            595                 600                 605
Thr Asn Leu Gln His Glu His Ile Val Lys Phe Tyr Gly Val Cys Val
            610                 615                 620
Glu Gly Asp Pro Leu Ile Met Val Phe Glu Tyr Met Lys His Gly Asp
625                 630                 635                 640
Leu Asn Lys Phe Leu Arg Ala His Gly Pro Asp Ala Val Leu Met Ala
            645                 650                 655
Glu Gly Asn Pro Pro Thr Glu Leu Thr Gln Ser Gln Met Leu His Ile
            660                 665                 670
Ala Gln Gln Ile Ala Ala Gly Met Val Tyr Leu Ala Ser Gln His Phe
            675                 680                 685
```

```
Val His Arg Asp Leu Ala Thr Arg Asn Cys Leu Val Gly Glu Asn Leu
    690                 695                 700

Leu Val Lys Ile Gly Asp Phe Gly Met Ser Arg Asp Val Tyr Ser Thr
705                 710                 715                 720

Asp Tyr Tyr Arg Val Gly Gly His Thr Met Leu Pro Ile Arg Trp Met
                725                 730                 735

Pro Pro Glu Ser Ile Met Tyr Arg Lys Phe Thr Thr Glu Ser Asp Val
            740                 745                 750

Trp Ser Leu Gly Val Val Leu Trp Glu Ile Phe Thr Tyr Gly Lys Gln
        755                 760                 765

Pro Trp Tyr Gln Leu Ser Asn Asn Glu Val Ile Glu Cys Ile Thr Gln
    770                 775                 780

Gly Arg Val Leu Gln Arg Pro Arg Thr Cys Pro Gln Glu Val Tyr Glu
785                 790                 795                 800

Leu Met Leu Gly Cys Trp Gln Arg Glu Pro His Met Arg Lys Asn Ile
                805                 810                 815

Lys Gly Ile His Thr Leu Leu Gln Asn Leu Ala Lys Ala Ser Pro Val
            820                 825                 830

Tyr Leu Asp Ile Leu Gly
        835

<210> SEQ ID NO 2
<211> LENGTH: 821
<212> TYPE: PRT
<213> ORGANISM: Artificial
<220> FEATURE:
<223> OTHER INFORMATION: murine (Mus musculus) TrkB

<400> SEQUENCE: 2

Met Ser Pro Trp Leu Lys Trp His Gly Pro Ala Met Ala Arg Leu Trp
1               5                   10                  15

Gly Leu Cys Leu Leu Val Leu Gly Phe Trp Arg Ala Ser Leu Ala Cys
            20                  25                  30

Pro Thr Ser Cys Lys Cys Ser Ser Ala Arg Ile Trp Cys Thr Glu Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Leu Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala Tyr Lys Ala Phe Leu
            100                 105                 110

Lys Asn Ser Asn Leu Arg His Ile Asn Phe Thr Arg Asn Lys Leu Thr
        115                 120                 125

Ser Leu Ser Arg Arg His Phe Arg His Leu Asp Leu Ser Asp Leu Ile
    130                 135                 140

Leu Thr Gly Asn Pro Phe Thr Cys Ser Cys Asp Ile Met Trp Leu Lys
145                 150                 155                 160

Thr Leu Gln Glu Thr Lys Ser Ser Pro Asp Thr Gln Asp Leu Tyr Cys
                165                 170                 175

Leu Asn Glu Ser Ser Lys Asn Met Pro Leu Ala Asn Leu Gln Ile Pro
            180                 185                 190

Asn Cys Gly Leu Pro Ser Ala Arg Leu Ala Ala Pro Asn Leu Thr Val
        195                 200                 205
```

```
Glu Glu Gly Lys Ser Val Thr Leu Ser Cys Ser Val Gly Asp Pro
    210                 215                 220

Leu Pro Thr Leu Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Arg Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Met Ala Lys Asn Glu Tyr Gly
        355                 360                 365

Lys Asp Glu Arg Gln Ile Ser Ala His Phe Met Gly Arg Pro Gly Val
    370                 375                 380

Asp Tyr Glu Thr Asn Pro Asn Tyr Pro Glu Val Leu Tyr Glu Asp Trp
385                 390                 395                 400

Thr Thr Pro Thr Asp Ile Gly Asp Thr Thr Asn Lys Ser Asn Glu Ile
                405                 410                 415

Pro Ser Thr Asp Val Ala Asp Gln Ser Asn Arg Glu His Leu Ser Val
            420                 425                 430

Tyr Ala Val Val Val Ile Ala Ser Val Val Gly Phe Cys Leu Leu Val
        435                 440                 445

Met Leu Leu Leu Leu Lys Leu Ala Arg His Ser Lys Phe Gly Met Lys
450                 455                 460

Gly Pro Ala Ser Val Ile Ser Asn Asp Asp Asp Ser Ala Ser Pro Leu
465                 470                 475                 480

His His Ile Ser Asn Gly Ser Asn Thr Pro Ser Ser Glu Gly Gly
                485                 490                 495

Pro Asp Ala Val Ile Ile Gly Met Thr Lys Ile Pro Val Ile Glu Asn
            500                 505                 510

Pro Gln Tyr Phe Gly Ile Thr Asn Ser Gln Leu Lys Pro Asp Thr Phe
        515                 520                 525

Val Gln His Ile Lys Arg His Asn Ile Val Leu Lys Arg Glu Leu Gly
    530                 535                 540

Glu Gly Ala Phe Gly Lys Val Phe Leu Ala Glu Cys Tyr Asn Leu Cys
545                 550                 555                 560

Pro Glu Gln Asp Lys Ile Leu Val Ala Val Lys Thr Leu Lys Asp Ala
                565                 570                 575

Ser Asp Asn Ala Arg Lys Asp Phe His Arg Glu Ala Glu Leu Leu Thr
            580                 585                 590

Asn Leu Gln His Glu His Ile Val Lys Phe Tyr Gly Val Cys Val Glu
        595                 600                 605

Gly Asp Pro Leu Ile Met Val Phe Glu Tyr Met Lys His Gly Asp Leu
    610                 615                 620
```

-continued

Asn Lys Phe Leu Arg Ala His Gly Pro Asp Ala Val Leu Met Ala Glu
625                 630                 635                 640

Gly Asn Pro Pro Thr Glu Leu Thr Gln Ser Gln Met Leu His Ile Ala
            645                 650                 655

Gln Gln Ile Ala Ala Gly Met Val Tyr Leu Ala Ser Gln His Phe Val
        660                 665                 670

His Arg Asp Leu Ala Thr Arg Asn Cys Leu Val Gly Glu Asn Leu Leu
    675                 680                 685

Val Lys Ile Gly Asp Phe Gly Met Ser Arg Asp Val Tyr Ser Thr Asp
690                 695                 700

Tyr Tyr Arg Val Gly Gly His Thr Met Leu Pro Ile Arg Trp Met Pro
705                 710                 715                 720

Pro Glu Ser Ile Met Tyr Arg Lys Phe Thr Thr Glu Ser Asp Val Trp
                725                 730                 735

Ser Leu Gly Val Val Leu Trp Glu Ile Phe Thr Tyr Gly Lys Gln Pro
            740                 745                 750

Trp Tyr Gln Leu Ser Asn Asn Glu Val Ile Glu Cys Ile Thr Gln Gly
        755                 760                 765

Arg Val Leu Gln Arg Pro Arg Thr Cys Pro Gln Glu Val Tyr Glu Leu
    770                 775                 780

Met Leu Gly Cys Trp Gln Arg Glu Pro His Thr Arg Lys Asn Ile Lys
785                 790                 795                 800

Ser Ile His Thr Leu Leu Gln Asn Leu Ala Lys Ala Ser Pro Val Tyr
                805                 810                 815

Leu Asp Ile Leu Gly
            820

<210> SEQ ID NO 3
<211> LENGTH: 821
<212> TYPE: PRT
<213> ORGANISM: Artificial
<220> FEATURE:
<223> OTHER INFORMATION: rat - (Rattus norvegicus) TrkB

<400> SEQUENCE: 3

Met Ser Pro Trp Pro Arg Trp His Gly Pro Ala Met Ala Arg Leu Trp
1               5                   10                  15

Gly Leu Cys Leu Leu Val Leu Gly Phe Trp Arg Ala Ser Leu Ala Cys
            20                  25                  30

Pro Met Ser Cys Lys Cys Ser Thr Thr Arg Ile Trp Cys Thr Glu Pro
        35                  40                  45

Ser Pro Gly Ile Val Ala Phe Pro Arg Leu Glu Pro Asn Ser Ile Asp
    50                  55                  60

Pro Glu Asn Ile Thr Glu Ile Leu Ile Ala Asn Gln Lys Arg Leu Glu
65                  70                  75                  80

Ile Ile Asn Glu Asp Asp Val Glu Ala Tyr Val Gly Leu Lys Asn Leu
                85                  90                  95

Thr Ile Val Asp Ser Gly Leu Lys Phe Val Ala Tyr Lys Ala Phe Leu
            100                 105                 110

Lys Asn Gly Asn Leu Arg His Ile Asn Phe Thr Arg Asn Lys Leu Thr
        115                 120                 125

Ser Leu Ser Arg Arg His Phe Arg His Leu Asp Leu Ser Asp Leu Ile
    130                 135                 140

Leu Thr Gly Asn Pro Phe Thr Cys Ser Cys Asp Ile Met Trp Leu Lys
145                 150                 155                 160

-continued

```
Thr Leu Gln Glu Thr Lys Ser Ser Pro Asp Thr Gln Asp Leu Tyr Cys
            165                 170                 175

Leu Asn Glu Ser Ser Lys Asn Thr Pro Leu Ala Asn Leu Gln Ile Pro
        180                 185                 190

Asn Cys Gly Leu Pro Ser Ala Arg Leu Ala Ala Pro Asn Leu Thr Val
    195                 200                 205

Glu Glu Gly Lys Ser Val Thr Ile Ser Cys Ser Val Gly Asp Pro
210                 215                 220

Leu Pro Thr Leu Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
            245                 250                 255

Ser Asp Asp Ser Gly Lys Gln Ile Ser Cys Val Ala Glu Asn Leu Val
        260                 265                 270

Gly Glu Asp Gln Asp Ser Val Asn Leu Thr Val His Phe Ala Pro Thr
    275                 280                 285

Ile Thr Phe Leu Glu Ser Pro Thr Ser Asp His His Trp Cys Ile Pro
290                 295                 300

Phe Thr Val Arg Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
            325                 330                 335

Thr Asn His Thr Glu Tyr His Gly Cys Leu Gln Leu Asp Asn Pro Thr
        340                 345                 350

His Met Asn Asn Gly Asp Tyr Thr Leu Met Ala Lys Asn Glu Tyr Gly
    355                 360                 365

Lys Asp Glu Arg Gln Ile Ser Ala His Phe Met Gly Arg Pro Gly Val
370                 375                 380

Asp Tyr Glu Thr Asn Pro Asn Tyr Pro Glu Val Leu Tyr Glu Asp Trp
385                 390                 395                 400

Thr Thr Pro Thr Asp Ile Gly Asp Thr Thr Asn Lys Ser Asn Glu Ile
            405                 410                 415

Pro Ser Thr Asp Val Ala Asp Gln Thr Asn Arg Glu His Leu Ser Val
        420                 425                 430

Tyr Ala Val Val Val Ile Ala Ser Val Val Gly Phe Cys Leu Leu Val
    435                 440                 445

Met Leu Leu Leu Leu Lys Leu Ala Arg His Ser Lys Phe Gly Met Lys
450                 455                 460

Gly Pro Ala Ser Val Ile Ser Asn Asp Asp Ser Ala Ser Pro Leu
465                 470                 475                 480

His His Ile Ser Asn Gly Ser Asn Thr Pro Ser Ser Glu Gly Gly
            485                 490                 495

Pro Asp Ala Val Ile Ile Gly Met Thr Lys Ile Pro Val Ile Glu Asn
        500                 505                 510

Pro Gln Tyr Phe Gly Ile Thr Asn Ser Gln Leu Lys Pro Asp Thr Phe
    515                 520                 525

Val Gln His Ile Lys Arg His Asn Ile Val Leu Lys Arg Glu Leu Gly
530                 535                 540

Glu Gly Ala Phe Gly Lys Val Phe Leu Ala Glu Cys Tyr Asn Leu Cys
545                 550                 555                 560

Pro Glu Gln Asp Lys Ile Leu Val Ala Val Lys Thr Leu Lys Asp Ala
            565                 570                 575

Ser Asp Asn Ala Arg Lys Asp Phe His Arg Glu Ala Glu Leu Leu Thr
```

-continued

```
                580                 585                 590
Asn Leu Gln His Glu His Ile Val Lys Phe Tyr Gly Val Cys Val Glu
            595                 600                 605

Gly Asp Pro Leu Ile Met Val Phe Glu Tyr Met Lys His Gly Asp Leu
        610                 615                 620

Asn Lys Phe Leu Arg Ala His Gly Pro Asp Ala Val Leu Met Ala Glu
625                 630                 635                 640

Gly Asn Pro Pro Thr Glu Leu Thr Gln Ser Gln Met Leu His Ile Ala
                645                 650                 655

Gln Gln Ile Ala Ala Gly Met Val Tyr Leu Ala Ser Gln His Phe Val
            660                 665                 670

His Arg Asp Leu Ala Thr Arg Asn Cys Leu Val Gly Glu Asn Leu Leu
        675                 680                 685

Val Lys Ile Gly Asp Phe Gly Met Ser Arg Asp Val Tyr Ser Thr Asp
    690                 695                 700

Tyr Tyr Arg Val Gly Gly His Thr Met Leu Pro Ile Arg Trp Met Pro
705                 710                 715                 720

Pro Glu Ser Ile Met Tyr Arg Lys Phe Thr Thr Glu Ser Asp Val Trp
                725                 730                 735

Ser Leu Gly Val Val Leu Trp Glu Ile Phe Thr Tyr Gly Lys Gln Pro
            740                 745                 750

Trp Tyr Gln Leu Ser Asn Asn Glu Val Ile Glu Cys Ile Thr Gln Gly
        755                 760                 765

Arg Val Leu Gln Arg Pro Arg Thr Cys Pro Gln Glu Val Tyr Glu Leu
    770                 775                 780

Met Leu Gly Cys Trp Gln Arg Glu Pro His Thr Arg Lys Asn Ile Lys
785                 790                 795                 800

Asn Ile His Thr Leu Leu Gln Asn Leu Ala Lys Ala Ser Pro Val Tyr
                805                 810                 815

Leu Asp Ile Leu Gly
            820

<210> SEQ ID NO 4
<211> LENGTH: 818
<212> TYPE: PRT
<213> ORGANISM: Artificial
<220> FEATURE:
<223> OTHER INFORMATION: chicken - (Gallus gallus) TrkB

<400> SEQUENCE: 4

Met Val Ser Trp Arg Arg Pro Gly Pro Gly Leu Ala Arg Leu Trp
1               5                   10                  15

Gly Leu Cys Cys Leu Val Leu Gly Cys Trp Arg Gly Ala Leu Gly Cys
            20                  25                  30

Pro Ala Ser Cys Arg Cys Ser Ser Trp Arg Ile Trp Cys Ser Glu Pro
        35                  40                  45

Val Pro Gly Ile Thr Ser Phe Pro Val Pro Gln Arg Ser Thr Glu Asp
    50                  55                  60

Asp Asn Val Thr Glu Ile Tyr Ile Ala Asn Gln Arg Lys Leu Glu Ser
65                  70                  75                  80

Ile Asn Asp Asn Glu Val Gly Phe Tyr Val Gly Leu Lys Asn Leu Thr
                85                  90                  95

Val Val Asp Ser Gly Leu Arg Phe Val Ser Arg Gln Ala Phe Val Lys
            100                 105                 110

Asn Ile Asn Leu Gln Tyr Ile Asn Leu Ser Arg Asn Lys Leu Ser Ser
```

-continued

```
            115                 120                 125
Leu Ser Lys Lys Pro Phe Arg His Leu Gly Leu Ser Asp Leu Ile Leu
        130                 135                 140
Val Asp Asn Pro Phe Lys Cys Ser Cys Glu Ile Met Trp Ile Lys Lys
145                 150                 155                 160
Phe Gln Glu Thr Lys Phe Tyr Thr Glu Ala Gln Asp Ile Tyr Cys Val
                165                 170                 175
Asp Asp Asn Asn Lys Arg Ile Ala Leu Met Asp Met Lys Val Pro Asn
                180                 185                 190
Cys Asp Leu Pro Ser Ala Asn Leu Ser Asn Tyr Asn Ile Thr Val Val
                195                 200                 205
Glu Gly Lys Ser Ile Thr Leu Tyr Cys Asp Thr Thr Gly Gly Pro Pro
        210                 215                 220
Pro Asn Val Ser Trp Val Leu Thr Asn Leu Val Ser Asn His Glu Ser
225                 230                 235                 240
Asp Thr Ser Lys Asn Pro Ala Ser Leu Thr Ile Lys Asn Val Ser Ser
                245                 250                 255
Met Asp Ser Gly Leu Trp Ile Ser Cys Val Ala Glu Asn Ile Val Gly
                260                 265                 270
Glu Val Gln Thr Ser Ala Glu Leu Thr Val Phe Phe Ala Pro Asn Ile
                275                 280                 285
Thr Phe Ile Glu Ser Pro Thr Pro Asp His His Trp Cys Ile Pro Phe
        290                 295                 300
Thr Val Lys Gly Asn Pro Lys Pro Thr Leu Gln Trp Phe Tyr Glu Gly
305                 310                 315                 320
Ala Ile Leu Asn Glu Ser Glu Tyr Ile Cys Thr Lys Ile His Val Ile
                325                 330                 335
Asn Gln Ser Glu Tyr His Gly Cys Leu Gln Leu Asp Asn Pro Thr His
                340                 345                 350
Leu Asn Asn Gly Ala Tyr Thr Leu Leu Ala Lys Asn Glu Tyr Gly Glu
        355                 360                 365
Asp Glu Lys Arg Val Asp Ala His Phe Met Ser Val Pro Gly Asp Gly
        370                 375                 380
Ser Gly Pro Ile Val Asp Pro Asp Val Tyr Glu Tyr Glu Thr Thr Pro
385                 390                 395                 400
Asn Asp Leu Gly Asp Thr Thr Asn Asn Ser Asn Gln Ile Thr Ser Pro
                405                 410                 415
Asp Val Ser Asn Lys Glu Asn Glu Asp Ser Ile Thr Val Tyr Val Val
                420                 425                 430
Val Gly Ile Ala Ala Leu Val Cys Thr Gly Leu Val Ile Met Leu Ile
        435                 440                 445
Ile Leu Lys Phe Gly Arg His Ser Lys Phe Gly Met Lys Gly Pro Ser
        450                 455                 460
Ser Val Ile Ser Asn Asp Asp Ser Ala Ser Pro Leu His His Ile
465                 470                 475                 480
Ser Asn Gly Ser Asn Thr Pro Ser Ser Glu Gly Gly Pro Asp Ala
                485                 490                 495
Val Ile Ile Gly Met Thr Lys Ile Pro Val Ile Glu Asn Pro Gln Tyr
                500                 505                 510
Phe Gly Ile Thr Asn Ser Gln Leu Lys Pro Asp Thr Phe Val Gln His
        515                 520                 525
Ile Lys Arg His Asn Ile Val Leu Lys Arg Glu Leu Gly Glu Gly Ala
        530                 535                 540
```

```
Phe Gly Lys Val Phe Leu Ala Glu Cys Tyr Asn Leu Cys Pro Glu Gln
545                 550                 555                 560

Asp Lys Ile Leu Val Ala Val Lys Thr Leu Lys Asp Ala Ser Asp Asn
                565                 570                 575

Ala Arg Lys Asp Phe His Arg Glu Ala Glu Leu Leu Thr Asn Leu Gln
                580                 585                 590

His Glu His Ile Val Lys Phe Tyr Gly Val Cys Val Glu Gly Asp Pro
                595                 600                 605

Leu Ile Met Val Phe Glu Tyr Met Lys His Gly Asp Leu Asn Lys Phe
610                 615                 620

Leu Arg Ala His Gly Pro Asp Ala Val Leu Met Ala Glu Gly Asn Arg
625                 630                 635                 640

Pro Ala Glu Leu Thr Gln Ser Gln Met Leu His Ile Ala Gln Gln Ile
                645                 650                 655

Ala Ala Gly Met Val Tyr Leu Ala Ser Gln His Phe Val His Arg Asp
                660                 665                 670

Leu Ala Thr Arg Asn Cys Leu Val Gly Glu Asn Leu Leu Val Lys Ile
                675                 680                 685

Gly Asp Phe Gly Met Ser Arg Asp Val Tyr Ser Thr Asp Tyr Tyr Arg
690                 695                 700

Val Gly Gly His Thr Met Leu Pro Ile Arg Trp Met Pro Pro Glu Ser
705                 710                 715                 720

Ile Met Tyr Arg Lys Phe Thr Thr Glu Ser Asp Val Trp Ser Leu Gly
                725                 730                 735

Val Val Leu Trp Glu Ile Phe Thr Tyr Gly Lys Gln Pro Trp Tyr Gln
                740                 745                 750

Leu Ser Asn Asn Glu Val Ile Glu Cys Ile Thr Gln Gly Arg Val Leu
                755                 760                 765

Gln Arg Pro Arg Thr Cys Pro Lys Glu Val Tyr Asp Leu Met Leu Gly
                770                 775                 780

Cys Trp Gln Arg Glu Pro His Met Arg Leu Asn Ile Lys Glu Ile His
785                 790                 795                 800

Ser Leu Leu Gln Asn Leu Ala Lys Ala Ser Pro Val Tyr Leu Asp Ile
                805                 810                 815

Leu Gly

<210> SEQ ID NO 5
<211> LENGTH: 796
<212> TYPE: PRT
<213> ORGANISM: Artificial
<220> FEATURE:
<223> OTHER INFORMATION: human - (Homo sapiens) TrkA

<400> SEQUENCE: 5

Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly
                20                  25                  30

Ala Ala Pro Cys Pro Asp Ala Cys Cys Pro His Gly Ser Ser Gly Leu
            35                  40                  45

Arg Cys Thr Arg Asp Gly Ala Leu Asp Ser Leu His His Leu Pro Gly
        50                  55                  60

Ala Glu Asn Leu Thr Glu Leu Tyr Ile Glu Asn Gln Gln His Leu Gln
65                  70                  75                  80
```

```
His Leu Glu Leu Arg Asp Leu Arg Gly Leu Gly Glu Leu Arg Asn Leu
                85                  90                  95

Thr Ile Val Lys Ser Gly Leu Arg Phe Val Ala Pro Asp Ala Phe His
            100                 105                 110

Phe Thr Pro Arg Leu Ser Arg Leu Asn Leu Ser Phe Asn Ala Leu Glu
        115                 120                 125

Ser Leu Ser Trp Lys Thr Val Gln Gly Leu Ser Leu Gln Glu Leu Val
    130                 135                 140

Leu Ser Gly Asn Pro Leu His Cys Ser Cys Ala Leu Arg Trp Leu Gln
145                 150                 155                 160

Arg Trp Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
                180                 185                 190

Val Pro Thr Leu Lys Val Gln Val Pro Asn Ala Ser Val Asp Val Gly
            195                 200                 205

Asp Asp Val Leu Leu Arg Cys Gln Val Glu Gly Arg Gly Leu Glu Gln
        210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
                260                 265                 270

Arg Ala Glu Val Ser Val Gln Val Asn Val Ser Phe Pro Ala Ser Val
            275                 280                 285

Gln Leu His Thr Ala Val Glu Met His His Trp Cys Ile Pro Phe Ser
    290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
                340                 345                 350

His Val Asn Asn Gly Asn Tyr Thr Leu Leu Ala Ala Asn Pro Phe Gly
            355                 360                 365

Gln Ala Ser Ala Ser Ile Met Ala Ala Phe Met Asp Asn Pro Phe Glu
    370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
                405                 410                 415

Gly Val Ser Val Ala Val Gly Leu Ala Val Phe Ala Cys Leu Phe Leu
                420                 425                 430

Ser Thr Leu Leu Leu Val Leu Asn Lys Cys Gly Arg Arg Asn Lys Phe
    435                 440                 445

Gly Ile Asn Arg Pro Ala Val Leu Ala Pro Glu Asp Gly Leu Ala Met
    450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
                485                 490                 495

Phe Ser Asp Ala Cys Val His His Ile Lys Arg Arg Asp Ile Val Leu
```

-continued

```
                500             505             510
Lys Trp Glu Leu Gly Glu Gly Ala Phe Gly Lys Val Phe Leu Ala Glu
            515                 520                 525

Cys His Asn Leu Leu Pro Glu Gln Asp Lys Met Leu Val Ala Val Lys
        530                 535                 540

Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
                565                 570                 575

Gly Val Cys Thr Glu Gly Arg Pro Leu Leu Met Val Phe Glu Tyr Met
            580                 585                 590

Arg His Gly Asp Leu Asn Arg Phe Leu Arg Ser His Gly Pro Asp Ala
        595                 600                 605

Lys Leu Leu Ala Gly Gly Glu Asp Val Ala Pro Gly Pro Leu Gly Leu
610                 615                 620

Gly Gln Leu Leu Ala Val Ala Ser Gln Val Ala Ala Gly Met Val Tyr
625                 630                 635                 640

Leu Ala Gly Leu His Phe Val His Arg Asp Leu Ala Thr Arg Asn Cys
                645                 650                 655

Leu Val Gly Gln Gly Leu Val Val Lys Ile Gly Asp Phe Gly Met Ser
            660                 665                 670

Arg Asp Ile Tyr Ser Thr Asp Tyr Tyr Arg Val Gly Gly Arg Thr Met
        675                 680                 685

Leu Pro Ile Arg Trp Met Pro Glu Ser Ile Leu Tyr Arg Lys Phe
690                 695                 700

Thr Thr Glu Ser Asp Val Trp Ser Phe Gly Val Val Leu Trp Glu Ile
705                 710                 715                 720

Phe Thr Tyr Gly Lys Gln Pro Trp Tyr Gln Leu Ser Asn Thr Glu Ala
                725                 730                 735

Ile Asp Cys Ile Thr Gln Gly Arg Glu Leu Glu Arg Pro Arg Ala Cys
            740                 745                 750

Pro Pro Glu Val Tyr Ala Ile Met Arg Gly Cys Trp Gln Arg Glu Pro
        755                 760                 765

Gln Gln Arg His Ser Ile Lys Asp Val His Ala Arg Leu Gln Ala Leu
770                 775                 780

Ala Gln Ala Pro Pro Val Tyr Leu Asp Val Leu Gly
785                 790                 795
```

<210> SEQ ID NO 6
<211> LENGTH: 839
<212> TYPE: PRT
<213> ORGANISM: Artificial
<220> FEATURE:
<223> OTHER INFORMATION: human (Homo sapiens) TrkC

<400> SEQUENCE: 6

```
Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
        35                  40                  45

Asp Asp Gly Asn Leu Phe Pro Leu Leu Glu Gly Gln Asp Ser Gly Asn
    50                  55                  60

Ser Asn Gly Asn Ala Asn Ile Asn Ile Thr Asp Ile Ser Arg Asn Ile
```

-continued

```
                65                  70                  75                  80
Thr Ser Ile His Ile Glu Asn Trp Arg Ser Leu His Thr Leu Asn Ala
                    85                  90                  95
Val Asp Met Glu Leu Tyr Thr Gly Leu Gln Lys Leu Thr Ile Lys Asn
                100                 105                 110
Ser Gly Leu Arg Ser Ile Gln Pro Arg Ala Phe Ala Lys Asn Pro His
                115                 120                 125
Leu Arg Tyr Ile Asn Leu Ser Ser Asn Arg Leu Thr Thr Leu Ser Trp
    130                 135                 140
Gln Leu Phe Gln Thr Leu Ser Leu Arg Glu Leu Gln Leu Glu Gln Asn
145                 150                 155                 160
Phe Phe Asn Cys Ser Cys Asp Ile Arg Trp Met Gln Leu Trp Gln Glu
                165                 170                 175
Gln Gly Glu Ala Lys Leu Asn Ser Gln Asn Leu Tyr Cys Ile Asn Ala
                180                 185                 190
Asp Gly Ser Gln Leu Pro Leu Phe Arg Met Asn Ile Ser Gln Cys Asp
                195                 200                 205
Leu Pro Glu Ile Ser Val Ser His Val Asn Leu Thr Val Arg Glu Gly
    210                 215                 220
Asp Asn Ala Val Ile Thr Cys Asn Gly Ser Gly Ser Pro Leu Pro Asp
225                 230                 235                 240
Val Asp Trp Ile Val Thr Gly Leu Gln Ser Ile Asn Thr His Gln Thr
                245                 250                 255
Asn Leu Asn Trp Thr Asn Val His Ala Ile Asn Leu Thr Leu Val Asn
                260                 265                 270
Val Thr Ser Glu Asp Asn Gly Phe Thr Leu Thr Cys Ile Ala Glu Asn
                275                 280                 285
Val Val Gly Met Ser Asn Ala Ser Val Ala Leu Thr Val Tyr Tyr Pro
                290                 295                 300
Pro Arg Val Val Ser Leu Glu Glu Pro Glu Leu Arg Leu Glu His Cys
305                 310                 315                 320
Ile Glu Phe Val Val Arg Gly Asn Pro Pro Thr Leu His Trp Leu
                325                 330                 335
His Asn Gly Gln Pro Leu Arg Glu Ser Lys Ile Ile His Val Glu Tyr
                340                 345                 350
Tyr Gln Glu Gly Glu Ile Ser Glu Gly Cys Leu Leu Phe Asn Lys Pro
                355                 360                 365
Thr His Tyr Asn Asn Gly Asn Tyr Thr Leu Ile Ala Lys Asn Pro Leu
    370                 375                 380
Gly Thr Ala Asn Gln Thr Ile Asn Gly His Phe Leu Lys Glu Pro Phe
385                 390                 395                 400
Pro Glu Ser Thr Asp Asn Phe Ile Leu Phe Asp Glu Val Ser Pro Thr
                405                 410                 415
Pro Pro Ile Thr Val Thr His Lys Pro Glu Glu Asp Thr Phe Gly Val
                420                 425                 430
Ser Ile Ala Val Gly Leu Ala Ala Phe Ala Cys Val Leu Leu Val Val
                435                 440                 445
Leu Phe Val Met Ile Asn Lys Tyr Gly Arg Arg Ser Lys Phe Gly Met
    450                 455                 460
Lys Gly Pro Val Ala Val Ile Ser Gly Glu Glu Asp Ser Ala Ser Pro
465                 470                 475                 480
Leu His His Ile Asn His Gly Ile Thr Thr Pro Ser Ser Leu Asp Ala
                485                 490                 495
```

```
Gly Pro Asp Thr Val Val Ile Gly Met Thr Arg Ile Pro Val Ile Glu
                500                 505                 510
Asn Pro Gln Tyr Phe Arg Gln Gly His Asn Cys His Lys Pro Asp Thr
            515                 520                 525
Tyr Val Gln His Ile Lys Arg Arg Asp Ile Val Leu Lys Arg Glu Leu
        530                 535                 540
Gly Glu Gly Ala Phe Gly Lys Val Phe Leu Ala Glu Cys Tyr Asn Leu
545                 550                 555                 560
Ser Pro Thr Lys Asp Lys Met Leu Val Ala Val Lys Ala Leu Lys Asp
                565                 570                 575
Pro Thr Leu Ala Ala Arg Lys Asp Phe Gln Arg Glu Ala Glu Leu Leu
            580                 585                 590
Thr Asn Leu Gln His Glu His Ile Val Lys Phe Tyr Gly Val Cys Gly
        595                 600                 605
Asp Gly Asp Pro Leu Ile Met Val Phe Glu Tyr Met Lys His Gly Asp
610                 615                 620
Leu Asn Lys Phe Leu Arg Ala His Gly Pro Asp Ala Met Ile Leu Val
625                 630                 635                 640
Asp Gly Gln Pro Arg Gln Ala Lys Gly Glu Leu Gly Leu Ser Gln Met
                645                 650                 655
Leu His Ile Ala Ser Gln Ile Ala Ser Gly Met Val Tyr Leu Ala Ser
            660                 665                 670
Gln His Phe Val His Arg Asp Leu Ala Thr Arg Asn Cys Leu Val Gly
        675                 680                 685
Ala Asn Leu Leu Val Lys Ile Gly Asp Phe Gly Met Ser Arg Asp Val
690                 695                 700
Tyr Ser Thr Asp Tyr Tyr Arg Leu Phe Asn Pro Ser Gly Asn Asp Phe
705                 710                 715                 720
Cys Ile Trp Cys Glu Val Gly Gly His Thr Met Leu Pro Ile Arg Trp
                725                 730                 735
Met Pro Pro Glu Ser Ile Met Tyr Arg Lys Phe Thr Thr Glu Ser Asp
            740                 745                 750
Val Trp Ser Phe Gly Val Ile Leu Trp Glu Ile Phe Thr Tyr Gly Lys
        755                 760                 765
Gln Pro Trp Phe Gln Leu Ser Asn Thr Glu Val Ile Glu Cys Ile Thr
770                 775                 780
Gln Gly Arg Val Leu Glu Arg Pro Arg Val Cys Pro Lys Glu Val Tyr
785                 790                 795                 800
Asp Val Met Leu Gly Cys Trp Gln Arg Glu Pro Gln Gln Arg Leu Asn
                805                 810                 815
Ile Lys Glu Ile Tyr Lys Ile Leu His Ala Leu Gly Lys Ala Thr Pro
            820                 825                 830
Ile Tyr Leu Asp Ile Leu Gly
        835

<210> SEQ ID NO 7
<211> LENGTH: 7
<212> TYPE: PRT
<213> ORGANISM: Artificial
<220> FEATURE:
<223> OTHER INFORMATION: human (Homo sapiens)

<400> SEQUENCE: 7

Lys Asn Glu Tyr Gly Lys Asp
1               5
```

<210> SEQ ID NO 8
<211> LENGTH: 6
<212> TYPE: PRT
<213> ORGANISM: Artificial
<220> FEATURE:
<223> OTHER INFORMATION: Human (Homo sapiens)

<400> SEQUENCE: 8

Lys Gly Asn Pro Lys Pro
1               5

<210> SEQ ID NO 9
<211> LENGTH: 6
<212> TYPE: PRT
<213> ORGANISM: Artificial
<220> FEATURE:
<223> OTHER INFORMATION: murine (Mus musculus)

<400> SEQUENCE: 9

Arg Gly Asn Pro Lys Pro
1               5

<210> SEQ ID NO 10
<211> LENGTH: 7
<212> TYPE: PRT
<213> ORGANISM: Artificial
<220> FEATURE:
<223> OTHER INFORMATION: human (Homo sapiens)

<400> SEQUENCE: 10

Glu Asn Leu Val Gly Glu Asp
1               5

<210> SEQ ID NO 11
<211> LENGTH: 6
<212> TYPE: PRT
<213> ORGANISM: Artificial
<220> FEATURE:
<223> OTHER INFORMATION: human (Homo sapiens)

<400> SEQUENCE: 11

Ala Gly Asp Pro Val Pro
1               5

<210> SEQ ID NO 12
<211> LENGTH: 71
<212> TYPE: PRT
<213> ORGANISM: Artificial Sequence
<220> FEATURE:
<223> OTHER INFORMATION: Human - (homo sapiens) TrkB IGG-1 domain

<400> SEQUENCE: 12

Gly Lys Ser Ile Thr Leu Ser Cys Ser Val Ala Gly Asp Pro Val Pro
1               5                   10                  15

Asn Met Tyr Trp Asp Val Gly Asn Leu Val Ser Lys His Met Asn Glu
            20                  25                  30

Thr Ser His Thr Gln Gly Ser Leu Arg Ile Thr Asn Ile Ser Ser Asp
        35                  40                  45

Asp Ser Gly Lys Gln Ile Ser Cys Val Ala Glu Asn Leu Val Gly Glu
    50                  55                  60

Asp Gln Asp Ser Val Asn Leu
65                  70

-continued

```
<210> SEQ ID NO 13
<211> LENGTH: 77
<212> TYPE: PRT
<213> ORGANISM: Artificial Sequence
<220> FEATURE:
<223> OTHER INFORMATION: Human - (homo sapiens) TrkB - IGG-2 domain

<400> SEQUENCE: 13

Pro Thr Ser Asp His His Trp Cys Ile Pro Phe Thr Val Lys Gly Asn
1               5                   10                  15

Pro Lys Pro Ala Leu Gln Trp Phe Tyr Asn Gly Ala Ile Leu Asn Glu
            20                  25                  30

Ser Lys Tyr Ile Cys Thr Lys Ile His Val Thr Asn His Thr Glu Tyr
        35                  40                  45

His Gly Cys Leu Gln Leu Asp Asn Pro Thr His Met Asn Asn Gly Asp
    50                  55                  60

Tyr Thr Leu Ile Ala Lys Asn Glu Tyr Gly Lys Asp Glu
65                  70                  75
```